US008513485B2

(12) United States Patent
Heintz et al.

(10) Patent No.: US 8,513,485 B2
(45) Date of Patent: Aug. 20, 2013

(54) NON HUMAN TRANSGENIC MAMMAL COMPRISING A TRANSGENE COMPRISING A NUCLEOTIDE SEQUENCE ENCODING A RIBOSOMAL PROTEIN FUSED TO A PEPTIDE TAG

(75) Inventors: Nathaniel Heintz, Pelham Manor, NY (US); Tito A. Serafini, San Mateo, CA (US); Andrew W. Shyjan, San Carlos, CA (US)

(73) Assignee: Envoy Therapeutics, Inc., Jupiter, FL (US)

( * ) Notice: Subject to any disclaimer, the term of this patent is extended or adjusted under 35 U.S.C. 154(b) by 0 days.

(21) Appl. No.: 13/104,316

(22) Filed: May 10, 2011

(65) Prior Publication Data
US 2011/0314565 A1 Dec. 22, 2011

Related U.S. Application Data

(63) Continuation of application No. 10/494,248, filed as application No. PCT/US02/34645 on Oct. 29, 2002, now Pat. No. 7,985,553.

(60) Provisional application No. 60/340,689, filed on Oct. 29, 2001.

(51) Int. Cl.
*A01K 67/027* (2006.01)
*G01N 33/00* (2006.01)
*C12N 15/00* (2006.01)

(52) U.S. Cl.
USPC ... 800/14; 800/18; 800/4; 800/25; 435/320.1; 435/354

(58) Field of Classification Search
None
See application file for complete search history.

(56) References Cited

U.S. PATENT DOCUMENTS

| | | | |
|---|---|---|---|
| 5,075,227 A | 12/1991 | Hagen | |
| 5,795,723 A | 8/1998 | Tapscott et al. | |
| 6,110,711 A | 8/2000 | Serafini et al. | |
| 6,130,090 A | 10/2000 | Heintz et al. | |
| 6,143,566 A | 11/2000 | Heintz et al. | |
| 6,156,574 A | 12/2000 | Heintz et al. | |
| 6,252,130 B1 | 6/2001 | Federoff | |
| 6,270,969 B1 | 8/2001 | Hartley et al. | |
| 6,403,374 B1 | 6/2002 | Tsien et al. | |
| 6,410,317 B1 | 6/2002 | Farmer | |
| 6,441,269 B1 | 8/2002 | Serafini et al. | |
| 6,485,912 B1 | 11/2002 | Heintz et al. | |
| 6,495,318 B2 | 12/2002 | Harney | |
| 6,635,422 B2 | 10/2003 | Keene et al. | |
| 6,821,759 B1 | 11/2004 | Heintz et al. | |
| 7,098,031 B2 | 8/2006 | Choulika et al. | |
| 7,297,482 B2 | 11/2007 | Anderson et al. | |
| 7,393,632 B2 | 7/2008 | Cheo et al. | |
| 7,985,553 B2 | 7/2011 | Heintz et al. | |

| | | |
|---|---|---|
| 2003/0119104 A1 | 6/2003 | Perkins et al. |
| 2004/0023256 A1 | 2/2004 | Puglisi et al. |
| 2011/0071049 A1 | 3/2011 | Heintz et al. |

FOREIGN PATENT DOCUMENTS

| | | |
|---|---|---|
| EP | 1132479 A1 | 9/2001 |
| WO | WO 01/48480 A1 | 7/2001 |
| WO | WO 01/58954 A2 | 8/2001 |
| WO | WO 01/58954 A3 | 3/2002 |
| WO | WO 02/064749 A2 | 8/2002 |
| WO | WO 01/58954 A3 | 1/2003 |
| WO | WO 02/064749 A3 | 3/2003 |
| WO | WO 03/064604 A2 | 8/2003 |
| WO | WO 03/064604 A3 | 11/2003 |

OTHER PUBLICATIONS

Kubota et al. Nuclear and nucleolar targeting of human ribosomal protein S25: Common features shared with HIV-1 regulatory proteins,. Oncogene, 1999, vol. 18, pp. 1503-1514.*
Lalanne et al.Complete sequence of mouse S6 ribosomal protein. Nucleic Acids Res., 1987, vol. 15, pp. 4990.*
Copeland et al. A novel RNA binding protein, SBP2, is reqauired for the translation of mammalian selenoprotein mRNA's. EMBO J., 2000, vol. 17, pp. 306-314.*
Chambers et al. Tranlational Regulation of Hepatic HMG-CoA Reductase by Dietary Cholesterol. Biochem. Biophys. Research Comm., 1997, vol. 232, pp. 278-281.*
Ristevski. Making Better Transgenic Models. Molecular Biotechnology, 2005, vol. 29, pp. 153-163.*
Smith. Gene Transfer in Higher Animals: Theoretical Considerations and Key Concepts. J. Biotechnology, 2002, vol. 99, pp. 1-22. Smith. Gene Transfer in Higher Animals: Theoretical Considerations and Key Concepts. J. Biotechnology, 2002, vol. 99, pp. 1-22.*
Agafonov, et al. Proteins on ribosome surface: measurements of protein exposure by hot tritium bombardment technique. Proc Natl Acad Sci U S A. Nov. 25, 1997;94(24):12892-7.
Anthony, et al. Cre-ating somatic cell genetic mosaics in the mouse. Cell. May 6, 2005;121(3):322-3.

(Continued)

*Primary Examiner* — Deborah Crouch
(74) *Attorney, Agent, or Firm* — Wilson Sonsini Goodrich & Rosati

(57) ABSTRACT

The invention provides methods for isolating cell-type specific mRNAs by selectively isolating ribosomes or proteins that bind mRNA in a cell type specific manner, and, thereby, the mRNA hound to the ribosomes or proteins that bind mRNA. Ribosomes, which are riboprotein complexes, bind mRNA that is being actively translated in cells. According to the methods of the invention, cells are engineered to express a molecularly tagged ribosomal protein or protein that binds mRNA by introducing into the cell a nucleic acid comprising a nucleotide sequence encoding a ribosomal protein or protein that binds mRNA fused to a nucleotide sequence encoding a peptide tag. The tagged ribosome or mRNA binding protein can then be isolated, along with the mRNA bound to the tagged ribosome or mRNA binding protein, and the mRNA isolated and further used for gene expression analysis. The methods of the invention facilitate the analysis and quantification of gene expression in the selected cell type present within a heterogeneous cell mixture, without the need to isolate the cells of that cell type as a preliminary step.

75 Claims, 2 Drawing Sheets

(56) References Cited

OTHER PUBLICATIONS

Antic, et al. ELAV tumor antigen, Hel-N1, increases translation of neurofilament M mRNA and induces formation of neurites in human teratocarcinoma cells. Genes Dev. Feb. 15, 1999;13(4):449-461.
Ashiya, et al. A neuron-specific splicing switch mediated by an array of pre-mRNA repressor sites: evidence of a regulatory role for the polypyrimidine tract binding protein and a brain-specific PTB counterpart. RNA. Sep. 1997;3(9):996-1015.
Brodersen, et al. The social life of ribosomal proteins. FEBS J. May 2005;272(9):2098-2108.
Broude, et al. Proteins of the 30-S subunit of *Escherichia coli* ribosomes which interact directly with natural mNRA. Eur J Biochem. Apr. 15, 1983;132(1):139-45.
Buskila, et al. Serum monoclonal antibodies derived from patients with multiple myeloma react with mycobacterial phosphoinositides and nuclear antigens. Clin Exp Immunol. Jun. 1989;76(3):378-83.
Ceman, et al. Isolation of an FMRP-associated messenger ribonucleoprotein particle and identification of nucleolin and the fragile X-related proteins as components of the complex. Mol Cell Biol. Dec. 1999;19(12):7925-32.
Christopher, et al. Implications of N and C-terminal proximity for protein folding. J Mol Biol. Mar. 22, 1996;257(1):175-87.
Chu, et al. Identification of a thymidylate synthase ribonucleoprotein complex in human colon cancer cells. Mol Cell Biol. Jan. 1994;14(1):207-213.
Chu, et al. Identification of in vivo target RNA sequences bound by thymidylate synthase. Nucleic Acids Res. Aug. 15, 1996;24(16):3222-8.
Das, et al. Functional association of U2 snRNP with the ATP-independent spliceosomal complex E. Mol Cell. May 2000;5(5):779-87.
De Jonge et al., "Transcriptional profile of the human peripheral nervous system by serial analysis of gene expression," Genomics 82(2):97-108, 2003.
Doyle, et al. Application of a translational profiling approach for the comparative analysis of CNS cell types. Cell. 2008;doi:10.1016/j.cell.2008.10.029. (Cell. 2008;135:749-762).
European search report and opinion dated Feb. 21, 2012 for EP Application No. 09719684.4.
Fisher, et al. Pulse labeling of small nuclear ribonucleoproteins in vivo reveals distinct patterns of antigen recognition by human autoimmune antibodies. Proc Natl Acad Sci U S A. May 1984;81(10):3185-9.
Fredrick, et al. Tagging ribosomal protein S7 allows rapid identification of mutants defective in assembly and function of 30 S subunits. J Mol Biol. May 5, 2000;298(3):379-94.
Gerfen, et al. D1 and D2 dopamine receptor-regulated gene expression of striatonigral and striatopallidal neurons. Science. 1990; 250(4986):1429-1432.
Gimautdinova, et al. The proteins of the messenger RNA binding site of *Escherichia coil* ribosomes. Nucleic Acids Res. Jul. 24, 1981;9(14):3465-81.
Gong, et al. A gene expression atlas of the central nervous system based on bacterial artificial chromosomes. Nature. Oct. 30, 2003;425(6961):917-25.
Gong, et al. Highly efficient modification of bacterial artificial chromosomes (BACs) using novel shuttle vectors containing the R6Kgamma origin of replication. Genome Res. Dec. 2002;12(12):1992-8.
Gong, et al. Targeting Cre recombinase to specific neuron populations with bacterial artificial chromosome constructs. J Neurosci. Sep. 12, 2007;27(37):9817-23.
Gonzalo and Reboud, "The puzzling lateral flexible stalk of the ribosome," Biol Cell 95(3-4):179-93, 2003.
Hagen-Mann et al. RT-PCR and alternative methods to PCR for in vitro amplification of nucleic acids. Exp Clin Endocrinol Diabetes. 1995; 103(3):150-5.
Heiman, et al. A translational profiling approach for the molecular characterization of CNS cell types. Cell. 2008;dok:10.1016/j.cell.2008.10.028. (Cell. 2008;135(4):738-748).

Heintz, N. Analysis of mammalian central nervous system gene expression and function using bacterial artificial chromosome-mediated transgenesis. Hum Mol Genet. Apr. 12, 2000;9(6):937-43.
Heintz, N. BAC to the future: the use of bac transgenic mice for neuroscience research. Nat Rev Neurosci. Dec. 2001;2(12):861-70.
Heintz, N. Gene expression nervous system atlas (GENSAT). Nature Neuroscience. 2004; 7(5):483.
Heller, et al. Discovery and analysis of inflammatory disease-related genes using cDNA microarrays. Proc Natl Acad Sci U S A. Mar. 18, 1997;94(6):2150-2155.
Kalapos, et al. Identification of ribosomal protein S1 as a poly(A) binding protein in *Escherichia coli*. Biochimie. Sep. 1997;79(8):493-502.
Lee, et al. Cocaine-induced dendritic spine formation in D1 and D2 dopamine receptor-containing medium spiny neurons in nucleus accumbens. Proc. Natl. Acad. Sci. USA. 2006; 103(9):3399-3404.
Lerner and Steitz, "Antibodies to small nuclear RNAs complexed with proteins are produced by patients with systemic lupus erythematosus," Proc Natl Acad Sci U S A 76(11):5495-9, 1979.
Liang, et al. An estrogen-dependent polysomal protein binds to the 5' untranslated region of the chicken vitellogenin mRNA. Nucleic Acids Res. May 11, 1991;19(9):2289-94.
Lin, et al. The primary structure of rat liver ribosomal protein L37. Homology with yeast and bacterial ribosomal proteins. J Biol Chem. Sep. 10, 1983;258(17):10664-71.
Misulovin, et al. A rapid method for targeted modification and screening of recombinant bacterial artificial chromosome. J Immunol Methods. Nov. 1, 2001;257(1-2):99-105.
Nevskaya et al., "Ribosomal protein L1 recognizes the same specific structural motif in its target sites on the autoregulatory mRNA and 23S rRNA," Nucleic Acids Res 33(2):478-85, 2005.
Noain et al., "Identification of brain neurons expressing the dopamine D4 receptor gene using BAC transgenic mice," Eur J Neurosci 24(9):2429-38, 2006.
Office action dated Dec. 23, 2010 for U.S. Appl. No. 10/494,248.
Peng, et al. RNA stabilization by the AU-rich element binding protein, HuR, an ELAV protein. EMBO J. Jun. 15, 1998;17(12):3461-70.
Remacha et al., "Proteins P1, P2, and P0, components of the eukaryotic ribosome stalk. New structural and functional aspects," Biochem Cell Biol 73(11-12):959-68, 1995.
Roche, et al. SsrA-mediated peptide tagging caused by rare codons and tRNA scarcity. EMBO J. Aug. 16, 1999;18(16):4579-89.
Rusk, N. Targeted translational profiling. Nature Methods. 2009; 6(1):7.
Sano, et al. Streptavidin-containing chimeric proteins: design and production. Methods Enzymol. 2000;326:305-11.
Sanz, et al. Cell-type-specific isolation of ribosome-associated mRNA from complex tissues. Proc Natl Acad Sci U S A. Aug. 18, 2009;106(33):13939-44.
Schena, et al. Parallel human genome analysis: microarray-based expression monitoring of 1000 genes. Proc Natl Acad Sci U S A. Oct. 1, 1996;93(20):10614-10619.
Tallini et al., "BAC transgenic mice express enhanced green fluorescent protein in central and peripheral cholinergic neurons," Physiol Genomics 27(3):391-7, 2006.
Tenenbaum, et al. Identifying mRNA subsets in messenger ribonucleoprotein complexes by using cDNA arrays. Proc Natl Acad Sci U S A. Dec. 19, 2000;97(26):14085-90.
Trifillis, et al. Finding the right RNA: identification of cellular mRNA substrates for RNA-binding proteins. RNA. Aug. 1999;5(8):1071-82.
Uchiumi and Kominami, "Binding of mammalian ribosomal protein complex P0.P1.P2 and protein L12 to the GTPase-associated domain of 28 S ribosomal RNA and effect on the accessibility to anti-28 S RNA autoantibody," J Biol Chem 272(6):3302-8, 1997.
Walles-Granberg, et al. Ribosomes with large synthetic N-terminal extensions of protein S15 are active in vivo. Biochim Biophys Acta. Jan. 12, 2001;1544(1-2):378-85.
Wilson, et al. Ribosomal proteins in the spotlight. Crit Rev Biochem Mol Biol. Sep.-Oct. 2005;40(5):243-67.

Yang, et al. Homologous recombination based modification in *Escherichia coli* and germline transmission in transgenic mice of a bacterial artificial chromosome. Nat Biotechnol. Sep. 1997;15(9):859-65.

Zong, et al. Messenger RNA translation state: The second dimension of high-throughput expression screening. PNAS. 1999; 96(19):10632-10636.

Chaible, et al. Genetically modified animals for use in research and biotechnology. Genet Mol Res. Jul. 27, 2010;9(3):1469-82. doi: 10.4238/vol9-3gmr867.

Yang, et al. BAC-mediated gene-dosage analysis reveals a role for Zipro1 (Ru49/Zfp38) in progenitor cell proliferation in cerebellum and skin. Nat Genet. Aug. 1999;22(4):327-35.

Office action dated Feb. 19, 2010 for U.S. Appl. No. 10/494,248.
Office action dated Jun. 5, 2009 for U.S. Appl. No. 10/494,248.
Office action dated Jul. 29, 2008 for U.S. Appl. No. 10/494,248.
Office action dated Sep. 25, 2007 for U.S. Appl. No. 10/494,248.

\* cited by examiner

NON HUMAN TRANSGENIC MAMMAL COMPRISING A TRANSGENE COMPRISING A NUCLEOTIDE SEQUENCE ENCODING A RIBOSOMAL PROTEIN FUSED TO A PEPTIDE TAG

This application is a continuation of application Ser. No. 10/494,248, filed on Aug. 16, 2004, now U.S. Pat. No. 7,985,553, which is a 371 National Stage of International Application No. PCT/US02/34645 filed on Oct. 29, 2002, which claims the benefit of Application No. 60/340,689, filed Oct. 29, 2001, the entire disclosure of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 28, 2011, is named 36812301.txt and is 4,669 bytes in size.

TECHNICAL FIELD

The present invention relates to methods for isolating cell-type specific mRNAs by isolating ribosomes in a cell-type specific manner. According to the methods of the invention, ribosomes or proteins that bind mRNA of the selected cell type are molecularly tagged and isolated, and the mRNA bound to the ribosomes or proteins that bind mRNA is then isolated and analyzed. The methods of the invention facilitate the analysis and quantification of gene expression in the selected cell type present within a heterogeneous cell mixture, without the need to isolate the cells of that cell type as a preliminary step.

BACKGROUND OF THE INVENTION

An important paradigm in the development of new diagnostics and therapies for human diseases and disorders is the characterization of the gene expression of defined cell types. The cellular complexity of many tissues (such as the nervous system), however, poses a challenge for those seeking to characterize gene expression at this level. The enormous heterogeneity of a tissue such as the nervous system (thousands of neuronal cell types, with non-neuronal cells outnumbering neuronal cells by an order of magnitude) is a barrier to the identification and analysis of gene transcripts present in individual cell types. One way to overcome this barrier is to tag gene transcripts directly or indirectly, i.e., mRNA, present in a particular cell type, in such a manner as to allow facile isolation of the gene transcripts without the need to isolate the individual cells of that cell type as a preliminary step. We describe such a technology here.

SUMMARY OF THE INVENTION

The invention provides methods for isolating cell-type specific mRNAs by selectively isolating ribosomes or proteins that bind mRNA in a cell type specific manner, and, thereby, the mRNA bound to the ribosomes or proteins that bind mRNA. Ribosomes, which are riboprotein complexes, bind mRNA that is being actively translated in cells. According to the methods of the invention, cells are engineered to express a molecularly tagged ribosomal protein or protein that binds mRNA by introducing into the cell a nucleic acid comprising a nucleotide sequence encoding a ribosomal protein or proteins that bind mRNA fused to a nucleotide sequence encoding a peptide tag. The peptide tag can be any non-ribosomal protein peptide or non-mRNA binding protein peptide that is specifically bound by a reagent that either does not recognize a component of the cell fraction from which the tagged ribosomes or proteins that bind mRNA are to be isolated, for example, from a whole cell lysate or post-mitochondrial fraction (or any other ribosome or polysome preparation or other preparation containing the tagged protein that binds mRNA being analyzed). In a preferred embodiment, the polysome preparation is a membrane-associated polysome preparation. Specifically, the peptide tag may be an epitope that is recognized by an antibody that does not specifically bind any epitope expressed in a cell or ribosome/polysome fraction from an unengineered cell. As defined herein, specific binding is not competed away by addition of non-specific proteins, e.g., bovine serum albumen (BSA). The tagged ribosomal protein or mRNA binding protein is then expressed selectively in a cell population of interest (for example, by operably linking the nucleotide sequence encoding the tagged ribosomal protein or mRNA binding protein to a cell-type specific promoter and/or other transcriptional element). In a preferred embodiment, the tagged ribosomal protein or mRNA binding protein is overexpressed.

Monosomes or polysomes (which are, respectively, single or multiple ribosomes in a complex with a single mRNA) or other mRNA-containing complex are isolated selectively from the cell population of interest through the use of the tagged ribosomal protein subunit or other mRNA binding protein. As used herein, isolated means that the ribosomes are separated from other cell components, specifically that the ribosomes are substantially free of untagged ribosomes and of RNA (particularly mRNA) not bound by ribosomes or mRNA binding protein. In particular, the composition is 50%, 60%, 70%, 80%, 90%, 95% or 99% tagged ribosome or mRNA binding protein and associated mRNA. The mRNA species that are bound to the cell-type specific ribosomes or mRNA binding protein are then isolated, and can subsequently be profiled and quantified, to analyze gene expression in the cell. In a specific embodiment, because nascent polypeptides are attached to isolated monosomes and polysomes, the methods of the invention can also be used to isolate newly synthesized polypeptides from a cell type of interest (e.g., for proteomic applications), for example, using antibodies that specifically recognize an epitope on a specific polypeptide being synthesized by the cell.

In preferred embodiments, the invention provides transformed organisms (including animals, plants, fungi and bacteria), e.g., a transgenic animal such as a transgenic mouse, that expresses one or more tagged ribosomal protein(s) or mRNA binding protein(s) within a chosen cell type. The invention also provides cultured cells that express one or more tagged ribosomal proteins or mRNA binding proteins. Cell-type specific expression is achieved by driving the expression of the tagged ribosomal protein using the endogenous promoter of a particular gene, wherein the expression of the gene is a defining characteristic of the chosen cell type (i.e., the promoter causes gene expression specifically in the chosen cell type). Thus, "cell-type" refers to a population of cells characterized by the expression of a particular gene. In a preferred embodiment, a collection of transgenic mice expressing tagged ribosomal proteins within a set of chosen cell types is assembled. Additionally, since the level of expression of the tagged ribosomal protein or mRNA binding protein within a cell may be important in the efficiency of the isolation procedure, in certain embodiments of the invention, a binary system can be used, in which the endogenous promoter drives expression of a protein that then activates a second expression construct. This second expression construct uses a strong promoter to drive expression of the tagged ribosomal protein or mRNA binding protein at higher levels than is possible using the endogenous promoter itself.

In specific embodiments, the invention provides molecularly tagged ribosomes, preferably bound to mRNA, that are bound to an affinity reagent for the molecular tag. In more specific embodiments, the molecularly tagged ribosomes are bound to an affinity reagent which is bound to a solid support. In other particular embodiments, the invention provides molecularly tagged ribosomal proteins and mRNA binding proteins of the invention (and the ribosomes, ribosomal-mRNA complexes, and mRNA binding protein-mRNA complexes containing them); nucleic acids comprising nucleotide sequences encoding a molecularly tagged ribosomal protein or mRNA binding protein of the invention; vectors and host cells comprising these nucleic acids and tagged proteins and ribosomes of the inventions.

The methods of the invention are advantageous because they permit the isolation of gene transcripts, or mRNA, present in a particular cell type, as defined by the common expression of a given gene, in such a manner as to allow their facile isolation without the need to isolate the individual cells of that cell type as a preliminary step.

Additionally, in specific embodiments, the methods of the invention may be used to isolate other organelles or subcellular structures by molecularly tagging proteins integral to those organelles or structures. In a particular embodiment, the methods of the invention are used to isolate cell specific mRNAs for secreted, membrane bound and lysomal proteins by isolating tagged membrane bound ribosomes.

DETAILED DESCRIPTION OF THE INVENTION

Figure 1:
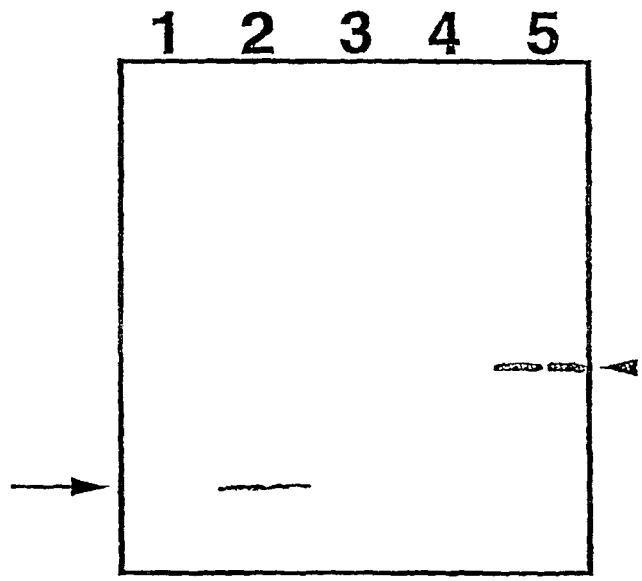
FIG. 1. Polysomes from cells transfected with plasmids expressing tagged versions of ribosomal proteins S6 (lane 2, in duplicate), L32 (lane 4, in duplicate), and L37 (lane 5, in duplicate) contain proteins that are reactive to the anti-streptag II antibodies. These proteins correspond to the predicted molecular weights of the S6 (34 kDa), L32 (52 kDa), and L37 (9 kDa) ribosomal proteins. The S6 and L37 proteins appear to be more abundantly represented in the polysomal fraction compared to the L32 protein. Tagged S20 (lane 3, in duplicate) does not appear to be present in the polysomal fraction. Polysomes from untransfected cells (lane 1, in duplicate) do not display any immunoreactive material.

The invention provides methods for isolating cell-type specific mRNAs by selectively isolating ribosomes, or other proteins that bind mRNA, in a cell type specific manner, and, thereby, the mRNA bound to the ribosomes or mRNA binding proteins. Ribosomes, which are riboprotein complexes, bind mRNA that is being actively translated in cells. According to the methods of the invention, preferably, cells are engineered to express a molecularly tagged ribosomal protein or mRNA binding protein by introducing into the cell a nucleic acid comprising a nucleotide sequence encoding a ribosomal protein or mRNA binding protein fused to a nucleotide sequence encoding a peptide tag. The peptide tag can be any peptide that is not from a ribosomal protein or mRNA binding protein and that is specifically bound by a reagent that does not recognize a component, other than the peptide tag, of the cell fraction from which the tagged ribosomes or mRNA binding proteins are to be isolated, for example, from a whole cell lysate or post-mitochondrial fraction (or any other ribosome or polysome preparation or preparation containing mRNA binding protein bound to mRNA being analyzed). For example, the peptide tag may be an epitope that is recognized by an antibody that does not specifically bind any epitope expressed in a cell or ribosome/polysome fraction (or other fraction) from an unengineered cell. As defined herein, specific binding is not competed away by addition of non-specific proteins, e.g., bovine serum albumen (BSA).

The tagged ribosomal protein or mRNA binding protein is then expressed selectively in a cell population of interest (for example, by operably linking the nucleotide sequence encoding the tagged ribosomal or mRNA binding protein to a cell-type specific promoter, enhancer and/or other transcriptional element). The fused nucleotide sequences may be under the control of a transcriptional element (e.g., promoter or enhancer) that activates transcription specifically in the cell type of choice (for example, transcriptional regulatory elements that control expression of the gene, the expression of which characterizes the cell type of choice, termed herein the "characterizing gene"). In a preferred embodiment, the tagged ribosomal or mRNA binding protein is overexpressed. Cell-specific polysomes (or other fraction containing the tagged mRNA binding protein) containing the tag are purified, exploiting affinity of a purification reagent (e.g., an antibody or other biological compound that binds the tag) for the tag. The purification reagent can then be isolated itself or be bound to another structure, e.g., a bead, that can be isolated from other components in the cell, and bound mRNA is isolated from purified polysomes for subsequent gene expression analysis.

5.1. Molecular Tagging of Ribosomes and mRNA Binding Proteins

The invention provides methods for isolating cell-type specific mRNA using molecularly tagged ribosomal proteins that become incorporated into the ribosomes of a particular cell type or molecularly tagged mRNA binding proteins that are expressed in a particular cell type of interest. Specifically, ribosomes and mRNA binding proteins can be molecularly tagged by expressing in the cell type of interest a ribosomal fusion protein or mRNA binding protein fusion protein containing all or a portion of a ribosomal or mRNA binding protein (preferably, the portion has the biological activity of the native ribosomal protein or mRNA binding protein, i.e., can function in an intact ribosome to carry out translation or binds mRNA) fused to (for example, through a peptide bond) a protein or peptide tag that is not a ribosomal protein or mRNA binding protein or portion thereof, or, preferably, found in the organism in which the tagged protein is being expressed. Such expression can be carried out by introducing into cells, or into an entire organism, a nucleic acid encoding the molecularly tagged ribosomal protein or mRNA binding protein, under the control of transcriptional regulatory elements that direct expression in the cell type of choice, or putting the expression of the ribosomal or mRNA fusion protein under the control of an endogenous promoter by homologous recombination or in a bacterial artificial chromosome ("BAC").

The invention further provides methods for isolating cell-type specific mRNA by tagging proteins that bind to mRNA, preferably actively translated mRNA. In a preferred embodiment, the protein that binds mRNA is not poly A binding protein. In another embodiment, the protein that binds mRNA is a CAP binding protein or a processing factor that binds the 3' untranslated region of the mRNA. In certain other embodiments, the ribosome or mRNA binding protein is molecularly tagged by engineering the ribosome or mRNA binding protein to bind a small molecule, e.g., a peptide, that is not significantly bound by the unengineered ribosome or mRNA binding protein.

The nucleic acid encoding the ribosomal protein or other mRNA binding protein fused to the peptide tag can be generated by routine genetic engineering methods in which a nucleotide sequence encoding the amino acid sequence for the peptide tag sequence is engineered in frame with the nucleotide sequence encoding a ribosomal protein or mRNA binding protein. This can be accomplished by any method known in the art, for example, via oligonucleotide-mediated site-directed mutagenesis or polymerase chain reaction and other routine protocols of molecular biology (see, e.g., Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties). In certain embodiments, the method of Walles-Granberg et al. (Biochim. Biophys. Acta, 2001, 1544(1-2): 378-385, which is incorporated herein by reference in its entirety) is used.

The nucleotide sequence encoding the peptide tag is preferably inserted in frame such that the tag is placed at the N- or C-terminus of the ribosomal protein, since these portions of proteins are often accessible to detection or purification reagents. The peptide tag, however, may be inserted into any portion of the ribosomal protein such that when the protein is incorporated into an intact ribosome, the insertion of the tag does not prevent ribosomal function and the tag is accessible in the intact ribosome to the purification reagent to be used in the isolation. If a mRNA binding protein is used, the tag may be inserted into any portion of the protein such that the protein binds mRNA and the tag is accessible to the purification reagent.

Encoded peptide tags can be any non-ribosomal protein (or non-mRNA binding) peptide or protein (or portion thereof) that is not present and/or accessible in the cell of interest (or the cell fraction from which the tagged ribosomes or mRNA binding protein are to be affinity isolated) for which there exists an affinity reagent that recognizes the peptide and that is accessible to solution (and thereby, the peptide tag) in the intact ribosomes or mRNA binding protein bound to mRNA.

Molecular tagging with epitopes ("epitope tagging") is well known in the art (reviewed in Fritze C E, Anderson T R. Epitope tagging: general method for tracking recombinant proteins. Methods Enzymol. 2000; 327:3-16; Jarvik J W, Telmer C A. Epitope tagging. Annu Rev Genet. 1998; 32:601-18). An epitope tag can be any peptide protein that is not normally present and/or accessible in the cell of interest (or other cells that will be contacted with the reagent that binds the tag) for which there exists an antibody that recognizes the protein, and that is accessible to solution in the intact ribosomes or mRNA binding protein-mRNA complexes.

Peptide tags can include those for which methods/reagents exist that allow facile identification of the tagged ribosomal protein or mRNA binding protein, but are unlikely to inhibit or interfere with function of the tagged ribosomal protein or mRNA binding protein. The tag may be of any length that permits binding to the corresponding binding reagent, but does not interfere with the tagged proteins binding to the mRNA. In a preferred embodiment, the tag is about 8, 10, 12, 15, 18 or 20 amino acids, is less than 15, 20, 25, 30, 40 or 50 amino acids, but may be 100, 150, 200, 300, 400 or 500 or more amino acids in length. The tag may be bound specifically by a reagent that does not bind any component of: (1) the cell of interest; or (2) a polysomal preparation of interest; or (3) whatever cellular fraction of interest is being contacted by the reagent that binds the tag. Molecular tags may include, by way of example, and not by limitation, protein A fragments; myc epitopes (Evan et al., Mol. Cell. Biol. 5(12):3610-3616); Btag (Wang et al., 1996, Gene 169(1): 53-58; and polyhistidine tracts (Bomhorst et al., 2000, Purification of proteins using polyhistidine affinity tags, Methods Enzymol 326:245-54). Other preferred tags include, but are not limited to:

(1) a portion of the influenza virus hemagglutinin protein (Tyr-Pro-Tyr-Asp-Val-Pro-Asp-Tyr-Ala; SEQ ID NO: 1). The reagent used for purification is a monoclonal antibody recognizing the tagged protein (12CA5) (Wilson I A, Niman H L, Houghten R A, Cherenson A R, Connolly M L, Lerner R A. The structure of an antigenic determinant in a protein. Cell. 1984 July; 37(3):767-78).

(2) a portion of the human c-myc gene (Glu-Gln-Lys-Leu-Ile-Ser-Glu-Glu-Asp-Leu; SEQ ID NO: 2). The reagent used for purification is a monoclonal antibody recognizing the tagged protein (9E10) (Evan G I, Lewis G K, Ramsay G, Bishop J M. Isolation of monoclonal antibodies specific for human c-myc proto-oncogene product. Mol Cell Biol. 1985 December; 5(12):3610-6).

(3) a portion of the bluetongue virus VP7 protein (Gln-Tyr-Pro-Ala-Leu-Thr; SEQ ID NO: 3). The reagent used for purification is a monoclonal antibody recognizing the tagged protein (D11 and/or F10) (Wang L F, Yu M, White J R, Eaton B T. BTag: a novel six-residue epitope tag for surveillance and purification of recombinant proteins. Gene. 1996 Feb. 22; 169(1):53-8)

(4) a FLAG peptide (e.g., Asp-Tyr-Lys-Asp-Asp-Asp-Asp-Lys; SEQ ID NO: 4). The reagent used for purification are monoclonal antibodies recognizing the tagged protein (e.g., M1 and/or M2) (Sigma) (Hopp et al., U.S. Pat. No. 4,703,004, entitled "Synthesis of protein with an identification peptide" issued Oct. 27, 1987; Brizzard B L, Chubet R G, Vizard D L. Immunoaffinity purification of FLAG epitope-tagged bacterial alkaline phosphatase using a novel monoclonal antibody and peptide elution. Biotechniques. 1994 April; 16(4):730-5; Knappik A, Pluckthun A. An improved affinity tag based on the FLAG peptide for the detection and purification of recombinant antibody fragments. Biotechniques. 1994 October; 17(4):754-761)

(5) a Strep-tag peptide (e.g., Ala-Trp-Arg-His-Pro-Gln-Phe-Gly-Gly; SEQ ID NO: 5). In a preferred embodiment, a strep-tag peptide is used. The reagent used for purification is one of several optimized versions of streptavidin that recognizes the tagged protein (IBA GmbH) (Skerra et al., U.S. Pat. No. 5,506,121, entitled Fusion peptides with binding activity for streptavidin, issued Apr. 9, 1996; Skerra A, Schmidt T G. Applications of a peptide ligand for streptavidin: the Strep-tag. Biomol Eng. 1999 Dec. 31; 16(1-4):79-86; Skerra A, Schmidt T G. Use of the Strep-Tag and streptavidin for detection and purification of recombinant proteins. Methods Enzymol. 2000; 326:271-304).

Any ribosomal protein or mRNA binding protein can be molecularly tagged for use in the methods of the invention, as described in this section, provided that when the ribosomal protein is molecularly tagged and incorporated into a ribosome, the ribosome can bind mRNA and, preferably, translate the mRNA into protein, or, when the mRNA binding protein is molecularly tagged, it can bind mRNA. In addition, the tag of the tagged ribosomal protein or mRNA binding protein must be accessible to the purification reagent, so that the reagent can be used to purify the intact ribosomes or mRNA binding protein-mRNA complexes. Preferably, the ribosomal protein or mRNA binding protein to be tagged is from the same species as the cell that is to express the molecularly tagged protein.

Nucleic acids encoding the molecularly tagged ribosomal proteins and mRNA binding proteins of the invention may be produced using routine genetic engineering methods and cloning and expression vectors that are well known in the art. Nucleic acids encoding the ribosomal protein or mRNA binding protein to be molecularly tagged may be obtained using any method known in the art. The sequences for many ribosomal and mRNA binding proteins are known (see Table 2 in Section 5.2 below providing GenBank accession numbers for many human and murine ribosomal proteins). Nucleic acids may be obtained, for example, by PCR using oligonucleotide primers based upon the published sequences. Other related ribosomal and mRNA binding proteins (for example from other species) may be obtained by low, medium or high stringency hybridization of appropriate nucleic acid libraries using the ribosomal or mRNA binding protein in hand as a probe. The nucleic acids encoding the desired ribosomal or mRNA binding protein may then be incorporated into a nucleic acid vector either appropriate for additional molecular manipulations and/or for incorporation and expression in the host cells of interest. The nucleotide sequences encoding the peptide tag may likewise be obtained using methods well known in the art. For example, if the tag is fairly short, a nucleic acid encoding the tag and appropriate for generating a fusion protein with the ribosomal or mRNA binding protein may be constructed using oligonucleotides to form the double stranded nucleic acid encoding the peptide tag. The synthetic nucleic acid may then be cloned and used for generating fusion proteins with ribosomal proteins or mRNA binding proteins.

In certain embodiments, a nucleic acid molecule encoding a molecularly tagged ribosomal protein is intended for a particular expression system, in which the codon frequencies reflect the tRNA frequencies of the host cell or organism in which the protein is expressed. Codon optimization allows for maximum protein expression by increasing the translational efficiency of a gene of interest. Codon optimization is a standard component of custom gene design, and may be obtained from commercial service providers (e.g., Aptagen, Inc., Herndon, Va.; Integrated DNA Technologies, Skokie, Ill.).

The nucleic acid encoding a molecularly tagged ribosomal protein may be a synthetic nucleic acid in which the codons have been optimized for increased expression in the host cell in which it is produced. The degeneracy of the genetic code permits variations of the nucleotide sequence, while still producing a polypeptide having the identical amino acid sequence as the polypeptide encoded by the native DNA sequence. The frequency of individual synonymous codons for amino acids varies widely from genome to genome among eukaryotes and prokaryotes. The overall expression levels of individual genes may be regulated by differences in codon choice, which modulates peptide elongation rates. Native codons may be exchanged for codons of highly expressed genes in the host cells. For instance, the nucleic acid molecule can be optimized for expression of the encoded protein in bacterial cells (e.g., *E. coli*), yeast (e.g., *Pichia*), insect cells (e.g., *Drosophila*), or mammalian cells or animals (e.g., human, sheep, bovine or mouse cells or animals).

Restriction enzyme sites critical for gene synthesis and DNA manipulation can be preserved or destroyed to facilitate nucleic acid and vector construction and expression of the encoded protein. In constructing the synthetic nucleic acids of the invention, it may be desirable to avoid sequences that may cause gene silencing. The codon optimized sequence is synthesized and assembled, and inserted into an appropriate expression vector using conventional techniques well known to those of skill in the art.

In a preferred embodiment, a synthetic nucleic acid encoding a molecularly tagged ribosomal protein comprises at least one codon substitution in which non-preferred or less preferred codon in the natural gene encoding the protein has been replaced by a preferred codon encoding the same amino acid. The relative frequency of use for each codon can vary significantly between species, although certain codons are infrequently used across species (Zhang et al., 1991, Low-usage codons in *Escherichia coli*, yeast, fruit fly, and primates. Gene, 105:61-72). For instance in humans the preferred codons are: Ala (GCC); Arg (CGC); Asn (AAC); Asp (GAC); Cys (TGC); Gln (CAG); Gly (GGC); His (CAC); Ile (ATC); Leu (CTG); Lys (AAG); Pro(CCC); Phe (TTC); Ser (AGC); Thr (ACC); Tyr (TAC); and Val (GTG). Less preferred codons are: Gly (GGG); Ile (ATT); Leu (CTC); Ser (TCC); Val (GTC); and Arg (AGG). All codons that do not fit the description of preferred codons or less preferred codons are non-preferred codons.

In general, the degree of preference of a particular codon is indicated by the prevalence of the codon in highly expressed genes. Codon preference for highly expressed human genes are as indicated in Table 1. For example, "ATC" represents 77% of the Ile codons in highly expressed mammalian genes and is the preferred Ile codon; "ATT" represents 18% of the Ile codons in highly expressed mammalian genes and is the less preferred Ile codon. The sequence "ATA" represents only 5% of the Ile codons in highly expressed human genes and is a non-preferred Ile codon. Replacing a codon with another codon that is more prevalent in highly expressed human genes will generally increase expression of the gene in mammalian cells. Accordingly, the invention includes replacing a less preferred codon with a preferred codon as well as replacing a non-preferred codon with a preferred or less preferred codon.

In a particularly preferred embodiment, the nucleic acid has been optimized for expression of the encoded protein in human or mammalian cells or organisms.

TABLE 1

| Codon Frequency (Percentage) in highly expressed human genes | | | |
|---|---|---|---|
| Ala | GC | C | 53 |
| | | T | 17 |
| | | A | 13 |
| | | G | 17 |
| Arg | CG | C | 37 |
| | | T | 7 |
| | | A | 6 |
| | | G | 21 |
| | AG | A | 10 |
| | | G | 18 |
| Asn | AA | C | 78 |
| | | T | 22 |
| Asp | GA | C | 75 |
| | | T | 25 |
| Leu | CT | C | 26 |
| | | T | 5 |
| | | A | 3 |
| | | G | 58 |
| | TT | A | 2 |
| | | G | 6 |
| Lys | AA | A | 18 |
| | | G | 82 |

TABLE 1-continued

Codon Frequency (Percentage) in highly expressed human genes

| | | | |
|---|---|---|---|
| Pro | CC | C | 48 |
| | | T | 19 |
| | | A | 16 |
| | | G | 17 |
| Phe | TT | C | 80 |
| | | T | 20 |
| Cys | TG | C | 68 |
| | | T | 32 |
| Gln | CA | A | 12 |
| | | G | 88 |
| Glu | GA | A | 25 |
| | | G | 75 |
| Gly | GG | C | 50 |
| | | T | 12 |
| | | A | 14 |
| | | G | 24 |
| His | CA | C | 79 |
| | | T | 21 |
| Ile | AT | C | 77 |
| | | T | 18 |
| | | A | 5 |
| Ser | TC | C | 28 |
| | | T | 13 |
| | | A | 5 |
| | | G | 9 |
| | AG | C | 34 |
| | | T | 10 |
| Thr | AC | C | 57 |
| | | T | 14 |
| | | A | 14 |
| | | G | 15 |
| Tyr | TA | C | 74 |
| | | T | 26 |
| Val | GT | C | 25 |
| | | T | 7 |
| | | A | 5 |
| | | G | 64 |

In particular embodiments, the invention provides fusion proteins (including isolated or purified fusion proteins) containing all or a functional portion of a ribosomal protein or mRNA binding protein and a peptide tag, as described above, as well as intact ribosomes and complexes of mRNA and mRNA binding protein (including isolated and purified intact ribosomes and complexes). The invention further provides nucleic acids comprising nucleotide sequences encoding the ribosomal and mRNA binding protein fusions with peptide tags of the invention, vectors containing these nucleic acids, and host cells containing nucleic acids encoding the ribosomal and mRNA binding protein fusion proteins of the invention.

5.2. Selection of Ribosomal Protein for Tagging

Any ribosomal protein or mRNA binding protein may be molecularly tagged for use in the methods of the invention. The ribosome containing the tagged protein should bind mRNA and, preferably, also translate the mRNA into protein, and the peptide tag in the intact ribosome should be accessible to the corresponding isolation reagent. Likewise, if an mRNA binding protein is used, the tagged mRNA binding protein should bind mRNA, and the peptide tag should be accessible to the corresponding isolation reagent. Accordingly, selection of an appropriate ribosomal protein for tagging can be based upon accessibility to affinity reagents such as antibodies against N- and C-termini or other portions of the proteins in intact ribosomes (Syu W J, Kahan L. Both ends of *Escherichia coli* ribosomal protein S13 are immunochemically accessible in situ. J Protein Chem. 1992 June; 11(3):225-30; reviewed in Syu W J, Kahan B, Kahan L. Detecting immunocomplex formation in sucrose gradients by enzyme immunoassay: application in determining epitope accessibility on ribosomes. Anal Biochem. 1991 July; 196(1):174-7). However, accessibility does not imply that once tagged, the ribosomal protein will function appropriately. One assay of proper function of a tagged variant is the determination, via immunohistochemistry, that the tagged protein displays expected subcellular localization when expressed in cultured cells. The determination that the tag appears in a preparation of polysomes isolated from transfected cells is an indication that ribosomal function is not greatly perturbed by the incorporation of the tagged protein into the organelle. See e.g., Rosorius et al., 2000, Human Ribosomal Protein L5 Contains Defined Nuclear Localization and Export Signals, J. Biol. Chem. 275(16): 12061-12068, and Russo et al., 1997, Different Domains Cooperate to Target the Human Ribosomal L7a Protein to the Nucleus and to the Nucleoli, J. Biol. Chem. 272(8): 5229-5235, both of which are hereby incorporated by reference in their entireties.

More thorough evaluations of any possible perturbation of ribosomal function involves comparisons of cellular physiology in transfected and untransfected cells. For example, comparisons of relative protein or mRNA abundances in transfected and untransfected cells would be such measures of cellular physiology. An appropriate ribosomal protein will be one which, when tagged, is incorporated into ribosomes, allows those ribosomes to function without unduly affecting cellular physiology, and which has the tag positioned so as to be accessible to affinity purification reagents.

The methods of Herfurth et al. (1995, Determination of peptide regions exposed at the surface of the bacterial ribosome with antibodies against synthetic peptides. Biol Chem Hoppe Seyler 376(2):81-90; which is hereby incorporated by reference in its entirety) may be use to determine before tagging which parts of particular ribosomal proteins are accessible in the intact ribosome.

Once accessibility is determined, one can determine whether ribosomes containing the tagged riboprotein are functional using routine assays well known in the art. Analogous tests for accessibility of the tag in tagged mRNA binding proteins and formation and function of the mRNA binding protein-mRNA complex will be apparent to the skilled artisan for identifying and designing appropriate tagged mRNA binding proteins for use in the present invention.

Ribosomal proteins or protein subunits or mRNA binding proteins suitable for use in the methods of the invention are preferably of the same species as the host cell to be transformed, but in certain embodiments, may be of a different species.

Ribosomal proteins or protein subunits suitable for use in the methods of the invention include, but are not limited to mouse and human ribosomal proteins in Tables 2 and 3. In Tables 2 and 3, the GenBank accession number is followed by a description of the ribosomal protein as it appears in GenBank:

TABLE 2

Mouse Ribosomal Proteins

BC006068 - ribosomal protein L10, clone IMAGE: 3593057, mRNA
gi|13543840|gb|BC006068.1|BC006068[13543840]
U17332 - ribosomal protein L9 (musl9) mRNA, partial cds
gi|687603|gb|U17332.1|MMU17332[687603]
U17331 - mutant ribosomal protein L9 (musl9mu) mRNA, partial cds
gi|687601|gb|U17331.1|MMU17331[687601]
AY043296 - ribosomal protein S3 (Rps3) gene, complete cds
gi|15421126|gb|AY043296.1|[15421126]
BC013165 - ribosomal protein L9, clone MGC: 6543 IMAGE: 2655358, mRNA, complete cds TABLE 2-continued Mouse Ribosomal Proteins gi|15341947|gb|BC013165.1|BC013165[15341947]
BC012641 - ribosomal protein S11, clone MGC: 13737 IMAGE: 4019309, mRNA, complete cds
gi|15215035|gb|BC012641.1|BC012641[15215035]
NM_021338 - ribosomal protein L35a (Rpl35a), mRNA
gi|15042946|ref|NM_021338.2|[15042946]
Y16430 - mRNA for ribosomal protein L35a
gi|15024263|emb|Y16430.2|MMY16430[15024263]
AF043285 - ribosomal protein S7 (rpS7) gene, complete cds
gi|2811283|gb|AF043285.1|AF043285[2811283]
BC010721 - ribosomal protein S3, clone MGC: 6565 IMAGE: 2811930, mRNA, complete cds
gi|14715106|gb|BC010721.1|BC010721[14715106]
BC010604 - ribosomal protein S6, clone MGC: 6573 IMAGE: 3481640, mRNA, complete cds
gi|14714896|gb|BC010604.1|BC010604[14714896]
BC009100 - ribosomal protein S4, X-linked, clone MGC: 6575 IMAGE: 3482299, mRNA, complete cds
gi|14318605|gb|BC009100.1|BC009100[14318605]
BC005790 - ribosomal protein L5, clone IMAGE: 2811648, mRNA
gi|14710611|gb|BC005790.1|BC005790[14710611]
BC008223 - ribosomal protein L31, clone MGC: 6449 IMAGE: 2599150, mRNA, complete cds
gi|14198320|gb|BC008223.1|BC008223[14198320]
BC007139 - ribosomal protein L22, clone MGC: 6121 IMAGE: 3487607, mRNA, complete cds
gi|13938045|gb|BC007139.1|BC007139[13938045]
BC003896 - ribosomal protein L17, clone MGC: 6758 IMAGE: 3594373, mRNA, complete cds
gi|13278089|gb|BC003896.1|BC003896[13278089]
BC003829 - laminin receptor 1 (67 kD, ribosomal protein SA), clone MGC: 6243 IMAGE: 3600738, mRNA, complete cds
gi|13277920|gb|BC003829.1|BC003829[13277920]
BC002145 - ribosomal protein S23, clone MGC: 7260 IMAGE: 3484753, mRNA, complete cds
gi|12805350|gb|BC002145.1|BC002145[12805350]
BC002110 - ribosomal protein L24, clone MGC: 6606 IMAGE: 3488279, mRNA, complete cds
gi|12805288|gb|BC002110.1|BC002110[12805288]
BC002088 - ribosomal protein S25, clone MGC: 6338 IMAGE: 3487037, mRNA, complete cds
gi|12805250|gb|BC002088.1|BC002088[12805250]
BC002062 - ribosomal protein L29, clone MGC: 6127 IMAGE: 3590425, mRNA, complete cds
gi|12805206|gb|BC002062.1|BC002062[12805206]
BC002060 - ribosomal protein L30, clone MGC: 6114 IMAGE: 3489311, mRNA, complete cds
gi|12805202|gb|BC002060.1|BC002060[12805202]
BC002044 - ribosomal protein S17, clone MGC: 6030 IMAGE: 3484265, mRNA, complete cds
gi|12805170|gb|BC002044.1|BC002044[12805170]
BC002014 - ribosomal protein S7, clone MGC: 5812 IMAGE: 3484169, mRNA, complete cds
gi|12805114|gb|BC002014.1|BC002014[12805114]
AF374195 - ribosomal protein L6 (Rpl6) gene, complete cds
gi|14210105|gb|AF374195.1|AF374195[14210105]
NM_011292 - ribosomal protein L9 (Rpl9), mRNA
gi|14149646|ref|NM_011292.1|[14149646]
AF227523 - ribosomal protein L3 (Rpl3) gene, partial cds
gi|13383337|gb|AF227523.1|AF227523[13383337]
NM_011289 - ribosomal protein L27 (Rpl27), mRNA
gi|8567399|ref|NM_011289.1|[8567399]
NM_019647 - ribosomal protein L21 (Rpl21), mRNA
gi|9789992|ref|NM_019647.1|[9789992]
NM_011029 - laminin receptor 1 (67 kD, ribosomal protein SA) (Lamr1), mRNA gi|6754967|ref|NM_011029.1|[6754967]
NM_023133 - ribosomal protein S19 (Rps19), mRNA
gi|12963510|ref|NM_023133.1|[12963510]
NM_022891 - ribosomal protein L23 (Rpl23), mRNA
gi|12584985|ref|NM_022891.1|[12584985]
AF287271 - ribosomal protein L23 (Rpl23) mRNA, complete cds
gi|9502281|gb|AF287271.1|AF287271[9502281]
AF158022 - ribosomal protein L23 (Rpl23) gene, complete cds
gi|5354204|gb|AF158022.1|AF158022[5354204]
NM_018853 - ribosomal protein, large, P1 (Rplp1), mRNA
gi|9256518|ref|NM_018853.1|[9256518]
NM_020600 - ribosomal protein S14 (Rps14), mRNA
gi|10181111|ref|NM_020600.1|[10181111]
NM_019865 - ribosomal protein L44 (Rpl44), mRNA
gi|9845294|ref|NM_019865.1|[9845294]
NM_018730 - ribosomal protein L36 (Rpl36), mRNA
gi|9055321|ref|NM_018730.1|[9055321]
NM_016959 - ribosomal protein S3a (Rps3a), mRNA
gi|8394217|ref|NM_016959.1|[8394217]
NM_016738 - ribosomal protein L13 (Rpl13), mRNA
gi|7949126|ref|NM_016738.1|[7949126]
NM_013765 - ribosomal protein S26 (Rps26), mRNA
gi|7305446|ref|NM_013765.1|[7305446]
NM_013647 - ribosomal protein S16 (Rps16), mRNA
gi|7305444|ref|NM_013647.1|[7305444]
NM_013721 - ribosomal protein L7a (Rpl7a), mRNA
gi|7305442|ref|NM_013721.1|[7305442]
NM_013762 - ribosomal protein L3 (Rpl3), mRNA
gi|7305440|ref|NM_013762.1|[7305440]
NM_009438 - ribosomal protein L13a (Rpl13a), mRNA
gi|7110730|ref|NM_009438.1|[7110730]
NM_011300 - ribosomal protein S7 (Rps7), mRNA
gi|6755375|ref|NM_011300.1|[6755375]
NM_012052 - ribosomal protein S3 (Rps3), mRNA
gi|6755371|ref|NM_012052.1|[6755371]
NM_011297 - ribosomal protein S24 (Rps24), mRNA
gi|6755369|ref|NM_011297.1|[6755369]
NM_011296 - ribosomal protein S18 (Rps18), mRNA
gi|6755367|ref|NM_011296.1|[6755367]
NM_011295 - ribosomal protein S12 (Rps12), mRNA
gi|6755365|ref|NM_011295.1|[6755365]
NM_012053 - ribosomal protein L8 (Rpl8), mRNA
gi|6755357|ref|NM_012053.1|[6755357]
NM_011291 - ribosomal protein L7 (Rpl7), mRNA
gi|6755355|ref|NM_011291.1|[6755355]
NM_011290 - ribosomal protein L6 (Rpl6), mRNA
gi|6755353|ref|NM_011290.1|[6755353]
NM_011287 - ribosomal protein L10A (Rpl10a), mRNA
gi|6755349|ref|NM_011287.1|[6755349]
NM_009098 - ribosomal protein S8 (Rps8), mRNA
gi|6677812|ref|NM_009098.1|[6677812]
NM_009096 - ribosomal protein S6 (Rps6), mRNA
gi|6677808|ref|NM_009096.1|[6677808]
NM_009095 - ribosomal protein S5 (Rps5), mRNA
gi|6677806|ref|NM_009095.1|[6677806]
NM_009094 - ribosomal protein S4, X-linked (Rps4x), mRNA
gi|6677804|ref|NM_009094.1|[6677804]
NM_009093 - ribosomal protein S29 (Rps29), mRNA
gi|6677802|ref|NM_009093.1|[6677802]
NM_009092 - ribosomal protein S17 (Rps17), mRNA
gi|6677800|ref|NM_009092.1|[6677800]
NM_009091 - ribosomal protein S15 (Rps15), mRNA
gi|6677798|ref|NM_009091.1|[6677798]
NM_009084 - ribosomal protein L37a (Rpl37a), mRNA
gi|6677784|ref|NM_009084.1|[6677784]
NM_009083 - ribosomal protein L30 (Rpl30), mRNA
gi|6677782|ref|NM_009083.1|[6677782]
NM_009082 - ribosomal protein L29 (Rpl29), mRNA
gi|6677780|ref|NM_009082.1|[6677780]
NM_009081 - ribosomal protein L28 (Rpl28), mRNA
gi|6677778|ref|NM_009081.1|[6677778]
NM_009080 - ribosomal protein L26 (Rpl26), mRNA
gi|6677776|ref|NM_009080.1|[6677776]
NM_009079 - ribosomal protein L22 (Rpl22), mRNA
gi|6677774|ref|NM_009079.1|[6677774]
NM_009078 - ribosomal protein L19 (Rpl19), mRNA
gi|6677772|ref|NM_009078.1|[6677772]
NM_009077 - ribosomal protein L18 (Rpl18), mRNA
gi|6677770|ref|NM_009077.1|[6677770]
NM_009076 - ribosomal protein L12 (Rpl12), mRNA
gi|6677768|ref|NM_009076.1|[6677768]
Y12431 - mRNA for ribosomal protein S5
gi|3717977|emb|Y12431.1|MMRPS5[3717977]
AF236069 - ribosomal protein L29 gene, complete cds
gi|7800211|gb|AF236069.1|AF236069[7800211]
AF283559 - ribosomal protein S2 mRNA, complete cds
gi|10179939|gb|AF283559.1|AF283559[10179939]
AB037665 - rpl38 mRNA for ribosomal protein L38, complete cds
gi|9650959|dbj|AB037665.1|AB037665[9650959]
X83590 - mRNA for ribosomal protein L5, 3'end
gi|619503|emb|X83590.1|MMRPL5[619503]

TABLE 2-continued

Mouse Ribosomal Proteins

AF260271 - 60S ribosomal Protein L9 mRNA, complete cds
gi|7862171|gb|AF260271.1|AF260271[7862171]
AF216207 - ribosomal protein S19 (Rps19) gene, complete cds
gi|7648817|gb|AF216207.1|AF216207[7648817]
AF214527 - ribosomal protein L27 (RPL27) mRNA, complete cds
gi|6708473|gb|AF214527.1|AF214527[6708473]
AB020237 - gene for ribosomal protein L27A, complete cds
gi|4760603|dbj|AB020237.1|AB020237[4760603]
AF091511 - ribosomal protein L8 (Rpl8) gene, partial cds
gi|3851578|gb|AF091511.1|AF091511[3851578]
U89419 - strain BALB/c 60S acidic ribosomal protein P0 mRNA,
partial cds gi|3642675|gb|U89419.1|MMU89419[3642675]
U89418 - strain BALB/c ribosomal protein S2 (LLRep3) mRNA,
partial cds gi|3642670|gb|U89418.1|MMU89418[3642670]
U89417 - strain BALB/c ribosomal protein L3 mRNA, partial cds
gi|3642668|gb|U89417.1|MMU89417[3642668]
U89414 - strain BALB/c ribosomal protein S3 mRNA, partial cds
gi|3642662|gb|U89414.1|MMU89414[3642662]
U67771 - ribosomal protein L8 (RPL8) mRNA, complete cds
gi|1527177|gb|U67771.1|MMU67771[1527177]
K02060 - ribosomal protein L32-3A (3A) gene, complete cds
gi|3228365|gb|K02060.1|MUSRPL3A[3228365]
Y08307 - mRNA for ribosomal protein S14
gi|1565267|emb|Y08307.1|MMMRPS14[1565267]
U78085 - ribosomal protein S5 mRNA, complete cds
gi|1685070|gb|U78085.1|MMU78085[1685070]
D25213 - rpS17 mRNA for ribosomal protein S17, complete cds
gi|893394|dbj|D25213.1|MUSRPS17[893394]
U93864 - ribosomal protein S11 mRNA, complete cds
gi|1938405|gb|U93864.1|MMU93864[1938405]
U93863 - ribosomal protein L21 mRNA, complete cds
gi|1938403|gb|U93863.1|MMU93863[1938403]
U93862 - ribosomal protein L41 mRNA, complete cds
gi|1938401|gb|U93862.1|MMU93862[1938401]
M62952 - ribosomal protein L19, complete cds
gi|198642|gb|M62952.1|MUSL19RP[198642]
L31609 - clone mcori-1ck9, S29 ribosomal protein mRNA, complete cds
gi|1220417|gb|L31609.1|MUSS29RP[1220417]
U67770 - ribosomal protein S26 (RPS26) mRNA, complete cds
gi|1527175|gb|U67770.1|MMU67770[1527175]
X54067 - SURF-3 gene for ribosomal protein L7a (rpL7a)
gi|54209|emb|X54067.1|MMSURF3[54209]
Z32550 - gene for ribosomal protein L35a
gi|563529|emb|Z32550.1|MMRPL35[563529]
X73829 - mRNA for ribosomal protein S8
gi|313297|emb|X73829.1|MMRPS8[313297]
X73331 - mRNA for ribosomal protein L37a
gi|312413|emb|X73331.1|MMRP37A[312413]
X60289 - mRNA for ribosomal protein S24
gi|311296|emb|X60289.1|MMRPS24[311296]
Y00348 - mRNA for ribosomal protein S6
gi|54009|emb|Y00348.1|MMRPS6[54009]
X15962 - mRNA for ribosomal protein S12
gi|54005|emb|X15962.1|MMRPS12[54005]
X74856 - L28 mRNA for ribosomal protein L28
gi|488834|emb|X74856.1|MMRNAL28[488834]
X76772 - mRNA for ribosomal protein S3
gi|439521|emb|X76772.1|MMRIBPS3[439521]
X57960 - mRNA for ribosomal protein L7
gi|53911|emb|X57960.1|MMRBPRL7A[53911]
X57961 - mRNA for ribosomal protein L7
gi|55488|emb|X57961.1|MRBPRL7B[55488]
X75895 - mRNA for ribosomal protein L36
gi|443801|emb|X75895.1|MML36[443801]
U28917 - 60S ribosomal protein (A52) mRNA, complete cds
gi|899444|gb|U28917.1|MMU28917[899444]
M73436 - ribosomal protein S4 (Rps4) mRNA, complete CDS
gi|200863|gb|M73436.1|MUSRSP4[200863]
L24371 - clone FVB41, ribosomal protein S4 gene, partial cds
gi|402310|gb|L24371.1|MUSRPS4B[402310]
M77296 - ribosomal protein S4 (Rps4) gene, partial cds
gi|200798|gb|M77296.1|MUSRPS4A[200798]
M29016 - ribosomal protein L7 (rpL7) mRNA, 5' end
gi|200786|gb|M29016.1|MUSRPS7R[200786]
M29015 - ribosomal protein L7 (rpL7) gene, complete cds
gi|200784|gb|M29015.1|MUSRPL7A[200784]
M23453 - ribosomal protein L32' (rpL32') gene, complete cds
gi|200778|gb|M23453.1|MUSRPL32A[200778]

TABLE 2-continued

Mouse Ribosomal Proteins

L04128 - ribosomal protein L18 (rpL18) mRNA, complete cds
gi|398049|gb|L04128.1|MUSRPL18A[398049]
L04280 - ribosomal protein (Rpl12) mRNA, complete cds
gi|398047|gb|L04280.1|MUSRPL12A[398047]
M35397 - ribosomal protein L32' (L32') gene, complete cds
gi|200773|gb|M35397.1|MUSRP32A[200773]
M85235 - ribosomal protein mRNA, complete cds
gi|200769|gb|M85235.1|MUSRP[200769]
U11248 - C57BL/6J ribosomal protein S28 mRNA, complete cds
gi|508265|gb|U11248.1|MMU11248[508265]
M76762 - ribosomal protein (Ke-3) gene, exons 1 to 5, and complete cds
gi|198577|gb|M76762.1|MUSKE3A[198577]
M76763 - ribosomal protein (Ke-3) mRNA, complete cds
gi|198579|gb|M76763.1|MUSKE3B[198579]
M11408 - S16 ribosomal protein gene, complete cds
gi|435544|gb|M11408.1|MUSRPS16[435544]
K02928 - ribosomal protein L30 gene, complete cds
gi|435126|gb|K02928.1|MUSRPL30[435126]

TABLE 3

Human Ribosomal Proteins

NM_000994 - ribosomal protein L32 (RPL32), mRNA
gi|15812220|ref|NM_000994.2|[15812220]
NM_000993 - ribosomal protein L31 (RPL31), mRNA
gi|15812219|ref|NM_000993.2|[15812219]
NM_000989 - ribosomal protein L30 (RPL30), mRNA
gi|15812218|ref|NM_000989.2|[15812218]
NM_001006 - ribosomal protein S3A (RPS3A), mRNA
gi|15718688|ref|NM_001006.2|[15718688]
NM_001005 - ribosomal protein S3 (RPS3), mRNA
gi|15718686|ref|NM_001005.2|[15718686]
NM_006013 - ribosomal protein L10 (RPL10), mRNA
gi|15718685|ref|NM_006013.2|[15718685]
NM_002954 - ribosomal protein S27a (RPS27A), mRNA
gi|15431307|ref|NM_002954.2|[15431307]
NM_001011 - ribosomal protein S7 (RPS7), mRNA
gi|15431308|ref|NM_001011.2|[15431308]
NM_033301 - ribosomal protein L8 (RPL8), transcript variant 2, mRNA
gi|15431305|ref|NM_033301.1|[15431305]
NM_000973 - ribosomal protein L8 (RPL8), transcript variant 1, mRNA
gi|15431304|ref|NM_000973.2|[15431304]
NM_000661 - ribosomal protein L9 (RPL9), mRNA
gi|15431302|ref|NM_000661.2|[15431302]
NM_000971 - ribosomal protein L7 (RPL7), mRNA
gi|15431300|ref|NM_000971.2|[15431300]
NM_000980 - ribosomal protein L18a (RPL18A), mRNA
gi|15431299|ref|NM_000980.2|[15431299]
NM_000979 - ribosomal protein L18 (RPL18), mRNA
gi|15431298|ref|NM_000979.2|[15431298]
NM_000977 - ribosomal protein L13 (RPL13), transcript variant 1,
mRNA gi|15431296|ref|NM_000977.2|[15431296]
NM_033251 - ribosomal protein L13 (RPL13), transcript variant 2,
mRNA gi|15431294|ref|NM_033251.1|[15431294]
NM_002948 - ribosomal protein L15 (RPL15), mRNA
gi|15431292|ref|NM_002948.2|[15431292]
NM_000976 - ribosomal protein L12 (RPL12), mRNA
gi|15431291|ref|NM_000976.2|[15431291]
NM_000975 - ribosomal protein L11 (RPL11), mRNA
gi|15431289|ref|NM_000975.2|[15431289]
NM_007104 - ribosomal protein L10a (RPL10A), mRNA
gi|15431287|ref|NM_007104.3|[15431287]
NM_032241 - ribosomal protein L10 (RPL10), mRNA
gi|14149953|ref|NM_032241.1|[14149953]
NM_001012 - ribosomal protein S8 (RPS8), mRNA
gi|4506742|ref|NM_001012.1|[4506742]
XM_012407 - ribosomal protein L9 (RPL9), mRNA
gi|15321503|ref|XM_012407.4|[15321503]
XM_053465 - ribosomal protein L9 (RPL9), mRNA
gi|15321501|ref|XM_053465.1|[15321501]
XM_053100 - ribosomal protein L13 (RPL13), mRNA
gi|15317414|ref|XM_053100.1|[15317414]
XM_051496 - ribosomal protein S25 (RPS25), mRNA
gi|15314558|ref|XM_051496.2|[15314558]

TABLE 3-continued

Human Ribosomal Proteins

XM_039216 - ribosomal protein S13 (RPS13), mRNA
gi|15313667|ref|XM_039216.2|[15313667]
XM_047576 - ribosomal protein S15 (RPS15), mRNA
gi|15309638|ref|XM_047576.2|[15309638]
XM_028963 - ribosomal protein L23 (RPL23), mRNA
gi|15309255|ref|XM_028963.2|[15309255]
XM_006026 - ribosomal protein S28 (RPS28), mRNA
gi|15309243|ref|XM_006026.5|[15309243]
XM_030050 - ribosomal protein L17 (RPL17), mRNA
gi|15306618|ref|XM_030050.2|[15306618]
XM_053077 - ribosomal protein S16 (RPS16), mRNA
gi|15306479|ref|XM_053077.1|[15306479]
XM_016662 - ribosomal protein L38 (RPL38), mRNA
gi|14785533|ref|XM_016662.2|[14785533]
XM_034464 - ribosomal protein S2 (RPS2), mRNA
gi|14779902|ref|XM_034464.1|[14779902]
XM_007920 - ribosomal protein L3-like (RPL3L), mRNA
gi|14779893|ref|XM_007920.4|[14779893]
XM_009998 - ribosomal protein L3 (RPL3), mRNA
gi|14779001|ref|XM_009998.4|[14779001]
XM_039345 - ribosomal protein L3 (RPL3), mRNA
gi|14778998|ref|XM_039345.1|[14778998]
XM_039344 - ribosomal protein L3 (RPL3), mRNA
gi|14778996|ref|XM_039344.1|[14778996]
XM_039346 - ribosomal protein L3 (RPL3), mRNA
gi|14778994|ref|XM_039346.1|[14778994]
XM_047467 - ribosomal protein L13 (RPL13), mRNA
gi|14776722|ref|XM_047467.1|[14776722]
XM_047464 - ribosomal protein L13 (RPL13), mRNA
gi|14776717|ref|XM_047464.1|[14776717]
XM_047468 - ribosomal protein L13 (RPL13), mRNA
gi|14776715|ref|XM_047468.1|[14776715]
XM_047465 - ribosomal protein L13 (RPL13), mRNA
gi|14776711|ref|XM_047465.1|[14776711]
XM_027368 - ribosomal protein S15a (RPS15A), mRNA
gi|14774916|ref|XM_027368.1|[14774916]
XM_027367 - ribosomal protein S15a (RPS15A), mRNA
gi|14774912|ref|XM_027367.1|[14774912]
XM_044693 - ribosomal protein L26 (RPL26), mRNA
gi|14774237|ref|XM_044693.1|[14774237]
XM_051497 - ribosomal protein S25 (RPS25), mRNA
gi|14774084|ref|XM_051497.1|[14774084]
XM_039215 - ribosomal protein S13 (RPS13), mRNA
gi|14772983|ref|XM_039215.1|[14772983]
XM_032124 - ribosomal protein L27 (RPL27), mRNA
gi|14772981|ref|XM_032124.1|[14772981]
XM_008208 - ribosomal protein L27 (RPL27), mRNA
gi|14772978|ref|XM_008208.4|[14772978]
XM_006388 - ribosomal protein S13 (RPS13), mRNA
gi|14772975|ref|XM_006388.5|[14772975]
XM_050589 - ribosomal protein S9 (RPS9), mRNA
gi|14769524|ref|XM_050589.1|[14769524]
XM_048412 - region containing hypothetical protein FLJ23544;
ribosomal protein L10; ribosomal protein L10; ribosomal protein L10
(LOC88324), mRNA gi|14768370|ref|XM_048412.1|[14768370]
XM_048415 - region containing hypothetical protein FLJ23544;
ribosomal protein L10; ribosomal protein L10; ribosomal protein L10
(LOC88324), mRNA gi|14768366|ref|XM_048415.1|[14768366]
XM_038593 - ribosomal protein L18a (RPL18A), mRNA
gi|14766237|ref|XM_038593.1|[14766237]
XM_045500 - Finkel-Biskis-Reilly murine sarcoma virus (FBR-MuSV)
ubiquitously expressed (fox derived); ribosomal protein S30 (FAU),
mRNA gi|14765886|ref|XM_045500.1|[14765886]
XM_006522 - Finkel-Biskis-Reilly murine sarcoma virus (FBR-MuSV)
ubiquitously expressed (fox derived); ribosomal protein S30 (FAU),
mRNA gi|14765881|ref|XM_006522.4|[14765881]
XM_046112 - ribosomal protein S16 (RPS16), mRNA
gi|14764309|ref|XM_046112.1|[14764309]
XM_017838 - ribosomal protein L27a (RPL27A), mRNA
gi|14763277|ref|XM_017838.2|[14763277]
XM_044022 - ribosomal protein S4, X-linked (RPS4X), mRNA
gi|14758953|ref|XM_044022.1|[14758953]
XM_044024 - ribosomal protein S4, X-linked (RPS4X), mRNA
gi|14758950|ref|XM_044024.1|[14758950]
XM_044025 - ribosomal protein S4, X-linked (RPS4X), mRNA
gi|14758939|ref|XM_044025.1|[14758939]
XM_050942 - ribosomal protein L6 (RPL6), mRNA
gi|14758187|ref|XM_050942.1|[14758187]

TABLE 3-continued

Human Ribosomal Proteins

XM_050943 - ribosomal protein L6 (RPL6), mRNA
gi|14758163|ref|XM_050943.1|[14758163]
XM_016828 - ribosomal protein L44 (RPL44), mRNA
gi|14757899|ref|XM_016828.2|[14757899]
XM_035105 - ribosomal protein L7a (RPL7A), mRNA
gi|14735036|ref|XM_035105.1|[14735036]
XM_016869 - ribosomal protein L26 homolog (LOC51121), mRNA
gi|14723097|ref|XM_016869.2|[14723097]
XM_016124 - ribosomal protein L39 (RPL39), mRNA
gi|13651332|ref|XM_016124.1|[13651332]
XM_018114 - region containing hypothetical protein FLJ23544;
ribosomal protein L10; ribosomal protein L10; ribosomal protein L10
(LOC88324), mRNA gi|13649125|ref|XM_018114.1|[13649125]
XM_008294 - ribosomal protein L19 (RPL19), mRNA
gi|13632268|ref|XM_008294.3|[13632268]
XM_009693 - ribosomal protein S21 (RPS21), mRNA
gi|15304527|ref|XM_009693.3|[15304527]
XM_053478 - ribosomal protein L10a (RPL10A), mRNA
gi|15303249|ref|XM_053478.1|[15303249]
XM_015318 - ribosomal protein S26 (RPS26), mRNA
gi|15303043|ref|XM_015318.2|[15303043]
XM_027885 - ribosomal protein L13a (RPL13A), mRNA
gi|15302570|ref|XM_027885.2|[15302570]
XM_007615 - ribosomal protein S17 (RPS17), mRNA
gi|15302513|ref|XM_007615.4|[15302513]
XM_054333 - ribosomal protein L28 (RPL28), mRNA
gi|15302226|ref|XM_054333.1|[15302226]
XM_031815 - ribosomal protein S20 (RPS20), mRNA
gi|15300059|ref|XM_031815.2|[15300059]
XM_039576 - ribosomal protein S24 (RPS24), mRNA
gi|15299342|ref|XM_039576.2|[15299342]
XM_004020 - ribosomal protein S23 (RPS23), mRNA
gi|15297223|ref|XM_004020.2|[15297223]
XM_053824 - ribosomal protein L32 (RPL32), mRNA
gi|15296504|ref|XM_053824.1|[15296504]
XM_054368 - ribosomal protein L11 (RPL11), mRNA
gi|15296209|ref|XM_054368.1|[15296209]
XM_036739 - ribosomal protein S27 (metallopanstimulin 1) (RPS27),
mRNA gi|15294821|ref|XM_036739.2|[15294821]
XM_027332 - ribosomal protein L36 (RPL36), mRNA
gi|14786075|ref|XM_027332.1|[14786075]
XM_027331 - ribosomal protein L36 (RPL36), mRNA
gi|14786072|ref|XM_027331.1|[14786072]
XM_027333 - ribosomal protein L36 (RPL36), mRNA
gi|14786069|ref|XM_027333.1|[14786069]
XM_046140 - 60S ribosomal protein L30 isolog (LOC51187), mRNA
gi|14785520|ref|XM_046140.1|[14785520]
XM_046136 - 60S ribosomal protein L30 isolog (LOC51187), mRNA
gi|14785516|ref|XM_046136.1|[14785516]
XM_043287 - ribosomal protein S10 (RPS10), mRNA
gi|14782916|ref|XM_043287.1|[14782916]
XM_043285 - ribosomal protein S10 (RPS10), mRNA
gi|14782914|ref|XM_043285.1|[14782914]
XM_049965 - ribosomal protein L18 (RPL18), mRNA
gi|14760401|ref|XM_049965.1|[14760401]
XM_049096 - ribosomal protein S26 (RPS26), mRNA
gi|14759881|ref|XM_049096.1|[14759881]
XM_015328 - ribosomal protein L41 (RPL41), mRNA
gi|14759754|ref|XM_015328.2|[14759754]
XM_008923 - ribosomal protein S11 (RPS11), mRNA
gi|14757439|ref|XM_008923.4|[14757439]
XM_027884 - ribosomal protein L13a (RPL13A), mRNA
gi|14757411|ref|XM_027884.1|[14757411]
XM_027886 - ribosomal protein L13a (RPL13A), mRNA
gi|14757404|ref|XM_027886.1|[14757404]
XM_035924 - ribosomal protein L28 (RPL28), mRNA
gi|14757079|ref|XM_035924.1|[14757079]
XM_017626 - ribosomal protein S12 (RPS12), mRNA
gi|14756487|ref|XM_017626.2|[14756487]
XM_029926 - ribosomal protein S19 (RPS19), mRNA
gi|14756213|ref|XM_029926.1|[14756213]
XM_034265 - ribosomal protein S5 (RPS5), mRNA
gi|14755544|ref|XM_034265.1|[14755544]
XM_029544 - 40S ribosomal protein S27 isoform (LOC51065), mRNA
gi|14752644|ref|XM_029544.1|[14752644]
XM_035389 - ribosomal protein, large, P1 (RPLP1), mRNA
gi|14749908|ref|XM_035389.1|[14749908]
XM_035388 - ribosomal protein, large, P1 (RPLP1), mRNA

TABLE 3-continued

Human Ribosomal Proteins gi|14749900|ref|XM_035388.1|[14749900]
XM_035387 - ribosomal protein, large, P1 (RPLP1), mRNA
gi|14749891|ref|XM_035387.1|[14749891]
XM_035494 - ribosomal protein L7 (RPL7), mRNA
gi|14749839|ref|XM_035494.1|[14749839]
XM_035493 - ribosomal protein L7 (RPL7), mRNA
gi|14749837|ref|XM_035493.1|[14749837]
XM_035492 - ribosomal protein L7 (RPL7), mRNA
gi|14749834|ref|XM_035492.1|[14749834]
XM_052447 - ribosomal protein L29 (RPL29), mRNA
gi|14747560|ref|XM_052447.1|[14747560]
XM_052669 - ribosomal protein S29 (RPS29), mRNA
gi|14747175|ref|XM_052669.1|[14747175]
XM_044796 - ribosomal protein L35 (RPL35), mRNA
gi|14744218|ref|XM_044796.1|[14744218]
XM_039575 - ribosomal protein S24 (RPS24), mRNA
gi|14743725|ref|XM_039575.1|[14743725]
XM_039577 - ribosomal protein S24 (RPS24), mRNA
gi|14743718|ref|XM_039577.1|[14743718]
XM_039578 - ribosomal protein S24 (RPS24), mRNA
gi|14743713|ref|XM_039578.1|[14743713]
XM_046554 - ribosomal protein S8 (RPS8), mRNA
gi|14742855|ref|XM_046554.1|[14742855]
XM_034712 - ribosomal protein L34 (RPL34), mRNA
gi|14734144|ref|XM_034712.1|[14734144]
XM_034711 - ribosomal protein L34 (RPL34), mRNA
gi|14734139|ref|XM_034711.1|[14734139]
XM_042550 - ribosomal protein S14 (RPS14), mRNA
gi|14734089|ref|XM_042550.1|[14734089]
XM_042549 - ribosomal protein S14 (RPS14), mRNA
gi|14734082|ref|XM_042549.1|[14734082]
XM_042548 - ribosomal protein S14 (RPS14), mRNA
gi|14734076|ref|XM_042548.1|[14734076]
XM_015463 - ribosomal protein L24 (RPL24), mRNA
gi|14733795|ref|XM_015463.2|[14733795]
XM_040555 - ribosomal protein L24 (RPL24), mRNA
gi|14733789|ref|XM_040555.1|[14733789]
XM_036365 - ribosomal protein L31 (RPL31), mRNA
gi|14728681|ref|XM_036365.1|[14728681]
XM_017513 - ribosomal protein S27a (RPS27A), mRNA
gi|14725314|ref|XM_017513.2|[14725314]
XM_028344 - ribosomal protein L5 (RPL5), mRNA
gi|14723700|ref|XM_028344.1|[14723700]
XM_018268 - ribosomal protein L15 (RPL15), mRNA
gi|14723418|ref|XM_018268.2|[14723418]
XM_041875 - ribosomal protein L15 (RPL15), mRNA
gi|14723414|ref|XM_041875.1|[14723414]
XM_037459 - ribosomal protein S3A (RPS3A), mRNA
gi|14721867|ref|XM_037459.1|[14721867]
XM_037458 - ribosomal protein S3A (RPS3A), mRNA
gi|14721861|ref|XM_037458.1|[14721861]
XM_037454 - ribosomal protein S3A (RPS3A), mRNA
gi|14721857|ref|XM_037454.1|[14721857]
XM_003054 - ribosomal protein L32 (RPL32), mRNA
gi|13646087|ref|XM_003054.4|[13646087]
XM_016854 - ribosomal protein S18 (RPS18), mRNA
gi|13645838|ref|XM_016854.1|[13645838]
XM_017704 - ribosomal protein L10a (RPL10A), mRNA
gi|13642762|ref|XM_017704.1|[13642762]
XM_017770 - ribosomal protein L37 (RPL37), mRNA
gi|13641596|ref|XM_017770.1|[13641596]
XM_008905 - ribosomal protein L28 (RPL28), mRNA
gi|13630273|ref|XM_008905.3|[13630273]
XM_007281 - ribosomal protein L36a (RPL36A), mRNA
gi|12738346|ref|XM_007281.2|[12738346]
XM_002637 - ribosomal protein L37a (RPL37A), mRNA
gi|11430427|ref|XM_002637.1|[11430427]
XM_010467 - ribosomal protein S4, Y-linked (RPS4Y), mRNA
gi|13640136|ref|XM_010467.3|[13640136]
NM_007209 - ribosomal protein L35 (RPL35), mRNA
gi|6005859|ref|NM_007209.1|[6005859]
NM_002952 - ribosomal protein S2 (RPS2), mRNA
gi|15055538|ref|NM_002952.2|[15055538]
NM_001031 - ribosomal protein S28 (RPS28), mRNA
gi|15011938|ref|NM_001031.2|[15011938]
NM_001030 - ribosomal protein S27 (metallopanstimulin 1) (RPS27), mRNA gi|15011937|ref|NM_001030.2|[15011937]
NM_001029 - ribosomal protein S26 (RPS26), mRNA gi|15011935|ref|NM_001029.2|[15011935]
NM_001026 - ribosomal protein S24 (RPS24), transcript variant 2, mRNA gi|14916502|ref|NM_001026.2|[14916502]
NM_033022 - ribosomal protein S24 (RPS24), transcript variant 1, mRNA gi|14916500|ref|NM_033022.1|[14916500]
NM_001025 - ribosomal protein S23 (RPS23), mRNA gi|14790142|ref|NM_001025.2|[14790142]
NM_016093 - ribosomal protein L26 homolog (LOC51121), mRNA gi|7705812|ref|NM_016093.1|[7705812]
NM_015414 - ribosomal protein L36 (RPL36), mRNA gi|7661637|ref|NM_015414.1|[7661637]
NM_000988 - ribosomal protein L27 (RPL27), mRNA gi|4506622|ref|NM_000988.1|[4506622]
NM_000986 - ribosomal protein L24 (RPL24), mRNA gi|4506618|ref|NM_000986.1|[4506618]
NM_003973 - ribosomal protein L14 (RPL14), mRNA gi|4506600|ref|NM_003973.1|[4506600]
NM_001024 - ribosomal protein S21 (RPS21), mRNA gi|14670385|ref|NM_001024.2|[14670385]
NM_001028 - ribosomal protein S25 (RPS25), mRNA gi|14591916|ref|NM_001028.2|[14591916]
NM_001023 - ribosomal protein S20 (RPS20), mRNA gi|14591915|ref|NM_001023.2|[14591915]
NM_001022 - ribosomal protein S19 (RPS19), mRNA gi|14591914|ref|NM_001022.2|[14591914]
NM_001021 - ribosomal protein S17 (RPS17), mRNA gi|14591913|ref|NM_001021.2|[14591913]
NM_001020 - ribosomal protein S16 (RPS16), mRNA gi|14591912|ref|NM_001020.2|[14591912]
NM_001018 - ribosomal protein S15 (RPS15), mRNA gi|14591911|ref|NM_001018.2|[14591911]
NM_001017 - ribosomal protein S13 (RPS13), mRNA gi|14591910|ref|NM_001017.2|[14591910]
NM_000969 - ribosomal protein L5 (RPL5), mRNA gi|14591908|ref|NM_000969.2|[14591908]
NM_000978 - ribosomal protein L23 (RPL23), mRNA gi|14591907|ref|NM_000978.2|[14591907]
NM_000985 - ribosomal protein L17 (RPL17), mRNA gi|14591906|ref|NM_000985.2|[14591906]
NM_012423 - ribosomal protein L13a (RPL13A), mRNA gi|14591905|ref|NM_012423.2|[14591905]
NM_001016 - ribosomal protein S12 (RPS12), mRNA gi|14277699|ref|NM_001016.2|[14277699]
NM_001015 - ribosomal protein S11 (RPS11), mRNA gi|14277698|ref|NM_001015.2|[14277698]
NM_001019 - ribosomal protein S15a (RPS15A), mRNA gi|14165468|ref|NM_001019.2|[14165468]
NM_022551 - ribosomal protein S18 (RPS18), mRNA gi|14165467|ref|NM_022551.2|[14165467]
NM_001013 - ribosomal protein S9 (RPS9), mRNA gi|14141192|ref|NM_001013.2|[14141192]
NM_005617 - ribosomal protein S14 (RPS14), mRNA gi|14141191|ref|NM_005617.2|[14141191]
NM_000990 - ribosomal protein L27a (RPL27A), mRNA gi|14141189|ref|NM_000990.2|[14141189]
NM_001009 - ribosomal protein S5 (RPS5), mRNA gi|13904869|ref|NM_001009.2|[13904869]
NM_001032 - ribosomal protein S29 (RPS29), mRNA gi|13904868|ref|NM_001032.2|[13904868]
NM_001014 - ribosomal protein S10 (RPS10), mRNA gi|13904867|ref|NM_001014.2|[13904867]
NM_000991 - ribosomal protein L28 (RPL28), mRNA gi|13904865|ref|NM_000991.2|[13904865]
NM_000995 - ribosomal protein L34 (RPL34), mRNA gi|4506636|ref|NM_000995.1|[4506636]
NM_001997 - Finkel-Biskis-Reilly murine sarcoma virus (FBR-MuSV) ubiquitously expressed (fox derived); ribosomal protein S30 (FAU), mRNA gi|4503658|ref|NM_001997.1|[4503658]
NM_022061 - ribosomal protein L17 isolog (LOC63875), mRNA gi|11596858|ref|NM_022061.1|[11596858]
NM_021104 - ribosomal protein L41 (RPL41), mRNA gi|10863874|ref|NM_021104.1|[10863874]
NM_021029 - ribosomal protein L44 (RPL44), mRNA gi|10445222|ref|NM_021029.1|[10445222]
NM_016304 - 60S ribosomal protein L30 isolog (LOC51187), mRNA gi|10047101|ref|NM_016304.1|[10047101]
NM_002295 - laminin receptor 1 (67 kD, ribosomal protein SA) (LAMR1), mRNA gi|9845501|ref|NM_002295.2|[9845501]

TABLE 3-continued

Human Ribosomal Proteins

NM_016183 - 60S acidic ribosomal protein PO (LOC51154), mRNA
gi|7705874|ref|NM_016183.1|[7705874]
NM_015971 - 30S ribosomal protein S7 homolog (LOC51081), mRNA
gi|7705737|ref|NM_015971.1|[7705737]
NM_015920 - 40S ribosomal protein S27 isoform (LOC51065), mRNA
gi|7705705|ref|NM_015920.1|[7705705]
NM_005061 - ribosomal protein L3-like (RPL3L), mRNA
gi|4826987|ref|NM_005061.1|[4826987]
NM_001010 - ribosomal protein S6 (RPS6), mRNA
gi|4506730|ref|NM_001010.1|[4506730]
NM_001008 - ribosomal protein S4, Y-linked (RPS4Y), mRNA
gi|4506726|ref|NM_001008.1|[4506726]
NM_001007 - ribosomal protein S4, X-linked (RPS4X), mRNA
gi|4506724|ref|NM_001007.1|[4506724]
NM_001004 - ribosomal protein, large P2 (RPLP2), mRNA
gi|4506670|ref|NM_001004.1|[4506670]
NM_001003 - ribosomal protein, large, P1 (RPLP1), mRNA
gi|4506668|ref|NM_001003.1|[4506668]
NM_001002 - ribosomal protein, large, P0 (RPLP0), mRNA
gi|4506666|ref|NM_001002.1|[4506666]
NM_000972 - ribosomal protein L7a (RPL7A), mRNA
gi|4506660|ref|NM_000972.1|[4506660]
NM_000970 - ribosomal protein L6 (RPL6), mRNA
gi|4506656|ref|NM_000970.1|[4506656]
NM_000968 - ribosomal protein L4 (RPL4), mRNA
gi|4506652|ref|NM_000968.1|[4506652]
NM_001001 - ribosomal protein L36a (RPL36A), mRNA
gi|4506650|ref|NM_001001.1|[4506650]
NM_000967 - ribosomal protein L3 (RPL3), mRNA
gi|4506648|ref|NM_000967.1|[4506648]
NM_001000 - ribosomal protein L39 (RPL39), mRNA
gi|4506646|ref|NM_001000.1|[4506646]
NM_000999 - ribosomal protein L38 (RPL38), mRNA
gi|4506644|ref|NM_000999.1|[4506644]
NM_000998 - ribosomal protein L37a (RPL37A), mRNA
gi|4506642|ref|NM_000998.1|[4506642]
NM_000997 - ribosomal protein L37 (RPL37), mRNA
gi|4506640|ref|NM_000997.1|[4506640]
NM_000996 - ribosomal protein L35a (RPL35A), mRNA
gi|4506638|ref|NM_000996.1|[4506638]
NM_000992 - ribosomal protein L29 (RPL29), mRNA
gi|4506628|ref|NM_000992.1|[4506628]
NM_000987 - ribosomal protein L26 (RPL26), mRNA
gi|4506620|ref|NM_000987.1|[4506620]
NM_000984 - ribosomal protein L23a (RPL23A), mRNA
gi|4506614|ref|NM_000984.1|[4506614]
NM_000983 - ribosomal protein L22 (RPL22), mRNA
gi|4506612|ref|NM_000983.1|[4506612]
NM_000982 - ribosomal protein L21 (gene or pseudogene) (RPL21), mRNA gi|4506610|ref|NM_000982.1|[4506610]
NM_000981 - ribosomal protein L19 (RPL19), mRNA
gi|4506608|ref|NM_000981.1|[4506608]

All of the sequences in Tables 2 and 3 are incorporated by reference in their entirety.

In preferred embodiments, the tagged ribosomal proteins are S6 or L37 ribosomal proteins, more preferably tagged with a Strep Tag peptide tag, most preferably with the peptide tag at the C-terminus. In another preferred embodiment, the mRNA binding protein is not polyA binding protein.

5.3. Isolation of Ribosomes

Various methods exist to isolate ribosomes, particularly polysomes, from cultured cells and tissues from transformed organisms (see, e.g., Bommer et al., 1997, Isolation and characterization of eukaryotic polysomes, in *Subcellular Fractionation*, Graham and Rickwood (eds.), IRL Press, Oxford, pp. 280-285; incorporated herein by reference in its entirety). Preferably, the isolation method employed has the following characteristics:

(1) Translation arresting compounds, such as emetine or cycloheximide, are added to arrest translation, if possible, as a pre-treatment even before homogenization. This prevents ribosome run-off and keeps the ribosome-mRNA complex stable, i.e., the ribosome remains bound to the mRNA.

(2) RNase inhibitors such as SUPERase•In™ RNase Inhibitor (Ambion, Austin, Tex.) are added to buffers to maintain the integrity of the mRNA.

(3) After tissue or cell homogenization, total polysomes are isolated by preparing a post-mitochondrial supernatant in the presence of at least a high concentration salt buffer, e.g., 100-150 mM KCl.

(4) Detergent is also added to the post-mitochondrial supernatant to release membrane-associated polysomes from endoplasmic reticulum membranes; total polysomes are usually collected by centrifugation through a sucrose cushion.

In certain embodiments, a variation of the above-described general method is used to isolate membrane-associated polysomes from a total pool of polysomes. This allows one to focus on the mRNA species encoding secreted or transmembrane proteins, which are often targets of choice for drug discovery. Various methods may be used to isolate membrane-associated polysomes from cultured cells and tissue, e.g., methods that employ differential centrifugation (Hall C, Lim L. Developmental changes in the composition of poly-adenylated RNA isolated from free and membrane-bound polyribosomes of the rat forebrain, analysed by translation in vitro. Biochem J. 1981 Apr. 15; 196(1):327-36), rate-zonal centrifugation (Rademacher and Steele, 1986, Isolation of undegraded free and membrane-bound polysomal mRNA from rat brain, J. Neurochem. 47(3):953-957), isopycnic centrifugation (Mechler, 1987, Isolation of messenger RNA from membrane-bound polysomes, Methods Enzymol. 152: 241-248), and differential extraction (Bommer et al., 1997, Isolation and characterization of eukaryotic polysomes, in *Subcellular Fractionation*, Graham and Rickwood (eds.), IRL Press, Oxford, pp. 280-285; incorporated herein by reference in its entirety) to isolate the membrane-associated polysomes.

Other appropriate cell lysates or fractions may be obtained using routine biochemical methods.

Specific polysomes can also be isolated using affinity separation techniques targeting nascent polypeptides or endogenous or tagged mRNA-binding proteins using art-known methods e.g., using the methods of Lynch, 1987, Meth. Enzymol. 152: 248-253, and Brooks and Rigby, 2000, Nucleic Acids Res. 28(10): e49.

In certain embodiments, polysomes are not isolated from the post-mitochondrial supernatant or even from a cell or tissue lysate before being subject to affinity purification.

Once the cell lysate or fraction is obtained, the tagged ribosomes may be isolated using routine methods from untagged ribosomes and other cell components, preferably isolated from RNA, most preferably isolated from mRNA, that is not bound to molecularly tagged ribosomes or tagged mRNA binding protein, using affinity reagents that bind the tag specifically.

In a preferred embodiment, the ribosomes are isolated from transfected cells by scraping them into homogenization buffer (50 mM sucrose, 200 mM ammonium chloride, 7 mM magnesium acetate, 1 mM dithiothreitol, and 20 mM Tris-HCl, pH 7.6). The cells are then lysed by the addition of the detergent, NP-40 (Nonidet P40, CALBIOCHEM-NOVABIOCHEM Corporation, San Diego, Calif.) to a concentration of 0.5% followed by five strokes in a glass dounce tissue homogenizer. Unlysed cells, nuclei and mitochondria are pelleted by centrifugation at 10,000×g for 10 minutes, at 4° C. The supernatant is removed and layered over a two-step discontinuous gradient of 1.8 M and 1.0M sucrose in 100 mM ammonium chloride, 5 mM magnesium acetate, 1 mM dithiothreitol, 20 mM Tris-HCl (pH 7.6). The gradient is centrifuged for 18 hours at 98,000×g at 4° C.

Following centrifugation, the supernatants are removed, and the polysome pellet is resuspended in 100 mM ammonium chloride, 5 mM magnesium chloride, 1 mM DTT and 20 mM Tris-HCl (pH 7.6).

An equal volume of 2× denaturing protein electrophoresis sample buffer is added to the polysome sample. Solubilized polysomal proteins are fractionated by electrophoresis through a SDS containing 4-20% gradient polyacrylamide gel, and transferred to a nitrocellulose filter.

The isolation of tagged polysomes directly from crude or post-mitochondrial supernatants (adjusted appropriately with NaCl and detergent) is also envisioned. In certain embodiments, molecular tagging is achieved through the introduction of amino acids into a ribosomal protein-encoding gene such that the amino acids form a polypeptide region (i.e., a tag) that is capable of acting as a receptor or ligand for an affinity separation.

Because nascent polypeptides are attached to isolated monosomes and polysomes, the methods of the invention can also be used to isolate newly synthesized polypeptides from a cell type of interest (e.g., for proteomic applications).

Tagged polysomes that contain specific mRNAs (see infra) are isolated using antibodies that recognize specific nascent, encoded polypeptide chains (for review see Lynch D C. Use of antibodies to obtain specific polysomes. Methods Enzymol. 1987; 152:248-53; Schutz G, Kieval S, Groner B, Sippel A E, Kurtz D, Feigelson P. Isolation of specific messenger RNA by adsorption of polysomes to matrix-bound antibody. Nucleic Acids Res. 1977 January; 4(1):71-84; and Shapiro S Z, Young J R. An immunochemical method for mRNA purification. Application to messenger RNA encoding trypanosome variable surface antigen. J Biol. Chem. 1981 Feb. 25; 256(4):1495-8). Particular mRNA species as low in abundance as 0.01-0.05% of total mRNA have been purified to near homogeneity via this approach.

Affinity methods that can be used to isolate or purify tagged ribosomes or other mRNA binding proteins taking advantage of the affinity of a reagent for the peptide tag are well known in the art including chromatography, solid phase chromatography and precipitation, matrices, precipitation, etc.

In specific embodiments, the invention provides molecularly tagged ribosomes, preferably bound to mRNA, that are bound to an affinity reagent for the molecular tag. In more specific embodiments, the molecularly tagged ribosomes are bound to an affinity reagent that is bound, preferably covalently, to a solid surface, such as a chromatography resin, e.g., agarose, sepharose, and the like.

5.4. Isolation of mRNA from Purified Polysomes

Once the tagged ribosome or mRNA binding protein has been isolated, the associated mRNA complexed with the ribosome or mRNA binding protein may be isolated using methods well known in the art. For example, elution of mRNA is accomplished by addition of EDTA to buffers, which disrupts polysomes and allows isolation of bound mRNA for analysis (Schutz, et al. (1977), Nucl. Acids Res. 4:71-84; Kraus and Rosenberg (1982), Proc. Natl. Acad. Sci. USA 79:4015-4019). In addition, isolated polysomes (attached or detached from isolation matrix) can be directly input into RNA isolation procedures using reagents such as Tri-reagent (Sigma) or Triazol (Sigma). In particular embodiments, poly $A^+$ mRNA is preferentially isolated by virtue of its hybridization of oligodT cellulose. Methods of mRNA isolation are described, for example, in Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties.

5.5. Regulatory Sequences for Expression of Tagged Ribosomes

According to the methods of the invention, the tagged ribosomes are selectively expressed in a particular chosen cell type. Such expression is achieved by driving the expression of the tagged ribosomal protein or mRNA binding protein using regulatory sequences from a gene expressed in the chosen cell type.

The population of cells comprises a discernable group of cells sharing a common characteristic. Because of its selective expression, the population of cells may be characterized or recognized based on its positive expression of the characterizing gene. According to the methods of the invention, some or all of the regulatory sequences may be incorporated into nucleic acids of the invention (including transgenes) to regulate the expression of tagged ribosomal protein or mRNA binding protein coding sequences. In certain embodiments, a gene that is not constitutively expressed, (i.e., exhibits some spatial or temporal restriction in its expression pattern) is used as a source of a regulatory sequence. In other embodiments, a gene that is constitutively expressed is used as a source of a regulatory sequence, for example, when the nucleic acids of the invention are expressed in cultured cells.

In certain embodiments, the expression of tagged ribosomal protein or mRNA binding protein coding sequences is regulated by a non-ribosomal regulatory sequence. Such a sequence may include, but not be limited to, parts of a ribosomal regulatory sequence (but does not include the entire ribosomal regulatory sequence), but such sequence effects a different expression pattern than the ribosomal regulatory sequence.

Preferably, the regulatory sequence is derived form a human or mouse gene associated with an adrenergic or noradrenergic neurotransmitter pathway, e.g., one of the genes listed in Table 4; a cholinergic neurotransmitter pathway, e.g., one of the genes listed in Table 5; a dopaminergic neurotransmitter pathway, e.g., one of the genes listed in Table 6; a GABAergic neurotransmitter pathway, e.g., one of the genes listed in Table 7; a glutaminergic neurotransmitter pathway, e.g., one of the genes listed in Table 8; a glycinergic neurotransmitter pathway, e.g., one of the genes listed in Table 9; a histaminergic neurotransmitter pathway, e.g., one of the genes listed in Table 10; a neuropeptidergic neurotransmitter pathway, e.g., one of the genes listed in Table 11; a serotonergic neurotransmitter pathway, e.g., one of the genes listed in Table 12; a nucleotide receptor, e.g., one of the genes listed in Table 13; an ion channel, e.g., one of the genes listed in Table 14; markers of undifferentiated or not fully differentiated cells, preferably nerve cells, e.g., one of the genes listed in Table 15; the sonic hedgehog signaling pathway, e.g., one of the genes in Table 16; calcium binding, e.g., one of the genes listed in Table 17; or a neurotrophic factor receptor, e.g., one of the genes listed in Table 18.

The ion channel encoded by or associated with the gene selected as the source of the regulatory sequence is preferably involved in generating and modulating ion flux across the plasma membrane of neurons, including, but not limited to voltage-sensitive and/or cation-sensitive channels, e.g., a calcium, sodium or potassium channel.

In Tables 4-18 that follow, the common names of genes are listed, as well as their GeneCards identifiers (Rebhan et al., 1997, GeneCards: encyclopedia for genes, proteins and diseases, Weizmann Institute of Science, Bioinformatics Unit and Genome Center (Rehovot, Israel). GenBank accession numbers, UniGene accession numbers, and Mouse Genome Informatics (MGI). Database accession numbers where available are also listed. GenBank is the NIH genetic sequence database, an annotated collection of all publicly available DNA sequences (Benson et al., 2000, Nucleic Acids Res. 28(1): 15-18). The GenBank accession number is a unique identifier for a sequence record. An accession number applies to the complete record and is usually a combination of a letter(s) and numbers, such as a single letter followed by five digits (e.g., U12345), or two letters followed by six digits (e.g., AF123456).

Accession numbers do not change, even if information in the record is changed at the author's request. An original accession number might become secondary to a newer accession number, if the authors make a new submission that combines previous sequences, or if for some reason a new submission supercedes an earlier record.

UniGene (Schuler et al., 1996, A gene map of the human genome, Science 274(5287):540-6) is an experimental system for automatically partitioning GenBank sequences into a non-redundant set of gene-oriented clusters for cow, human, mouse, rat, and zebrafish. Within UniGene, expressed sequence tags (ESTs) and full-length mRNA sequences are organized into clusters that each represent a unique known or putative gene. Each UniGene cluster contains related information such as the tissue types in which the gene has been expressed and map location. Sequences are annotated with mapping and expression information and cross-referenced to other resources. Consequently, the collection may be used as a resource for gene discovery.

The Mouse Genome Informatics (MGI) Database (Jackson Laboratory, Bar Harbor, Me.) contains information on mouse genetic markers, mRNA and genomic sequence information, phenotypes, comparative mapping data, experimental mapping data, and graphical displays for genetic, physical, and cytogenetic maps.

TABLE 4

| Gene | GenBank and/or UniGene Accession Number | MGI Database Accession Number |
| --- | --- | --- |
| ADRB1 (adrenergic beta 1) | human: J03019 | MGI: 87937 |
| ADRB2 (adrenergic beta 2) | human: M15169 | MGI: 87938 |
| ADRB3 (adrenergic beta 3) | human: NM_000025, X70811, X72861, M29932, X70812, S53291, X70812 | MGI: 87939 |
| ADRA1A (adrenergic alpha1a) | human: D25235, U02569, AF013261, L31774, U03866 guinea pig: AF108016 | |
| ADRA1B (adrenergic alpha 1b) | human: U03865, L31773 | MGI: 104774 |
| ADRA1C (adrenergic alpha 1c) | human: U08994 mouse: NM_013461 | |
| ADRA1D (adrenergic alpha1d) | human: M76446, U03864, L31772, D29952, S70782 | MGI: 106673 |
| ADRA2A (adrenergic alpha2A) | human: M18415, M23533 | MGI: 87934 |
| ADRA2B (adrenergic alpha 2B) | human: M34041, AF005900 | MGI: 87935 |
| ADRA2C (adrenergic alpha 2C) | human: J03853, D13538, U72648 | MGI: 87936 |
| SLC6A2 Norepinephrine transporter (NET) | human: X91117, M65105, AB022846, AF061198 | MGI: 1270850 |

TABLE 5

| Gene | GenBank and/or UniGene Accession Number | MGI Database Accession Number |
| --- | --- | --- |
| CHRM1 (Muscarinic Ach M1) receptor | human: X15263, M35128 Y00508, X52068 | MGI: 88396 |
| CHRM2 (Muscarinic Ach M2) receptor | human: M16404, AB041391, X15264 mouse: AF264049 | |
| CHRM3 (Muscarinic Ach M3) receptor | human: U29589, AB041395, X15266 mouse: AF264050 | |
| CHRM4 (Muscarinic Ach M4) receptor | human: X15265, M16405 | MGI: 88399 |
| CHRM5 (Muscarinic Ach M5) receptor | human: AF026263, M80333 rat: NM_017362 mouse: AI327507 | |
| CHRNA1 (nicotinic alpha1) receptor | human: Y00762, X02502, S77094 | MGI: 87885 |
| CHRNA2 (nicotinic alpha2) receptor | human: U62431, Y16281 | MGI: 87886 |
| CHRNA3 (nicotinic alpha3) receptor | human: NM_000743, U62432, M37981, M86383, Y08418 | |
| CHRNA4 (nicotinic alpha4) receptor | human: U62433, L35901, Y08421, X89745, X87629 | MGI: 87888 |
| CHRNA5 (nicotinic alpha5) receptor | human: U62434, Y08419, M83712 | MGI: 87889 |
| CHRNA7 (nicotinic alpha7) receptor | human: X70297, Y08420, Z23141, U40583, U62436, L25827, AF036903 | MGI: 99779 |
| CHRNB1 (nicotinic Beta 1) receptor | human: X14830 | MGI: 87890 |
| CHRNB2 (nicotinic Beta 2) receptor | human: U62437, X53179, Y08415, AJ001935 | MGI: 87891 |
| CHRNB3 (nicotinic Beta 3) receptor | human: Y08417, X67513, U62438, RIKEN BB284174 | |
| CHRNB4 (nicotinic Beta 4) receptor | human: U48861, U62439, Y08416, X68275 | MGI: 87892 |
| CHRNG nicotinic gamma immature muscle receptor | human: X01715, M11811 | MGI: 87895 |
| CHRNE nicotinic epsilon receptor | human: X66403 mouse: NM_009603 | |
| CHRND nicotinic delta receptor | human: X55019 | MGI: 87893 |

TABLE 6

| Gene | GenBank and/or UniGene Accession Number | MGI Database Accession Number |
| --- | --- | --- |
| th (tyrosine hydroxylase) | human: M17589 | MGI: 98735 |
| dat (dopamine transporter) | human: NM_001044 | MGI: 94862 |
| dopamine receptor 1 | human UniGene: X58987, S58541, X55760, X55758 | MGI: 99578 |
| dopamine receptor 2 | human UniGene: X51362, M29066, AF050737, S62137, X51645, M30625, S69899 | MGI: 94924 |
| dopamine receptor 3 | human UniGene: U25441, U32499 | MGI: 94925 |
| dopamine receptor 4 | human UniGene: L12398, S76942 | MGI: 94926 |

TABLE 6-continued

| Gene | GenBank and/or UniGene Accession Number | MGI Database Accession Number |
|---|---|---|
| dopamine receptor 5 | human UniGene: M67439, M67439, X58454 | MGI: 94927 |
| dbh dopamine beta hydroxylase | human UniGene: X13255 | MGI: 94864 |

TABLE 7

| Gene | GenBank and/or UniGene Accession Number | MGI Database Accession Number |
|---|---|---|
| GABA A A2 GABRA2 GABA receptor A2 | human: S62907 | MGI: 95614 |
| GABA A A3 GABRA3 GABA receptor A3 | human: S62908 | MGI: 95615 |
| GABA A A4 GABRB4 GABA receptor A4 | human: NM_000809, U30461 | MGI: 95616 |
| GABA A A5 GABRB5 GABA receptor A5 | human: NM_000810, L08485, AF061785, AF061785, AF061785 | |
| GABA A A6 GABRB6 GABA receptor A6 | human: S81944, AF053072 | MGI: 95618 |
| GABA B1 GABRB1 GABA receptor B1 | human: X14767, M59216 | MGI: 95619 |
| GABA B2 GABRB2 GABA receptor B2 | human: S67368, S77554, S77553 mouse: MM4707 | |
| GABA B3 GABRB3 GABA receptor B3 | human: M82919 | MGI: 95621 |
| GABRG1 GABA-A receptor, gamma 1 subunit | | MGI: 103156 |
| GABRG2 GABA-A receptor, gamma 2 subunit | human: X15376 | MGI: 95623 |
| GABRG3 GABA-A receptor, gamma 3 subunit | human: S82769 | |
| GABRD GABA-A receptor, delta subunit | human: AF016917 | MGI: 95622 |
| GABRE GABA-A receptor, epsilon subunit | human: U66661, Y07637, Y09765, U92283, Y09763, U92285 mouse: NM_017369 | |
| GABA A pi GABRP GABA-A receptor, pi subunit | human: U95367, AF009702 | |
| GABA A theta GABA receptor theta | mouse NM_020488 | |
| GABA R1a GABA receptor rho 1 | human: M62400 | MGI: 95625 |

TABLE 7-continued

| Gene | GenBank and/or UniGene Accession Number | MGI Database Accession Number |
|---|---|---|
| GABRR1 GABA receptor rho 1 GABA R2 GABA receptor a rho 2 GABRR2 GABA receptor rho 2 | human: M86868 | MGI: 95626 |

TABLE 8

| Gene | GenBank and/or UniGene Accession Number | MGI Database Accession Number |
|---|---|---|
| GRIA1 GluR1 | human: NM_000827, M64752, X58633 M81886 mouse: NM_008165 | |
| GRIA2 GlurR2 | human: L20814 rat: M85035 mouse: AF250875 | |
| GRIA3 GluR3 | human: U10301, X82068, U10302 rat: M85036 | |
| GRIA4 GluR4 | human: U16129 rat: NM_017263 | |
| GRIK1 glutamate ionotropic kainate 1 gluR5 | human: L19058, U16125, AF107257, AF107259 | MGI: 95814 |
| GRIK2 gluR6 | human: U16126 mouse: NM_010349, RIKEN BB359097 | |
| GRIK3 gluR7 | human: U16127 mouse: AF245444 | |
| GRIK4 KA1 | human: S67803 | MGI: 95817 |
| GRIK5 KA2 | human: S40369 | MGI: 95818 |
| GRIN1 NR1nmdar1 NMDA receptor 1 | human: D13515, L05666, L13268, L13266, AF015731, AF015730, U08106, L13267 | MGI: 95819 |
| GRIN2A NR2A NMDA receptor 2A | human: NM_000833, U09002, U90277 mouse: NM_008170 | |
| GRIN2B NR2B NMDA receptor 2B | human: NM_000834, U11287, U90278, U88963 | MGI: 95821 |
| GRIN2C NR2C NMDA receptor 2C | human: U77782, L76224 | MGI: 95822 |
| GRIN2D NR2D NMDA receptor 2D | human: U77783 | MGI: 95823 |
| GRM1 mGluR 1a and 1b alternate splicing type I mGluR1a | human: NM_000838, L76627, AL035698, U31215, AL035698, U31216, L76631 mouse: BB275384, BB181459, BB177876 | |
| GRM2 mGluR 2 type II mGluR2 | human: L35318 Sheep: AF229842 | |
| GRM3 | human: X77748 | |

TABLE 8-continued

| Gene | GenBank and/or UniGene Accession Number | MGI Database Accession Number |
|---|---|---|
| mGluR3 type II mGluR3 | mouse: AH008375; MM45836 | |
| GRM4 mGluR4 type III mGluR4 | human: X80818 | |
| GRM5 mGluR5a and 5b alt splice 32 residues mGluR5 | human: D28538, D28539 mouse: AF140349 | |
| GRM6 mGluR6 type III mGluR6 | human: NM_000843, U82083, AJ245872, AJ245871 rat: AJ245718 | |
| GRM7 mGluR7 type III mGluR7 | human: NM_000844, X94552 mouse: RIKEN BB357072 | |
| GRM8 mGluR8 type III mGluR8 | human: NM_000845, U95025, AJ236921, AJ236922, AC000099 mouse: U17252 | |
| GRID2 glut ionotropic delta | human: AF009014 | MGI: 95813 |
| excitatory amino acid transporter2 glutamate/ aspartate transporter II glutamate transporter GLT1 glutamate transporter SLC1A2 glial high affinity glutamate transporter EAAC1 neural SLC1A1 neuronal/ epithelial high affinity glutamate transporter | human: U03505, U01824, Z32517, D85884 | MGI: 101931 |
| EEAT1 SLC1A3 glial high affinity | human: U08989, U03506, U06469 | MGI: 105083 |
| | human: D26443, AF070609, L19158, U03504, Z31713 | MGI: 99917 |
| glutamate transporter EAAT4 neural SLC1A6 high affinity aspartate/ glutamate transporter | human: U18244, AC004659 | MGI: 1096331 |

TABLE 9

| Gene | GenBank and/or UniGene Accession Number | MGI Database Accession Number |
|---|---|---|
| Glycine receptors alpha 1 GLRA1 | human: X52009 | MGI: 95747 |
| Glycine receptors alpha 2 GLRA2 | human: X52008, AF053495 | MGI: 95748 |
| Glycine receptors alpha 3 GLRA3 | human: AF017724, U93917, AF018157 mouse: AF214575 | |
| Glycine receptors alpha 4 GLRA4 | no human mouse: X75850, X75851, X75852, X75853 | |
| glycine receptor beta GLRB | human: U33267, AF094754, AF094755 | MGI: 95751 |

TABLE 10

| Gene | GenBank and/or UniGene Accession Number | MGI Database Accession Number |
|---|---|---|
| Histamine H1-receptor 1 | human: Z34897, D28481, X76786, AB041380, D14436, AF026261 | MGI: 107619 |
| Histamine H2-receptor 2 | human: M64799, AB023486, AB041384 | MGI: 108482 |
| Histamine H3-receptor 3 | human: NM_007232 mouse: MM31751 | |

TABLE 11

| Gene | GenBank and/or UniGene Accession Number | MGI Database Accession Number |
|---|---|---|
| orexin OX-A hypocretin 1 | human: AF041240 | MGI: 1202306 |
| Orexin B | | |
| Orexin receptor OX1R HCRTR1 | human: AF041243 | |
| Orexin receptor OX2R HCRTR2 | human: AF041245 | |
| leptinR-long Leptin receptor long form | human: U66497, U43168, U59263, U66495, U52913, U66496, U52914, U52912, U50748, AK001042 | MGI: 104993 |

TABLE 11-continued

| Gene | GenBank and/or UniGene Accession Number | MGI Database Accession Number |
|---|---|---|
| MCH<br>melanin concentrating hormone<br>PMCH | human: M57703, S63697 | |
| MC3R<br>MC3 receptor<br>melanocortin 3 receptor | human: GDB: 138780<br>mouse: MM57183 | MGI: 96929 |
| MC4R<br>MC4 receptor<br>melanocortin 4 receptor | human: S77415, L08603,<br>NM_005912 | |
| MC5R<br>MC5 receptor<br>melanocortin 5 receptor | human: L27080, Z25470, U08353 | MGI: 99420 |
| prepro-CRF<br>corticotropin-releasing factor<br>precursor | human: V00571<br>rat: X03036, M54987 | |
| CRH<br>corticotropin releasing hormone | | |
| CRHR1<br>CRH/CRF receptor 1 | human: L23332, X72304, L23333,<br>AF039523, U16273 | MGI: 88498 |
| CRF R2<br>CRH/CRF receptor 2 | human: U34587, AF019381,<br>AF011406, AC004976, AC004976 | MGI: 894312 |
| CRHBP<br>CRF binding protein | human: X58022, S60697 | MGI: 88497 |
| Urocortin | human: AF038633 | MGI: 1276123 |
| POMC<br>Pro-opiomelanocortin | human: V01510, M38297, J00292,<br>M28636 | MGI: 97742 |
| CART<br>cocaine and amphetamine<br>regulated transcript | human: U20325, U16826 | MGI: 1351330 |
| NPY<br>Neuropeptide Y<br>prepro NPY | human: K01911, M15789,<br>M14298, AC004485 | MGI: 97374 |
| NPY1R<br>NPY Y1 receptor<br>Neuropeptide Y1 receptor | human: M88461, M84755,<br>NM_000909 | MGI: 104963 |
| NPY2R<br>NPY Y2 receptor<br>Neuropeptide Y2 receptor | human: U42766, U50146, U32500,<br>U36269, U42389, U76254,<br>NM_000910 | MGI: 108418 |
| NPY Y4 receptor<br>Npy4R Neuropeptide Y4 receptor<br>(mouse) | human: Z66526, U35232, U42387 | MGI: 105374 |
| NPY Y5 receptor<br>Npy5R Neuropeptide Y5 receptor<br>(mouse) | human: U94320, U56079, U66275<br>mouse: MM10685 | MGI: 108082 |
| NPY Y6 receptor<br>Npy6r Neuropeptide Y receptor<br>(mouse) | human: D86519, U59431, U67780 | MGI: 1098590 |
| CCK<br>cholecystokinin | human: NM_000729, L00354 | MGI: 88297 |
| CCKa receptor<br>CCKAR cholecystokinin receptor | human: L19315, D85606, L13605<br>U23430 | MGI: 99478 |
| CCKb receptor<br>CCKBR cholecystokinin receptor | human: D13305, L04473, L08112,<br>L07746, L10822, D21219,<br>S70057, AF074029 | MGI: 99479 |
| AGRP<br>agouti related peptide | human: NM_001138, U88063,<br>U89485 | MGI: 892013 |
| Galanin | human: M77140, L11144 | MGI: 95637 |
| GALP<br>Galanin like peptide<br>See, Jureus et al., 2000,<br>Endocrinology 141(7): 2703-06. | | |
| GalR1 receptor<br>GALNR1<br>galanin receptor1 | human: NM_001480, U53511,<br>L34339, U23854 | MGI: 1096364 |
| GalR2 receptor<br>GALNR2<br>galanin receptor2 | human: AF040630, AF080586,<br>AF042782 | MGI: 1337018 |
| GalR3 receptor<br>GALNR3<br>Galr3<br>galanin receptor3 | human: AF073799, Z97630,<br>AF067733 | MGI: 1329003 |
| UTS2<br>prepro-urotensin II | human: Z98884, AF104118 | MGI: 1346329 |
| GPR14<br>Urotensin receptor | human: AI263529<br>mouse: AI385474 | |

TABLE 11-continued

| Gene | GenBank and/or UniGene Accession Number | MGI Database Accession Number |
|---|---|---|
| SST somatostatin | human: J00306 | MGI: 98326 |
| SSTR1 somatostatin receptor sst1 | human: M81829 | MGI: 98327 |
| SSTR2 somatostatin receptor sst2 | human: AF184174 M81830 AF184174 | MGI: 98328 |
| SSTR3 somatostatin receptor sst3 | human: M96738, Z82188 | MGI: 98329 |
| SSTR4 somatostatin receptor sst4 | human: L14856, L07833, D16826, AL049651 | MGI: 105372 |
| SSTR5 somatostatin receptor sst5 | human: D16827, L14865, AL031713 | MGI: 894282 |
| GPR7 G protein-coupled receptor 7 opioid-somatostatin-like receptor | human: U22491 | MGI: 891989 |
| GPR8 G protein-coupled receptor 8 opioid-somatostatin-like receptor | human: U22492 | |
| PENK (pre Pro Enkephalin) | human: V00510, J00123 | MGI: 104629 |
| PDYN (Pre pro Dynorphin) | human: K02268, AL034562, X00176 | MGI: 97535 |
| OPRM1 μ opiate receptor | human: L25119, L29301, U12569, AL132774 | MGI: 97441 |
| OPRK1 k opiate receptor | human: U11053, L37362, U17298 | MGI: 97439 |
| OPRD1 delta opiate receptor | human: U07882, U10504, AL009181 | MGI: 97438 |
| OPRL1 ORL1 opioid receptor-like receptor | human: X77130, U30185 | MGI: 97440 |
| VR1 Vanilloid receptor subtype 1 | human: NM_018727, BE466577 mouse: BE623398, | |
| VRL-1 vanilloid receptor-like protein 1 | human: NM_015930 rat: AB040873 | MGI: 1341836 |
| VR1L1 vanilloid receptor type 1 like protein 1 VRL1 vanilloid receptor-like protein 1 | mouse: NM_011706 | |
| VR-OAC vanilloid receptor-related osmotically activated channel | human: AC007834 | |
| CNR1 cannaboid receptors CB1 | human: U73304, X81120, X81120, X54937, X81121 | MGI: 104615 |
| EDN1 endothelin 1 ET-1 | human: J05008, Y00749, S56805, Z98050, M25380 | MGI: 95283 |
| GHRH growth hormone releasing hormone | human: L00137, AL031659, L00137 | MGI: 95709 |
| GHRHR growth hormone releasing hormone receptor | human: AF029342, U34195, mouse: NM_010285 | |
| PNOC nociceptin orphanin FQ/nocistatin | human: X97370, U48263, X97367 | MGI: 105308 |
| NPFF neuropeptide FF precursor | human: AF005271 mouse: RIKEN BB365815 | |
| neuropeptide FF receptor neuropeptide AF receptor G-protein coupled receptor HLWAR77 G-protein coupled receptor NPGPR | human: AF257210, NM_004885, AF119815 | |
| GRP gastrin releasing peptide preprogastrin-releasing peptide | human: K02054, S67384, S73265, M12512 | MGI: 95833 |
| GRPR gastrin releasing peptide receptor BB2 | human: M73481, U57365 | MGI: 95836 |
| NMB neuromedin B | human: M21551 mouse: AI327379 | |
| NMBR neuromedin B receptor BB1 | human: M73482 | MGI: 1100525 |
| BRS3 bombesin like receptor subtype-3 uterine bombesin receptor | human: Z97632, L08893, X76498 mouse: AB010280 | |

TABLE 11-continued

| Gene | GenBank and/or UniGene Accession Number | MGI Database Accession Number |
|---|---|---|
| GCG PROglucagon GLP-1 GLP-2 | human: J04040, X03991, V01515 | MGI: 95674 |
| GCGR glucagon receptor | human: U03469, L20316 | MGI: 99572 |
| GLP1R GLP1 receptor | human: AL035690, U01104, U01157, L23503, U01156, U10037 | MGI: 99571 |
| GLP2R GLP2 receptor | human: AF105367 mouse: AF166265 | |
| VIP vasoactive intestinal peptide | human: M36634, M54930, M14623, M33027, M11554, L00158, M36612 | MGI: 98933 |
| SCT secretin | mouse: NM_011328, X73580 | |
| PPYR1 pancreatic polypeptide receptor 1 | human: Z66526, U35232, U42387 | MGI: 105374 |
| OXT pre pro Oxytocin | human: M25650, M11186, X03173 mouse: NM_011025, M88355 | |
| OXTR OTR oxytocin receptor | human: X64878 | MGI: 109147 |
| AVP Preprovasopressin | human: M25647, X03172, M11166, AF031476, X62890, X62891 | MGI: 88121 |
| AVPR1A V1a receptor vasopressin receptor1a | human: U19906, L25615, S73899, AF030625, AF101725 mouse: NM_016847 | |
| AVPR1B V1b receptor vasopressin receptor1b | human: D31833, L37112, AF030512, AF101726 mouse: NM_011924 | |
| AVPR2 V2 receptor vasopressin receptor2 | human: Z11687, U04357, L22206, U52112, AF030626, AF032388, AF101727, AF101728 | MGI: 88123 |
| NTS proneurotensin/proneuromedin N Neurotensin tridecapeptide plus neuromedin N | human: NM_006183, U91618 mouse: MM64201 | |
| NTSR1 Neurotensin receptor NT1 | human: X70070 | MGI: 97386 |
| NTSR2 Neurotensin receptor NT2 | human: Y10148 mouse: NM_008747 | |
| SORT1 sortilin 1 neurotensin receptor 3 | human: X98248, L10377 | MGI: 1338015 |
| BDKRB1 Bradykinin receptor 1 | human: U12512, U48231, U22346, AJ238044, AF117819 | MGI: 88144 |
| BDKRB2 Bradykinin receptor B2 | human: X69680, S45489, S56772, M88714, X86164, X86163, X86165 | MGI: 102845 |
| GNRH1 GnRH gonadotrophin releasing hormone | human: X01059, M12578, X15215 | MGI: 95789 |
| GNRH2 GnRH gonadotrophin releasing hormone | human: AF036329 | |
| GNRHR GnRH gonadotrophin releasing hormone receptor | human: NM_000406, L07949, S60587, L03380, S77472, Z81148, U19602 | MGI: 95790 |
| CALCB calcitonin-related polypeptide, beta | human: X02404, X04861 | |
| CALCA calcitonin/calcitonin-related polypeptide, alpha | human: M26095, X00356, X03662, M64486, M12667, X02330, X15943 | MGI: 88249 |
| CALCR calcitonin receptor | human: L00587 | MGI: 101950 |
| TAC1 (also called tac2) neurokinin A | human: X54469, U37529, AC004140 | MGI: 98474 |
| TAC3 neurokinin B | human: NM_013251 rat: NM_017053 | |
| TACR2 neurokinin a (subK) receptor | human: M75105, M57414, M60284 | |
| TACR1 tachykinin receptor NK2 (Sub P | human: M84425, M74290, M81797, M76675, X65177, | MGI: 98475 |

TABLE 11-continued

| Gene | GenBank and/or UniGene Accession Number | MGI Database Accession Number |
|---|---|---|
| and K) | M84426 | |
| TACR3 tachykinin receptor NK3 (Sub P and K) neuromedin K | human: M89473 X65172 | |
| ADCYAP1 PACAP | human: X60435 | MGI: 105094 |
| NPPA atrial naturietic peptide (ANP) precursor atrial natriuretic factor (ANF) precursor pronatriodilatin precursor prepronatriodilatin | human: M54951, X01470, AL021155, M30262, K02043, K02044 | MGI: 97367 |
| NPPB atrial naturietic peptide (BNP) precursor | human: M25296, AL021155, M31776 mouse: NM_008726 | |
| NPR1 naturietic peptide receptor 1 | human: X15357, AB010491 | MGI: 97371 |
| NPR2 naturietic peptide receptor 2 | human: L13436, AJ005282, AB005647 | MGI: 97372 |
| NPR3 naturietic peptide receptor 3 | human: M59305, AF025998, X52282 | MGI: 97373 |
| VIPR1 VPAC1 VIP receptor 1 | human: NM_004624, L13288, X75299, X77777, L20295, U11087 | MGI: 109272 |
| VIPR2 VIP receptor 2 PACAP receptor | human: X95097, L36566, Y18423, L40764, AF027390 | MGI: 107166 |

TABLE 12

| Gene | GenBank and/or UniGene Accession Number | MGI Database Accession Number |
|---|---|---|
| 5HT1A serotonin receptor 1A | human: M83181, AB041403, M28269, X13556 | MGI: 96273 |
| 5HT2A serotonin receptor 2A | human: X57830 | MGI: 109521 |
| 5HT3 serotonin receptor 3 | human: AJ005205, D49394, S82612, AJ005205, AJ003079, AJ005205, AJ003080, AJ003078 | MGI: 96282 |
| 5HT1B 5HT1Db serotonin receptor 1B | human: M81590, M81590, D10995, M83180, L09732, M75128, AB041370, AB041377, AL049595 | MGI: 96274 |
| 5HT1D alpha serotonin receptor 1D | human: AL049576 | MGI: 96276 |
| 5HT1E serotonin receptor 1E | human: NM_000865, M91467, M92826, Z11166 | |
| 5HT2B serotonin receptor 2B | human: NM_000867, X77307, Z36748 | MGI: 109323 |
| 5HT2C serotonin receptor 2C | human: NM_000868, U49516, M81778, X80763, AF208053 | MGI: 96281 |
| 5HT4 serotonin receptor 4 (has 5 subtypes isoforms) | human: Y10437, Y08756, Y09586, Y13584, Y12505, Y12506, Y12507, AJ011371, AJ243213 | |
| 5HT5A serotonin receptor 5A | human: X81411 | MGI: 96283 |
| 5Ht5B serotonin receptor 5B | rat: L10073 | |
| 5HT6 serotonin receptor 6 | human: L41147, AF007141 | |
| 5HT7 serotonin receptor 7 | human: U68488, U68487, L21195, X98193 mouse: MM8053 | |
| sert serotonin transporter | human UniGene: L05568 | MGI: 96285 |
| TPRH TPH (Tph) tryptophan hydroxylase | human UniGene: AF057280, X52836, L29306 | MGI: 98796 |

TABLE 13

| Gene | GenBank and/or UniGene Accession Number | MGI Database Accession Number |
|---|---|---|
| P2RX1 P2x1 receptor purinergic receptor P2X, ligand-gated ion channel | human: U45448, X83688, AF078925, AF020498 | MGI: 1098235 |
| P2RX3 purinergic receptor P2X, ligand-gated ion channel, 3 | human: Y07683 mouse: RIKEN BB459124, RIKEN BB452419 | |
| P2RX4 purinergic receptor P2X, ligand-gated ion channel, 4 | human: U83993, Y07684, U87270, AF000234 | MGI: 1338859 |
| P2RX5 purinergic receptor P2X, ligand-gated ion channel, 5 | human: AF168787, AF016709, U49395, U49396, AF168787 rat: AF070573 | |
| P2RXL1 purinergic receptor P2X-like 1, orphan receptor | human UniGene: AB002058 | MGI: 1337113 |
| P2RX6 P2RX7 purinergic receptor P2X, ligand-gated ion channel, 7 | human: Y09561, Y12851 | MGI: 1339957 |
| P2RY1 purinergic receptor P2Y, G-protein coupled 1 | human: Z49205 | MGI: 105049 |

TABLE 13-continued

| Gene | GenBank and/or UniGene Accession Number | MGI Database Accession Number |
|---|---|---|
| P2RY2 purinergic receptor P2Y, G-protein coupled, 2 | human: U07225 S74902 rat: U56839 | |
| P2RY4 pyrimidinergic receptor P2Y, G-protein coupled, 4 | human: X91852, X96597, U40223 | |
| P2RY6 | human: X97058, U52464, | |
| pyrimidinergic receptor P2Y, G-protein coupled, 6 | AF007892, AF007891, AF007893 | |
| P2RY11 purinergic receptor P2Y, G-protein coupled, 11 | human: AF030335 | |

TABLE 14

| Gene | GenBank and/or UniGene Accession Number | MGI Database Accession Number |
|---|---|---|
| SCN1A sodium channel, voltage-gated, type I, alpha | human: X65362 | MGI: 98246 |
| SCN1B sodium channel, voltage-gated, type I, beta | human: L16242, L10338, U12194, NM_001037 | MGI: 98247 |
| SCN2B sodium channel, voltage-gated, type II, beta | human: AF049498, AF049497, AF007783 | MGI: 106921 |
| SCN5A sodium channel, voltage-gated, type V, alpha | human: M77235 | |
| SCN2A1 sodium channel, voltage-gated, type II, alpha 1 | | MGI: 98248 |
| SCN2A2 sodium channel, voltage-gated, type II, alpha 2 | human: M94055, X65361, M91803 | |
| SCN3A sodium channel, voltage-gated, type III, alpha | human: AB037777, AJ251507 | MGI: 98249 |
| SCN4A sodium channel, voltage-gated, type IV, alpha | human: M81758, L01983, L04236, U24693 | MGI: 98250 |
| SCN6A sodium channel, voltage-gated, type VII or VI | human: M91556 | |
| SCN8a SCN8A sodium channel, voltage-gated, type VIII | human: AF225988, AB027567 | MGI: 103169 |
| SCN9A sodium channel, voltage-gated, type IX, alpha | human: X82835, RIKEN BB468679 mouse: MM40146 | |
| SCN10A sodium channel, voltage-gated, type X, | human: NM_006514, AF117907 | |
| SCN11A sodium channel, voltage-gated, type XI, alpha | human: AF188679 | MGI: 1345149 |
| SCN12A sodium channel, voltage-gated, type XII, alpha | human: NM_014139 | |
| SCNN1A sodium channel, nonvoltage-gated 1 alpha | human: X76180, Z92978, L29007, U81961, U81961, U81961, U81961 | MGI: 101782 |
| SCN4B sodium channel, voltage-gated, type IV, beta | | |
| SCNN1B sodium channel, nonvoltage-gated 1, beta | human: X87159, L36593, AJ005383, AC002300, U16023 | |
| SCNN1D sodium channel, nonvoltage-gated 1, delta | human: U38254 | |
| SCNN1G sodium channel, nonvoltage-gated 1, gamma | human: X87160, L36592, U35630 | MGI: 104695 |
| CLCN1 chloride channel 1, skeletal muscle | human: Z25884, Z25587, M97820, Z25753 | MGI: 88417 |

TABLE 14-continued

| Gene | GenBank and/or UniGene Accession Number | MGI Database Accession Number |
| --- | --- | --- |
| CLCN2 chloride channel 2 | human: AF026004 | MGI: 105061 |
| CLCN3 chloride channel 3 ClC3 | human: X78520, AL117599, AF029346 | MGI: 103555 |
| CLCN4 chloride channel 4 | human: AB019432 X77197 | MGI: 104567 |
| CLCN5 chloride channel 5 | human: X91906, X81836 | MGI: 99486 |
| CLCN6 chloride channel 6 | human: D28475, X83378, AL021155, X99473, X99474, X96391, AL021155, AL021155, X99475, AL021155 | MGI: 1347049 |
| CLCN7 chloride channel 7 | human: AL031600, U88844, Z67743, AJ001910 | MGI: 1347048 |
| CLIC1 chloride intracellular channel 1 | human: X87689, AJ012008, X87689, U93205, AF129756 | |
| CLIC2 chloride intracellular channel 2 | human: NM_001289 | |
| CLIC3 chloride intracellular channel 3 | human: AF102166 | |
| CLIC5 chloride intracellular channel 5 | human: AW816405 | |
| CLCNKB chloride channel Kb | human: Z30644, S80315, U93879 | |
| CLCNKA chloride channel Ka | human: Z30643, U93878 | MGI: 1329026 |
| CLCA1 chloride channel, calcium activated, family member 1 | human: AF039400, AF039401 | MGI: 1316732 |
| CLCA2 chloride channel, calcium activated, family member 2 | human: AB026833 | |
| CLCA3 chloride channel, calcium activated, family member 3 | human: NM_004921 | |
| CLCA4 chloride channel, calcium activated, family member 4 | human: AK000072 | |
| KCNA1 kv1.1 potassium voltage-gated channel, shaker-related subfamily, member 1 | human: L02750 | MGI: 96654 |
| KCNA2 potassium voltage-gated channel, shaker-related subfamily, member 2 | human: Hs.248139, L02752 mouse: MM56930 | MGI: 96659 |
| KCNA3 potassium voltage-gated channel, shaker-related subfamily, member 3 | human: M85217, L23499, M38217, M55515 | MGI: 96660 |
| KCNA4 potassium voltage-gated channel, shaker-related subfamily, member 4 | human: M55514, M60450, L02751 | MGI: 96661 |
| KCNA4L potassium voltage-gated channel, shaker-related subfamily, member 4-like | | |
| KCNA5 potassium voltage-gated channel, shaker-related subfamily, member 5 | human: Hs.150208, M55513, M83254, M60451, M55513 mouse: MM1241 | MGI: 96662 |
| KCNA6 potassium voltage-gated channel, shaker-related subfamily, member 6 | human: X17622 | MGI: 96663 |
| KCNA7 potassium voltage-gated channel, shaker-related subfamily, member 7 | | MGI: 96664 |
| KCNA10 potassium voltage-gated channel, shaker-related subfamily, member 10 | human: U96110 | |
| KCNB1 | human: L02840, L02840, X68302, | MGI: 96666 |

TABLE 14-continued

| Gene | GenBank and/or UniGene Accession Number | MGI Database Accession Number |
|---|---|---|
| potassium voltage-gated channel, Shab-related subfamily, member 1 | AF026005 | |
| KCNB2 potassium voltage-gated channel, Shab-related subfamily, member 2 | human: Hs.121498, U69962 mouse: MM154372 | |
| KCNC1 potassium voltage-gated channel, Shaw-related subfamily, member 1 | human: L00621, S56770 | MGI: 96667 |
| KCNC2 potassium voltage-gated channel, Shaw-related subfamily, member 2 | | MGI: 96668 |
| KCNC3 potassium voltage-gated channel, Shaw-related subfamily, member 3 | human: AF055989 | MGI: 96669 |
| KCNC4 potassium voltage-gated channel, Shaw-related subfamily, member 4 | human: M64676 | MGI: 96670 |
| KCND1 potassium voltage-gated channel, Shal-related family, member 1 | human: AJ005898, AF166003 | MGI: 96671 |
| KCND2 potassium voltage-gated channel, Shal-related subfamily, member 2 | human: AB028967, AJ010969, AC004888 | |
| KCND3 potassium voltage-gated channel, Shal-related subfamily, member 3 | human: AF120491, AF048713, AF048712, AL049557 | |
| KCNE1 potassium voltage-gated channel, Isk-related family, member 1 | mouse: NM_008424 | |
| KCNE1L potassium voltage-gated channel, Isk-related family, member 1-like | human: AJ012743, NM_012282 | |
| KCNE2 potassium voltage-gated channel, Isk-related family, member 2 | human: AF302095 | |
| KCNE3 potassium voltage-gated channel, Isk-related family, member 3 | human: NM_005472, rat: AJ271742 mouse: MM18733 | |
| KCNE4 potassium voltage-gated channel, Isk-related family, member 4 | mouse: MM24386 | |
| KCNF1 potassium voltage-gated channel, subfamily F, member 1 | human: AF033382 | |
| KCNG1 potassium voltage-gated channel, subfamily G, member 1 | human: AF033383, AL050404 | |
| KCNG2 potassium voltage-gated channel, subfamily G, member 2 | human: NM_012283 | |
| KCNH1 potassium voltage-gated channel, subfamily H (eag-related), member 1 | human: AJ001366, AF078741, AF078742 mouse: NM_010600 | |
| KCNH2 potassium voltage-gated channel, subfamily H (eag-related), member 2 | human: U04270, AJ010538, AB009071, AF052728 | MGI: 1341722 |
| KCNH3 potassium voltage-gated channel, subfamily H (eag-related), member 3 | human: AB022696, AB033108, Hs.64064 mouse: NM_010601, MM100209 | |

TABLE 14-continued

| Gene | GenBank and/or UniGene Accession Number | MGI Database Accession Number |
|---|---|---|
| KCNH4 potassium voltage-gated channel, subfamily H (eag-related), member 4 | human: AB022698 rat: BEC2 | |
| KCNH5 potassium voltage-gated channel, subfamily H (eag-related), member 5 | human: Hs.27043 mouse: MM44465 | |
| KCNJ1 potassium inwardly-rectifying channel, subfamily J, member 1 | human: U03884, U12541, U12542, U12543 rat: NM_017023 | |
| KCNJ2 potassium inwardly-rectifying channel, subfamily J, member 2 | human: U16861, U12507, U24055, AF011904, U22413, AF021139 | MGI: 104744 |
| KCNJ3 potassium inwardly-rectifying channel, subfamily J, member 3 | human: U50964 U39196 mouse: NM_008426 | |
| KCNJ4 potassium inwardly-rectifying channel, subfamily J, member 4 | human: Hs.32505, U07364, Z97056, U24056, Z97056 mouse: MM104760 | MGI: 104743 |
| KCNJ5 potassium inwardly-rectifying channel, subfamily J, member 5 | human: NM_000890 | MGI: 104755 |
| KCNJ6 potassium inwardly-rectifying channel, subfamily J, member 6 | human: Hs.11173, U52153, D87327, L78480, S78685, AJ001894 mouse: NM_010606, MM4276 rat: NM_013192 | |
| KCNJ8 potassium inwardly-rectifying channel, subfamily J, member 8 | human: D50315, D50312 | MGI: 1100508 |
| KCNJ9 potassium inwardly-rectifying channel, subfamily J, member 9 | human: U52152 | MGI: 108007 |
| KCNJ10 potassium inwardly-rectifying channel, subfamily J, member 10 | human: Hs.66727, U52155, U73192, U73193 | MGI: 1194504 |
| KCNJ11 potassium inwardly-rectifying channel, subfamily J, member 11 | human: Hs.248141, D50582 mouse: MM4722 | MGI: 107501 |
| KCNJ12 potassium inwardly-rectifying channel, subfamily J, member 12 | human: AF005214, L36069 | MGI: 108495 |
| KCNJ13 potassium inwardly-rectifying channel, subfamily J, member 13 | human: AJ007557, AB013889, AF061118, AJ006128, AF082182 rat: AB034241, AB013890, AB034242 guinea pig: AF200714 | |
| KCNJ14 potassium inwardly-rectifying channel, subfamily J, member 14 | human: Hs.278677 mouse: Kir2.4, MM68170 | |
| KCNJ15 potassium inwardly-rectifying channel, subfamily J, member 15 | human: Hs.17287, U73191, D87291, Y10745 mouse: AJ012368, kir4.2, MM44238 | |
| KCNJ16 potassium inwardly-rectifying channel, subfamily J, member 1 | human: NM_018658, Kir5.1 mouse: AB016197 | |
| KCNK1 potassium channel, subfamily K, member 1 (TWIK-1) | human: U76996, U33632, U90065 | MGI: 109322 |
| KCNK2 potassium channel, subfamily K, member 2 (TREK-1) | human: AF004711, RIKEN BB116025 | |
| KCNK3 potassium channel, subfamily K, member 3 (TASK) | human: AF006823 | MGI: 1100509 |
| KCNK4 potassium inwardly-rectifying channel, subfamily K, member 4 | human: AF247042, AL117564 mouse: NM_008431 | |
| KCNK5 potassium channel, subfamily K, member 5 (TASK-2) | human: NM_003740, AK001897 mouse: AF259395 | |

TABLE 14-continued

| Gene | GenBank and/or UniGene Accession Number | MGI Database Accession Number |
|---|---|---|
| KCNK6 potassium channel, subfamily K, member 6 (TWIK-2) | human: AK022344 | |
| KCNK7 potassium channel, subfamily K, member 7 | human: NM_005714 mouse: MM23020 | MGI: 1341841 |
| KCNK8 potassium channel, subfamily K, member 8 | mouse: NM_010609 | |
| KCNK9 potassium channel, subfamily K, member 9 | human: AF212829 guinea pig: AF212828 | |
| KCNK10 potassium channel, subfamily K, member 10 (TREK2) | human: AF279890 | |
| KCNN1 potassium intermediate/small conductance calcium-activated channel, subfamily N, member 1 | human: NM_002248, U69883 | |
| KCNN2 potassium intermediate/small conductance calcium-activated channel, subfamily member 2 (hsk2) | mouse: MM63515 | |
| KCNN4 potassium intermediate/small conductance calcium-activated channel, subfamily N, member 4 | human: Hs.10082, AF022797, AF033021, AF000972, AF022150 mouse: MM9911 | MGI: 1277957 |
| KCNQ1 potassium voltage-gated channel, KQT-like subfamily, member 1 | human: U89364, AF000571, AF051426, AJ006345, AB015163, AB015163, AJ006345 | MGI: 108083 |
| KCNQ2 potassium voltage-gated channel, KQT-like subfamily, member 2 | human: Y15065, D82346, AF033348, AF074247, AF110020 | MGI: 1309503 |
| KCNQ3 potassium voltage-gated channel, KQT-like subfamily, member 3 | human: NM_004519, AF033347, AF071491 | MGI: 1336181 |
| KCNQ4 potassium voltage-gated channel, KQT-like subfamily, member 4 | human: Hs.241376, AF105202, AF105216 mouse: AF249747 | |
| KCNQ5 potassium voltage-gated channel, KQT-like subfamily, member 5 | human: NM_019842 | |
| KCNS1 potassium voltage-gated channel, delayed-rectifier, subfamily S, member 1 | human: AF043473 mouse: NM_008435 | |
| KCNS2 potassium voltage-gated channel, delayed-rectifier, subfamily S, member 2 | mouse: NM_008436 | |
| KCNS3 potassium voltage-gated channel, delayed-rectifier, subfamily S, member 3 | human: AF043472 | |
| KCNAB1 potassium voltage-gated channel, shaker-related subfamily, beta member 1 | L39833, U33428, L47665, X83127, U16953 | MGI: 109155 |
| KCNAB2 potassium voltage-gated channel, shaker-related subfamily, beta member 2 | human: U33429, AF044253, AF029749 mouse: NM_010598 | |
| KCNAB3 potassium voltage-gated channel, shaker-related subfamily, beta member 3 | human: NM_004732 mouse: MM57241 | MGI: 1336208 |
| KCNJN1 potassium inwardly-rectifying channel, subfamily J, inhibitor 1 | human: Hs.248143, U53143 | |
| KCNMA1 | human: U11058, U13913, U11717, | MGI: 99923 |

TABLE 14-continued

| Gene | GenBank and/or UniGene Accession Number | MGI Database Accession Number |
|---|---|---|
| potassium large conductance calcium-activated channel, subfamily M, alpha member 1 | U23767, AF025999 | |
| kcnma3 potassium large conductance calcium-activated channel, subfamily M, alpha member 3 | mouse: NM_008432 | |
| KCNMB1 potassium large conductance calcium-activated channel, subfamily M, beta member 1 | rat: NM_019273 | |
| KCNMB2 potassium large conductance calcium-activated channel, subfamily M, beta member 2 | human: AF209747 mouse: NM_005832 | |
| KCNMB3L potassium large conductance calcium-activated channel, subfamily M, beta member 3-like | human: AP000365 | |
| KCNMB3 potassium large conductance calcium-activated channel | human: NM_014407, AF214561 | |
| KCNMB4 potassium large conductance calcium-activated channel, sub M, beta 4 | human: AJ271372, AF207992, RIKEN BB329438, RIKEN BB265233 | |
| HCN1 hyperpolarization activated cyclic nucleotide-gated potassium channel 1 | | MGI: 1096392 |
| Cav1.1 α1 1.1 CACNA1S calcium channel, voltage-dependent, L type, alpha 1S subunit | human: L33798, U30707 | MGI: 88294 |
| Cav1.2 α1 1.2 CACNA1C calcium channel, voltage-dependent, L type, alpha 1C subunit | human: Z34815, L29536, Z34822, Z34534, L04569, Z34817, Z34809, Z34813, Z34814, Z34820, Z34810, Z34811, L29529, Z34819, Z74996, Z34812, Z34816, AJ224873, Z34818, Z34821, AF070589, Z26308, M92269 | |
| Cav1.3 α1 1.3 CACNA1D calcium channel, voltage-dependent, L type, alpha 1D subunit | human: M83566, M76558, D43747, AF055575 | MGI: 88293 |
| Cav1.4 α1 1.4 CACNA1F calcium channel, voltage-dependent, L type, alpha 1F subunit | human: AJ224874, AF235097, AJ006216, AF067227, U93305 | MGI: 1859639 |
| Cav2.1 α1 2.1 CACNA1A P/Q type calcium channel, voltage-dependent, P/Q type, alpha 1A subunit | human: U79666, AF004883, AF004884, X99897, AB035727, U79663, U79665, U79664, U79667, U79668, AF100774 | MGI: 109482 |
| Cav2.2 α1 2.2 CACNA1B calcium channel, voltage-dependent, L type, alpha 1B subunit | human: M94172, M94173, U76666 | MGI: 88296 |
| Cav2.3 α1 2.3 CACNA1E calcium channel, voltage-dependent, alpha 1E subunit | human: L29385, L29384, L27745 | MGI: 106217 |
| Cav3.1 α1 3.1 CACNA1G calcium channel, voltage-dependent, alpha 1G subunit | human: AB012043, AF190860, AF126966, AF227746, AF227744, AF134985, AF227745, AF227747, AF126965, AF227749, AF134986, AF227748, AF227751, AF227750, AB032949, AF029228 | MGI: 1201678 |
| Cav3.2 α1 3.2 CACNA1H calcium channel, voltage-dependent, alpha 1H subunit | human: AF073931, AF051946, AF070604 | |
| Cav3.3 α1 3.3 CACNA1I calcium channel, voltage-dependent, alpha 1I subunit | human: AF142567, AL022319, AF211189, AB032946 | |

TABLE 15

| Gene | GenBank and/or UniGene Accession Number | MGI Database Accession Number |
|---|---|---|
| NES (nestin) | no human | MGI: 101784 |
| scip | human: L26494 | MGI: 101896 |

TABLE 16

| Gene | GenBank and/or UniGene Accession Number | MGI Database Accession Number |
|---|---|---|
| Shh (Sonic Hedgehog) | human: L38518 | MGI: 98297 |
| Smoothened Shh receptor | human: U84401, AF114821 | MGI: 108075 |
| Patched Shh binding protein | human: NM_000264 rat: AF079162 | |

TABLE 17

| Gene | GenBank and/or UniGene Accession Number | MGI Database Accession Number |
|---|---|---|
| CALB1 (calbindin d28 K) | human: X06661, M19879, | MGI: 88248 |
| CALB2 (calretinin) | human: NM_001740, X56667, X56668 | MGI: 101914 |
| PVALB (parvalbumin) | human: X63578, X63070, Z82184, X52695, Z82184 | MGI: 97821 |

TABLE 18

| Gene | GenBank and/or UniGene Accession Number | MGI Database Accession Number |
|---|---|---|
| NTRK2 (Trk B) | human: U12140, X75958, S76473, S76474 | MGI: 97384 |
| GFRA1 (GFR alpha 1) | human: NM_005264, AF038420, AF038421, U97144, AF042080, U95847, AF058999 | MGI: 1100842 |
| GFRA2 (GFRalpha 2) | human: U97145, AF002700, U93703 | MGI: 1195462 |
| GFRA3 (GFRalpha 3) | human: AF051767 | MGI: 1201403 |
| trka Neurotrophin receptor | human: M23102, X03541, X04201, X06704, X62947, M23102, X62947, M23102, AB019488, M12128 | MGI: 97383 |
| trkc Neurotrophin receptor | human: U05012, U05012, S76475, AJ224521, S76476, AF052184 | MGI: 97385 |
| ret Neurotrophic factor receptor | human: S80552 | MGI: 97902 |

All of the sequences identified by the sequence database identifiers in Tables 4-18 are hereby incorporated by reference in their entireties.

In yet another aspect of the invention, a promoter directs tissue-specific expression of the tagged ribosomal protein or mRNA binding protein sequence to which it is operably linked. For example, expression of the tagged ribosomal protein or mRNA binding protein coding sequences may be controlled by any tissue-specific promoter/enhancer element known in the art. Promoters that may be used to control expression include, but are not limited to, the following animal transcriptional control regions that exhibit tissue specificity and that have been utilized in transgenic animals: elastase I gene control region, which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); enolase promoter, which is active in brain regions, including the striatum, cerebellum, CA1 region of the hippocampus, or deep layers of cerebral neocortex (Chen et al., 1998, Molecular Pharmacology 54(3): 495-503); insulin gene control region, which is active in pancreatic beta cells (Hanahan, 1985, Nature 315: 115-22); immunoglobulin gene control region, which is active in lymphoid cells (Grosschedl et al., 1984, Cell 38:647-58; Adames et al., 1985, Nature 318:533-38; Alexander et al., 1987, Mol. Cell. Biol. 7:1436-44); mouse mammary tumor virus control region, which is active in testicular, breast, lymphoid and mast cells (Leder et al., 1986, Cell 45:485-95); albumin gene control region, which is active in liver (Pinkert et al., 1987, Genes and Devel. 1:268-76); alpha-fetoprotein gene control region which is active in liver (Krumlauf et al., 1985, Mol. Cell. Biol. 5:1639-48; Hammer et al., 1987, Science 235:53-58); alpha 1-antitrypsin gene control region, which is active in the liver (Kelsey et al., 1987, Genes and Devel. 1:161-71); 13-globin gene control region, which is active in myeloid cells (Mogram et al., 1985, Nature 315:338-40; Kollias et al., 1986, Cell 46:89-94); myelin basic protein gene control region, which is active in oligodendrocyte cells in the brain (Readhead et al., 1987, Cell 48:703-12); myosin light chain-2 gene control region, which is active in skeletal muscle (Sani, 1985, Nature 314:283-86); and gonadotropic releasing hormone gene control region which is active in the hypothalamus (Mason et al., 1986, Science 234:1372-78).

In other embodiments, the gene sequence from which the regulatory sequence derives is protein kinase C, gamma (GenBank Accession Number: Z15114 (human); MGI Database Accession Number: MGI:97597); fos (UniGene No. MM5043 (mouse)); TH-elastin; Pax7 (Mansouri, 1998, The role of Pax3 and Pax7 in development and cancer, Crit. Rev. Oncog. 9(2):141-9); Eph receptor (Mellitzer et al., 2000, Control of cell behaviour by signalling through Eph receptors and ephrins; Curr. Opin. Neurobiol. 10(3):400-08; Suda et al., 2000, Hematopoiesis and angiogenesis, Int. J. Hematol. 71(2):99-107; Wilkinson, 2000, Eph receptors and ephrins: regulators of guidance and assembly, Int. Rev. Cytol. 196: 177-244; Nakamoto, 2000, Eph receptors and ephrins, Int. J. Biochem. Cell Biol. 32(1):7-12; Tallquist et al., 1999, Growth factor signaling pathways in vascular development, Oncogene 18(55):7917-32); islet-1 (Bang et al., 1996, Regulation of vertebrate neural cell fate by transcription factors, Curr. Opin. Neurobiol. 6(1):25-32; Ericson et al., 1995, Sonic hedgehog: a common signal for ventral patterning along the rostrocaudal axis of the neural tube, J. Dev. Biol. 39(5):809-16; 0-actin; thy-1 (Caroni, 1997, Overexpression of growth-associated proteins in the neurons of adult transgenic mice, J. Neurosci. Methods 71(1):3-9).

Nucleic acids of the invention may include all or a portion of the upstream regulatory sequences of the selected gene. The characterizing gene regulatory sequences preferably direct expression of the tagged ribosomal protein or mRNA binding protein sequences in substantially the same pattern as the endogenous characterizing gene within transgenic organism, or tissue derived therefrom.

In certain embodiments, the nucleic acids encoding the molecularly tagged ribosomal proteins or mRNA binding proteins may be selectively expressed in random but distinct subsets of cells, as described in Feng et al. (2000, Imaging neuronal subsets in transgenic mice expressing multiple spectral variants of GFP, Neuron 28(0:41-51, which is hereby incorporated by reference in its entirety). Using such methods, independently generated transgenic lines may express the nucleic acids encoding the molecularly tagged ribosomal proteins or mRNA binding proteins in a unique pattern, even though all incorporate identical regulatory elements.

5.6. Introduction of Vectors into Host Cells

In one aspect of the invention, a vector containing the nucleic acid encoding the tagged ribosomal protein or tagged mRNA binding protein and regulatory sequences (preferably characterizing gene regulatory sequences) can be introduced transiently or stably into the genome of a host cell or be maintained episomally. In another aspect of the invention, the vector can be transiently transfected wherein it is not integrated, but is maintained as an episome.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., bacterium such as *E. coli*) or eukaryotic cell (e.g., a cell from a yeast, plant, insect (e.g., *Drosophila*), amphibian, amniote, or mammal, to name but a few), preferably a vertebrate cell, more preferably a mammalian cell, and most preferably, a mouse cell. In certain embodiments, the host cell is a human cell, either a cultured cell, or in certain embodiments, an immortalized cultured cell or primary human cell. In specific embodiments, the host cells are human embryonic stem cells, or other human stem cells (or murine stem cells, including embryonic stem cells), tumor cells or cancer cells (particularly circulating cancer cells such as those resulting from leukemias and other blood system cancers). Host cells intended to be part of the invention include ones that comprise nucleic acids encoding one or more tagged ribosomal or tagged mRNA binding proteins and, optionally, operably associated with characterizing gene sequences that have been engineered to be present within the host cell (e.g., as part of a vector). The invention encompasses genetically engineered host cells that contain any of the foregoing tagged ribosomal protein or tagged mRNA binding protein coding sequences, optionally operatively associated with a regulatory element (preferably from a characterizing gene, as described above) that directs the expression of the coding sequences in the host cell. Both cDNA and genomic sequences can be cloned and expressed. In a preferred aspect, the host cell is recombination deficient, i.e., Rec⁻, and used for BAC recombination. In specific embodiments the host cell may contain more than one type of ribosomal or mRNA binding protein fusion, where the fusion of the different ribosomal and mRNA binding proteins is to the same or different peptide tags.

A vector containing a nucleotide sequence of the invention can be introduced into the desired host cell by methods known in the art, e.g., transfection, transformation, transduction, electroporation, infection, microinjection, cell fusion, DEAE dextran, calcium phosphate precipitation, liposomes, LIPOFECTIN™ (source), lysosome fusion, synthetic cationic lipids, use of a gene gun or a DNA vector transporter, such that the nucleotide sequence is transmitted to offspring in the line. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

In certain embodiments, the vector is introduced into a cultured cell. In other embodiments, the vector is introduced into a proliferating cell (or population of cells), e.g., a tumor cell, a stem cell, a blood cell, a bone marrow cell, a cell derived from a tissue biopsy, etc.

Particularly preferred embodiments of the invention encompass methods of introduction of the vector containing the nucleic acid of the invention, using pronuclear injection of a nucleic acid construct of the invention into the mononucleus of a mouse embryo and infection with a viral vector comprising the construct. Methods of pronuclear injection into mouse embryos are well-known in the art and described in Hogan et al. 1986, Manipulating the Mouse Embryo, Cold Spring Harbor Laboratory Press, New York, N.Y. and Wagner et al., U.S. Pat. No. 4,873,191, issued Oct. 10, 1989, herein incorporated by reference in their entireties.

In preferred embodiments, a vector containing the nucleic acid of the invention is introduced into any genetic material which ultimately forms a part of the nucleus of the zygote of the animal to be made transgenic, including the zygote nucleus. In one embodiment, the nucleic acid of the invention can be introduced in the nucleus of a primordial germ cell which is diploid, e.g., a spermatogonium or oogonium. The primordial germ cell is then allowed to mature to a gamete which is then united with another gamete or source of a haploid set of chromosomes to form a zygote. In another embodiment, the vector containing the nucleic acid of the invention is introduced in the nucleus of one of the gametes, e.g., a mature sperm, egg or polar body, which forms a part of the zygote. In preferred embodiments, the vector containing the nucleic acid of the invention is introduced in either the male or female pronucleus of the zygote. More preferably, it is introduced in either the male or the female pronucleus as soon as possible after the sperm enters the egg. In other words, right after the formation of the male pronucleus when the pronuclei are clearly defined and are well separated, each being located near the zygote membrane.

In a most preferred embodiment, the vector containing the nucleic acid of the invention is added to the male DNA complement, or a DNA complement other than the DNA complement of the female pronucleus, of the zygote prior to its being processed by the ovum nucleus or the zygote female pronucleus. In an alternate embodiment, the vector containing the nucleic acid of the invention could be added to the nucleus of the sperm after it has been induced to undergo decondensation. Additionally, the vector containing the transgene may be mixed with sperm and then the mixture injected into the cytoplasm of an unfertilized egg. Perry et al., 1999, Science 284:1180-1183. Alternatively, the vector may be injected into the vas deferens of a male mouse and the male mouse mated with normal estrus females. Huguet et al., 2000, Mol. Reprod. Dev. 56:243-247.

Preferably, the nucleic acid of the invention is introduced using any technique so long as it is not destructive to the cell, nuclear membrane or other existing cellular or genetic structures. The nucleic acid of the invention is preferentially inserted into the nucleic genetic material by microinjection. Microinjection of cells and cellular structures is known and is used in the art. Also known in the art are methods of transplanting the embryo or zygote into a pseudopregnant female where the embryo is developed to term and the nucleic acid of the invention is integrated and expressed. See, e.g., Hogan et al 1986, *Manipulating the Mouse Embryo*, Cold Spring Harbor Laboratory Press, New York, N.Y.

Viral methods of inserting nucleic acids are known in the art.

For stable transfection of cultured mammalian cells, only a small fraction of cells may integrate the foreign DNA into their genome. The efficiency of integration depends upon the vector and transfection technique used. In order to identify and select integrants, a gene that encodes a selectable marker (e.g., for resistance to antibiotics) is generally introduced into the host cells along with a nucleotide sequence of the invention. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die). Such methods are particularly useful in methods involving homologous recombination in mammalian cells (e.g., in murine ES cells) prior to introducing the recombinant cells into mouse embryos to generate chimeras.

A number of selection systems may be used to select transformed host cells. In particular, the vector may contain certain detectable or selectable markers. Other methods of selection include but are not limited to selecting for another marker such as: the herpes simplex virus thymidine kinase (Wigler et al., 1977, Cell 11: 223), hypoxanthine-guanine phosphoribosyltransferase (Szybalska and Szybalski, 1962, Proc. Natl. Acad. Sci. USA 48: 2026), and adenine phosphoribosyltransferase (Lowy et al., 1980, Cell 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77: 3567; O'Hare et al., 1981, Proc. Natl. Acad. Sci. USA 78: 1527); gpt, which confers resistance to mycophenolic acid (Mulligan and Berg, 1981, Proc. Natl. Acad. Sci. USA 78: 2072); neo, which confers resistance to the aminoglycoside G-418 (Colberre-Garapin et al., 1981, J. Mol. Biol. 150: 1); and hygro, which confers resistance to hygromycin (Santerre et al., 1984, Gene 30: 147).

5.7. Methods of Producing Transformed Organisms

The nucleic acid of the invention may integrate into the genome of the founder organism (or an oocyte or embryo that gives rise to the founder organism), preferably by random integration. If random, the integration preferably does not knock out, e.g., insert into, an endogenous gene(s) such that the endogenous gene is not expressed or is mis-expressed.

In other embodiments, the nucleic acid of the invention may integrate by a directed method, e.g., by directed homologous recombination ("knock-in"), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996). Preferably, when homologous recombination is used, it does not knock out or replace the host's endogenous copy of the characterizing gene (or characterizing gene ortholog).

Methods for generating cells having targeted gene modifications through homologous recombination are known in the art. The construct will comprise at least a portion of the characterizing gene with a desired genetic modification, e.g., insertion of the nucleotide sequence coding for the tagged ribosomal protein and will include regions of homology to the target locus, i.e., the endogenous copy of the characterizing gene in the host's genome. DNA constructs for random integration need not include regions of homology to mediate recombination. Markers can be included for performing positive and negative selection for insertion of the nucleic acid of the invention.

To create a homologous recombinant organism, a homologous recombination vector is prepared in which the nucleotide sequence encoding the tagged ribosomal protein is flanked at its 5' and 3' ends by characterizing gene sequences to allow for homologous recombination to occur between the exogenous gene carried by the vector and the endogenous characterizing gene in an embryonic stem cell. The additional flanking nucleic acid sequences are of sufficient length for successful homologous recombination with the endogenous characterizing gene. Typically, several kilobases of flanking DNA (both at the 5' and 3' ends) are included in the vector. Methods for constructing homologous recombination vectors and homologous recombinant animals are described further in Thomas and Capecchi, 1987, Cell 51: 503; Bradley, 1991, Curr. Opin. Bio/Technol. 2: 823-29; and PCT Publication Nos. WO 90/11354, WO 91/01140, WO 92/0968, and WO 93/04169.

A transgenic animal is a non-human animal, preferably a mammal, more preferably a rodent such as a rat or mouse, in which one or more of the cells of the animal includes a nucleic acid of the invention, i.e., has a non-endogenous (i.e., heterologous) nucleic acid sequence present as an extrachromosomal element in a portion of its cell or stably integrated into its germ line DNA (i.e., in the genomic sequence of most or all of its cells). Other examples of transgenic animals include non-human primates, sheep, dogs, cows, goats, chickens, amphibians, etc. The invention also includes transgenic plants and fungi (including yeast). Unless otherwise indicated, it will be assumed that a transgenic animal comprises stable changes to the germline sequence. Heterologous nucleic acid is introduced into the germ line of such a transgenic animal by genetic manipulation of, for example, embryos or embryonic stem cells of the host animal.

As discussed above, transformed organisms of the invention, e.g., transgenic animals, are preferably generated by random integration of a vector containing a nucleic acid of the invention into the genome of the organism, for example, by pronuclear injection in an animal zygote as described above. Other methods involve introducing the vector into cultured embryonic cells, for example ES cells, and then introducing the transformed cells into animal blastocysts, thereby generating a "chimeras" or "chimeric animals", in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

A homologously recombinant organism may include, but is not limited to, a recombinant animal, such as a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

In a preferred embodiment, a transgenic animal of the invention is created by introducing a nucleic acid of the invention, encoding the characterizing gene regulatory sequences operably linked to nucleotide sequences encoding a tagged ribosomal protein, into the male pronuclei of a fertilized oocyte, e.g., by microinjection or retroviral infection, and allowing the oocyte to develop in a pseudopregnant female foster animal. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191, in Hogan, Manipulating the Mouse Embryo, (Cold Spring Harbor Laboratory Press, Cold Spring Harbor, N.Y., 1986) and in Wakayama et al., 1999, Proc. Natl. Acad. Sci. USA, 96:14984-89. Similar methods are used for production of other transgenic animals.

A transgenic founder animal can be identified based upon the presence of the nucleic acid of the invention in its genome and/or expression of mRNA encoding the nucleic acid of the invention in tissues or cells of the animals. A transgenic founder animal can then be used to breed additional animals carrying the nucleic acid of the invention as described supra. Moreover, transgenic animals carrying the nucleic acid of the invention can further be bred to other transgenic animals carrying other nucleic acids of the invention.

In another embodiment, the nucleic acid of the invention is inserted into the genome of an embryonic stem (ES) cell, followed by injection of the modified ES cell into a blastocyst-stage embryo that subsequently develops to maturity and serves as the founder animal for a line of transgenic animals.

In another embodiment, a vector bearing a nucleic acid of the invention is introduced into ES cells (e.g., by electroporation) and cells in which the introduced gene has homologously recombined with the endogenous gene are selected. See, e.g., Li et al., 1992, Cell 69:915. For embryonic stem (ES) cells, an ES cell line may be employed, or embryonic cells may be obtained freshly from a host, e.g. mouse, rat, guinea pig, etc.

After transformation, ES cells are grown on an appropriate feeder layer, e.g., a fibroblast-feeder layer, in an appropriate medium and in the presence of appropriate growth factors, such as leukemia inhibiting factory (LIF). Cells that contain the construct may be detected by employing a selective medium. Transformed ES cells may then be used to produce transgenic animals via embryo manipulation and blastocyst injection. (See, e.g., U.S. Pat. Nos. 5,387,742, 4,736,866 and 5,565,186 for methods of making transgenic animals.)

Stable expression of the construct is preferred. For example, ES cells that stably express a nucleotide sequence encoding a tagged ribosomal protein may be engineered. Rather than using vectors that contain viral origins of replication, ES host cells can be transformed with DNA, e.g., a plasmid, controlled by appropriate expression control elements (e.g., promoter, enhancer, sequences, transcription terminators, polyadenylation sites, etc.), and a selectable marker. Following the introduction of the foreign DNA, engineered ES cells may be allowed to grow for 1-2 days in an enriched media, and then are switched to a selective media. The selectable marker in the recombinant plasmid confers resistance to the selection and allows cells to stably integrate the plasmid into their chromosomes and expanded into cell lines. This method may advantageously be used to engineer ES cell lines that express a nucleotide sequence encoding a tagged ribosomal protein.

The selected ES cells are then injected into a blastocyst of an animal (e.g., a mouse) to form aggregation chimeras. See, e.g., Bradley, 1987, in *Teratocarcinomas and Embryonic Stem Cells: A Practical Approach*, Robertson, ed., IRL, Oxford, 113-52. Blastocysts are obtained from 4 to 6 week old superovulated females. The ES cells are trypsinized, and the modified cells are injected into the blastocoel of the blastocyst. After injection, the blastocysts are implanted into the uterine horns of suitable pseudopregnant female foster animal. Alternatively, the ES cells may be incorporated into a morula to form a morula aggregate which is then implanted into a suitable pseudopregnant female foster animal. Females are then allowed to go to term and the resulting litters screened for mutant cells having the construct.

The chimeric animals are screened for the presence of the modified gene. By providing for a different phenotype of the blastocyst and the ES cells, chimeric progeny can be readily detected. Males and female chimeras having the modification are mated to produce homozygous progeny. Only chimeras with transformed germline cells will generate homozygous progeny. If the gene alterations cause lethality at some point in development, tissues or organs can be maintained as allergenic or congenic grafts or transplants, or in in vitro culture.

Progeny harboring homologously recombined or integrated DNA in their germline cells can be used to breed animals in which all cells of the animal contain the homologously recombined DNA by germline transmission of the nucleic acid of the invention.

Clones of the non-human transgenic animals described herein can also be produced according to the methods described in Wilmut et al., 1997, Nature 385: 810-13 and PCT Publication NOS. WO 97/07668 and WO 97/07669.

Once the transgenic mice are generated they may be bred and maintained using methods well known in the art. By way of example, the mice may be housed in an environmentally controlled facility maintained on a 10 hour dark: 14 hour light cycle. Mice are mated when they are sexually mature (6 to 8 weeks old). In certain embodiments, the transgenic founders or chimeras are mated to an unmodified animal (i.e., an animal having no cells containing the nucleic acid of the invention). In a preferred embodiment, the transgenic founder or chimera is mated to C57BL/6 mice (Jackson Laboratories). In a specific embodiment where the nucleic acid of the invention is introduced into ES cells and a chimeric mouse is generated, the chimera is mated to 129/Sv mice, which have the same genotype as the embryonic stem cells. Protocols for successful creation and breeding of transgenic mice are known in the art (Manipulating the Mouse Embryo. A Laboratory Manual, 2nd edition. B. Hogan, Beddington, R., Costantini, F. and Lacy, E., eds. 1994. Cold Spring Harbor Laboratory Press: Plainview, N.Y.). Preferably, a founder male is mated with two females and a founder female is mated with one male. Preferably two females are rotated through a male's cage every 1-2 weeks. Pregnant females are housed 1 or 2 per cage. Preferably, pups are ear tagged, genotyped, and weaned at 21 days. Males and females are housed separately. Preferably log sheets are kept for any mated animal, by example and not limitation, information should include pedigree, birth date, sex, ear tag number, source of mother and father, genotype, dates mated and generation.

More specifically, founder animals heterozygous for the nucleic acid of the invention may be mated to generate a homozygous line as follows: A heterozygous founder animal, designated as the $P_1$ generation, is mated with an offspring from a mating with a non-transgenic mouse, designated as the $F_1$ generation, transgenic mouse of the opposite sex which is heterozygous for the nucleic acid of the invention (backcross). Based on classical genetics, one fourth of the results of this backcross are homozygous for the nucleic acid of the invention. In a preferred embodiment, transgenic founders are individually backcrossed to an inbred or outbred strain of choice. Different founders should not be intercrossed, since different expression patterns may result from separate nucleic acid integration events.

The determination of whether a transgenic mouse is homozygous or heterozygous for the nucleic acid of the invention is as follows:

An offspring of the above described breeding cross is mated to a normal control non-transgenic animal. The offspring of this second mating are analyzed for the presence of the nucleic acid of the invention by the methods described below. If all offspring of this cross test positive for the nucleic acid of the invention, the mouse in question is homozygous for the nucleic acid of the invention. If, on the other hand, some of the offspring test positive for the nucleic acid of the invention and others test negative, the mouse in question is heterozygous for the nucleic acid of the invention.

An alternative method for distinguishing between a transgenic animal which is heterozygous and one which is homozygous for the nucleic acid of the invention is to measure the intensity with radioactive probes following Southern blot analysis of the DNA of the animal. Animals homozygous for the nucleic acid of the invention would be expected to produce higher intensity signals from probes specific for the nucleic acid of the invention than would heterozygote transgenic animals.

In a preferred embodiment, the transgenic mice are so highly inbred to be genetically identical except for sexual differences. The homozygotes are tested using backcross and intercross analysis to ensure homozygosity. Homozygous lines for each integration site in founders with multiple integrations are also established. Brother/sister matings for 20 or more generations define an inbred strain. In another preferred embodiment, the transgenic lines are maintained as hemizygotes.

In an alternative embodiment, individual genetically altered mouse strains are also cryopreserved rather than propagated. Methods for freezing embryos for maintenance of founder animals and transgenic lines are known in the art. Gestational day 2.5 embryos are isolated and cryopreserved in straws and stored in liquid nitrogen. The first straw and the last straw are subsequently thawed and transferred to foster females to demonstrate viability of the line with the assumption that all embryos frozen between the first straw and the last straw will behave similarly. If viable progeny are not observed a second embryo transfer will be performed. Methods for reconstituting frozen embryos and bringing the embryos to term are known in the art.

The nucleic acid encoding the molecularly tagged ribosomal protein or mRNA binding protein may be introduced into the genome of a founder plant (or embryo that gives rise to the founder plant) using methods well known in the art (Newell, 2000, Plant transformation technology. Developments and applications, Mol. Biotechnol. 16(1):53-65; Kumar and Fladung, 2001, Controlling transgene integration in plants, Trends in Plant Science 6 (4): 155-159). The nucleic acid encoding the molecularly tagged ribosomal protein or mRNA binding protein may be introduced into the genome of bacteria and yeast using methods described in Ausubel et al., 1989, Current Protocols in Molecular Biology, Green Publishing Associates and Wiley Interscience, N.Y., Chapters 1 and 13, respectively).

5.7.1. Homologous Recombination in Bacterial Artificial Chromosomes

The invention provides transformed organisms, e.g., transgenic mice, that express a tagged ribosomal protein within a chosen cell type (see infra). In preferred embodiments, BAC-mediated recombination (Yang, et al., 1997, Nat. Biotechnol. 15(9):859-865) is used to create the transformed organism. Such expression is achieved by using the endogenous regulatory sequences of a particular gene, wherein the expression of gene is a defining characteristic of the chosen cell type (as also described in PCT/US02/04765, entitled "Collections of Transgenic Animal Lines (Living Library)" by Serafini, published as WO 02/064749 on Aug. 22, 2002, which is incorporated by reference herein in its entirety). In another preferred embodiment, a collection of transgenic mice expressing tagged ribosomal proteins within a set of chosen cell types is assembled, as described infra.

Vectors used in the methods of the invention preferably can accommodate, and in certain embodiments comprise, large pieces of heterologous DNA such as genomic sequences. Such vectors can contain an entire genomic locus, or at least sufficient sequence to confer endogenous regulatory expression pattern and to insulate the expression of coding sequences from the effect of regulatory sequences surrounding the site of integration of the nucleic acid of the invention in the genome to mimic better wild type expression. When entire genomic loci or significant portions thereof are used, few, if any, site-specific expression problems of a nucleic acid of the invention are encountered, unlike insertions of nucleic acids into smaller sequences. In a preferred embodiment, the vector is a BAC containing genomic sequences into which a selected sequence encoding a molecular tag, e.g., an epitope tag, has been inserted by directed homologous recombination in bacteria, e.g., by the methods of Heintz WO 98/59060; Heintz et al., WO 01/05962; Yang et al., 1997, Nature Biotechnol. 15: 859-865; Yang et al., 1999, Nature Genetics 22: 327-35; which are incorporated herein by reference in their entireties.

Using such methods, a BAC can be modified directly in a recombination-deficient E. coli host strain by homologous recombination.

In a preferred embodiment, homologous recombination in bacteria is used for target-directed insertion of a sequence encoding a molecularly tagged ribosomal protein into the genomic DNA encoding sufficient regulatory sequences (termed "characterizing gene sequences") to promote expression of the tagged ribosomal protein in the endogenous expression pattern of the characterizing gene, which sequences have been inserted into the BAC. The BAC comprising the molecularly tagged ribosomal protein sequence under the regulation of this characterizing gene sequence is then recovered and introduced into the genome of a potential founder organism for a line of transformed organisms.

Preferably, the tagged ribosomal protein encoding sequence is inserted into the characterizing gene sequences using 5' direct fusion without the use of an IRES, i.e., such that the tagged ribosomal protein encoding sequence(s) is fused directly in frame to the nucleotide sequence encoding at least the first codon of the characterizing gene coding sequence and even the first two, four, five, six, eight, ten or twelve codons. In other embodiments, the tagged ribosomal protein encoding sequence is inserted into the 3' UTR of the characterizing gene and has its own IRES. In yet another specific embodiment, the tagged ribosomal protein encoding sequence is inserted into the 5' UTR of the characterizing gene with an IRES controlling the expression of the tagged ribosomal protein encoding sequence.

In a preferred aspect of the invention, the molecularly tagged ribosomal protein encoding sequence is introduced into a BAC containing characterizing gene regulatory sequences by the methods of Heintz et al. WO 98/59060 and Heintz et al., WO 01/05962, both of which are incorporated herein by reference in their entireties. The molecularly tagged sequence is introduced by performing selective homologous recombination on a particular nucleotide sequence contained in a recombination deficient host cell, i.e., a cell that cannot independently support homologous recombination, e.g., Rec A$^-$. The method preferably employs a recombination cassette that contains a nucleic acid containing the molecular-tag coding sequence that selectively integrates into a specific site in the characterizing gene by virtue of sequences homologous to the characterizing gene flanking the molecular-tag gene coding sequences on the shuttle vector when the recombination deficient host cell is induced to support homologous recombination (for example by providing a functional RecA gene on the shuttle vector used to introduce the recombination cassette).

In a preferred aspect, the particular nucleotide sequence that has been selected to undergo homologous recombination is contained in an independent origin based cloning vector introduced into or contained within the host cell, and neither the independent origin based cloning vector alone, nor the independent origin based cloning vector in combination with the host cell, can independently support homologous recombination (e.g., is RecA⁻). Preferably, the independent origin based cloning vector is a BAC or a bacteriophage-derived artificial chromosome (BBPAC) and the host cell is a host bacterium, preferably E. coli.

In another preferred aspect, sufficient characterizing gene sequences flank the tagged ribosomal protein encoding sequence to accomplish homologous recombination and target the insertion of the molecularly tagged ribosomal protein coding sequences to a particular location in the characterizing gene. The tagged ribosomal protein coding sequence and the homologous characterizing gene sequences are preferably present on a shuttle vector containing appropriate selectable markers and the RecA gene, optionally with a temperature sensitive origin of replication (see Heintz et al. WO 98/59060 and Heintz et al., WO 01/05962 such that the shuttle vector only replicates at the permissive temperature and can be diluted out of the host cell population at the non-permissive temperature. When the shuttle vector is introduced into the host cell containing the BAC, the RecA gene is expressed and recombination of the homologous shuttle vector and BAC sequences can occur, thus targeting the tagged ribosomal protein encoding sequence (along with the shuttle vector sequences and flanking characterizing gene sequences) to the characterizing gene sequences in the BAC.

The BACs can be selected and screened for integration of the molecularly tagged ribosomal protein coding sequences into the selected site in the characterizing gene sequences using methods well known in the art (e.g., methods described in Section 5, infra, and in Heintz et al., WO 98/59060 entitled "Methods of preforming (sic) homologous recombination based modification of nucleic acids in recombination deficient cells and use of the modified nucleic acid products thereof," and Heintz et al., WO 01/05962, entitled "Conditional homologous recombination of large genomic vector inserts"). Optionally, the shuttle vector sequences not containing the molecularly tagged ribosomal protein coding sequences (including the RecA gene and any selectable markers) can be removed from the BAC by resolution as described in Section 5 and in Heintz et al. WO 98/59060 and Heintz et al., WO 01/05962.

If the shuttle vector contains a negative selectable marker, cells can be selected for loss of the shuttle vector sequences. In an alternative embodiment, the functional RecA gene is provided on a second vector and removed after recombination, e.g., by dilution of the vector or by any method known in the art. The exact method used to introduce the tagged ribosomal protein encoding sequence and to remove (or not) the RecA (or other appropriate recombination enzyme) will depend upon the nature of the BAC library used (for example, the selectable markers present on the BAC vectors) and such modifications are within the skill in the art.

Once the BAC containing the characterizing gene regulatory sequences and molecularly tagged ribosomal protein coding sequences in the desired configuration is identified, it can be isolated from the host E. coli cells using routine methods and used to make transformed organisms as described infra).

BACs to be used in the methods of the invention selected and/or screened using the methods described supra.

Alternatively, the BAC can also be engineered or modified by "E-T cloning," as described by Muyrers et al. (1999, Nucleic Acids Res. 27(6): 1555-57, incorporated herein by reference in its entirety). Using these methods, specific DNA may be engineered into a BAC independently of the presence of suitable restriction sites. This method is based on homologous recombination mediated by the recE and recT proteins ("ET-cloning") (Zhang et al., 1998, Nat. Genet. 20(2): 123-28; incorporated herein by reference in its entirety). Homologous recombination can be performed between a PCR fragment flanked by short homology arms and an endogenous intact recipient such as a BAC. Using this method, homologous recombination is not limited by the disposition of restriction endonuclease cleavage sites or the size of the target DNA. A BAC can be modified in its host strain using a plasmid, e.g., pBAD-αβγ, in which recE and recT have been replaced by their respective functional counterparts of phage lambda (Muyrers et al., 1999, Nucleic Acids Res. 27(6): 1555-57). Preferably, a BAC is modified by recombination with a PCR product containing homology arms ranging from 27-60 bp. In a specific embodiment, homology arms are 50 bp in length.

In another embodiment, a nucleic acid of the invention is inserted into a yeast artificial chromosome (YAC) (Burke et al., 1987 Science 236: 806-12; and Peterson et al., 1997, Trends Genet. 13: 61).

In other embodiments, the nucleic acid of the invention is inserted into another vector developed for the cloning of large segments of mammalian DNA, such as a cosmid or bacteriophage P1 (Sternberg et al., 1990, Proc. Natl. Acad. Sci. USA 87: 103-07). The approximate maximum insert size is 30-35 kb for cosmids and 100 kb for bacteriophage P1.

In another embodiment, the nucleic acid of the invention is inserted into a P-1 derived artificial chromosome (PAC) (Mejia et al., 1997, Retrofitting vectors for *Escherichia coli*-based artificial chromosomes (PACs and BACs) with markers for transfection studies, Genome Res. 7(2):179-86). The maximum insert size is 300 kb.

5.8. Methods of Screening for Expression of Nucleic Acids of the Invention

Potential founder organisms for a line of transformed organisms can be screened for expression of the tagged ribosomal protein gene sequence in the population of cells characterized by expression of the endogenous characterizing gene.

Transformed organisms that exhibit appropriate expression (e.g., detectable expression having substantially the same expression pattern as the endogenous characterizing gene in a corresponding non-transgenic organism or anatomical region thereof, i.e., detectable expression in at least 80%, 90% or, preferably, 95% of the cells shown to express the endogenous gene by in situ hybridization) are selected as lines of transformed organisms.

In a preferred embodiment, immunohistochemistry using an antibody specific for the epitope tag is used to detect expression of the tagged ribosomal fusion protein product.

5.9. Expression of a Tagged Ribosomal Protein in a Population of Cells

The nucleic acid of the invention containing the nucleotide sequence encoding the tagged ribosomal protein can be expressed in the cell type of interest using methods well known in the art for recombinant gene expression. The choice of which method to use to express a DNA sequence encoding a tagged ribosomal protein in a chosen population of cells depends upon the population.

In certain embodiments, the chosen population of cells is a particular population of cells in culture that have been transfected with the construct encoding the tagged ribosomal protein, the expression construct is chosen to allow efficient and high-level expression in the type of cells present in culture, with the mRNA of the transfected population being isolated according to the methods described herein.

This mode of the invention would be particularly useful if one wanted to study global gene expression changes in cultured cells in response to the expression of a particular gene product, co-expressed with a tagged ribosomal subunit to allow isolation of mRNA from co-expressing cells.

In another embodiment, the expression construct can be contained within a viral vector or virus, which is introduced into the desired host cell as described above. This embodiment permits study of mRNA populations from transduced or infected cells, in vitro or in vivo.

In another embodiment, expression of the tagged ribosomal protein is driven in populations of cells by the characterizing gene regulatory element.

In another embodiment, the gene sequences encoding the characterizing gene regulatory element and the tagged ribosomal protein is introduced by homologous recombination.

In another embodiment, homologous recombination is used to introduce only the epitope tag gene coding sequences.

Methods for selecting for cells containing and expressing the nucleotide sequences encoding the fusion proteins of the invention are well known in the art. For example, in eukaryotic cells, the nucleotide sequence encoding the fusion protein is associated with (for example, present on the same vector as) a selectable marker such as dhfr. Cells having the dhfr selectable marker are resistant to the drug methotrexate. Increasing levels of methotrexate can also lead to amplification of the selectable marker (and, concomitantly, the sequence encoding the fusion protein of the invention). Once the selectable marker sequences have integrated into the host cell chromosome, the selectable marker sequences (and the sequences encoding the fusion protein of the invention) will be maintained by the host cells even in the absence of selection (e.g., in the absence of methotrexate when the selectable marker is dhfr).

5.10. Nucleic Acid Constructs

The invention provides vectors and lines of organisms that contain a nucleic acid construct, e.g., a transgene, that comprises the coding sequence for a peptide tag-ribosomal fusion protein or peptide tag-mRNA binding protein fusion protein under the control of a regulatory sequences for a "characterizing gene." The regulatory sequence is e.g., an endogenous promoter of a characterizing gene. This characterizing gene is endogenous to a host cell or host organism (or is an ortholog of an endogenous gene) and is expressed in a particular select population of cells of the organism. Expression of the nucleic acid construct is such that the nucleic acid construct has substantially the same expression pattern as the endogenous characterizing gene.

A transgene is a nucleotide sequence that has been or is designed to be incorporated into a cell, particularly a mammalian cell, that in turn becomes or is incorporated into a living animal such that the nucleic acid containing the nucleotide sequence is expressed (i.e., the mammalian cell is transformed with the transgene).

The characterizing gene sequence is preferably endogenous to the transformed organism, or is an ortholog of an endogenous gene, e.g., the human ortholog of a gene endogenous to the animal to be made transgenic. A nucleic acid construct comprising the tagged ribosomal protein and optionally, the characterizing gene sequence may be present as an extrachromosomal element in some or all of the cells of a transformed organisms such as a transgenic animal or, preferably, stably integrated into some or all of the cells, more preferably into the germ line DNA of the animal (i.e., such that the nucleic acid construct is transmitted to all or some of the animal's progeny), thereby directing expression of an encoded gene product (i.e., the tagged ribosomal protein gene product) in one or more cell types or tissues of the transformed organism. Unless otherwise indicated, it will be assumed that a transformed organism, e.g., a transgenic animal, comprises stable changes to the chromosomes of germline cells. In a preferred embodiment, the nucleic acid construct is present in the genome at a site other than where the endogenous characterizing gene is located. In other embodiments, the nucleic acid construct is incorporated into the genome of the organism at the site of the endogenous characterizing gene, for example, by homologous recombination.

In certain embodiments, transformed organisms are created by introducing a nucleic acid construct of the invention into its genome using methods routine in the art, for example, the methods described in Section 5.7, supra. A construct is a recombinant nucleic acid, generally recombinant DNA, generated for the purpose of the expression of a specific nucleotide sequence(s), or is to be used in the construction of other recombinant nucleotide sequences.

A transgenic construct of the invention includes at least the coding region for a peptide tag fused to the coding region for a ribosomal protein, operably linked to all or a portion of the regulatory sequences, e.g. a promoter and/or enhancer, of the characterizing gene. The transgenic construct optionally includes enhancer sequences and coding and other non-coding sequences (including intron and 5' and 3' untranslated sequences) from the characterizing gene such that the tagged ribosomal fusion protein gene is expressed in the same subset of cells as the characterizing gene. The tagged ribosomal fusion protein gene coding sequences and the characterizing gene regulatory sequences are operably linked, meaning that they are connected in such a way so as to permit expression of the tagged ribosomal protein gene when the appropriate molecules (e.g., transcriptional activator proteins) are bound to the characterizing gene regulatory sequences. Preferably the linkage is covalent, most preferably by a nucleotide bond. The promoter region is of sufficient length to promote transcription, as described in Alberts et al. (1989) in Molecular Biology of the Cell, 2d Ed. (Garland Publishing, Inc.).

In one aspect of the invention, the regulatory sequence is the promoter of a characterizing gene. Other promoters that direct tissue-specific expression of the coding sequences to which they are operably linked are also contemplated in the invention. In specific embodiments, a promoter from one gene and other regulatory sequences (such as enhancers) from other genes are combined to achieve a particular temporal and spatial expression pattern of the tagged ribosomal protein gene.

Methods that are well known to those skilled in the art can be used to construct vectors containing tagged ribosomal protein gene coding sequences operatively associated with the appropriate transcriptional and translational control signals of the characterizing gene. These methods include, for example, in vitro recombinant DNA techniques and in vivo genetic recombination. See, for example, the techniques described in Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties.

The tagged ribosomal protein gene coding sequences may be incorporated into some or all of the characterizing gene sequences such that the tagged ribosomal protein gene is expressed in substantially same expression pattern as the endogenous characterizing gene in the transformed organism, or at least in an anatomical region or tissue of the organisms (by way of example, in the brain, spinal chord, heart, skin, bones, head, limbs, blood, muscle, peripheral nervous system, etc. of an animal) containing the population of cells to be marked by expression of the tagged ribosomal protein gene coding sequences. By "substantially the same expression pattern" is meant that the tagged ribosomal protein gene coding sequences are expressed in at least 80%, 85%, 90%, 95%, and preferably 100% of the cells shown to express the endogenous characterizing gene by in situ hybridization. Because detection of the tagged ribosomal protein gene expression product may be more sensitive than in situ hybridization detection of the endogenous characterizing gene messenger RNA, more cells may be detected to express the tagged ribosomal protein gene product in the transformed organism than are detected to express the endogenous characterizing gene by in situ hybridization or any other method known in the art for in situ detection of gene expression.

For example, the nucleotide sequences encoding the tagged ribosomal protein gene protein product may replace the characterizing gene coding sequences in a genomic clone of the characterizing gene, leaving the characterizing gene regulatory non-coding sequences. In other embodiments, the tagged ribosomal protein gene coding sequences (either genomic or cDNA sequences) replace all or a portion of the characterizing gene coding sequence and the nucleotide sequence only contains the upstream and downstream characterizing gene regulatory sequences.

In a preferred embodiment, the tagged ribosomal protein gene coding sequences are inserted into or replace transcribed coding or non-coding sequences of the genomic characterizing gene sequences, for example, into or replacing a region of an exon or of the 3' UTR of the characterizing gene genomic sequence. Preferably, the tagged ribosomal protein gene coding sequences are not inserted into or replace regulatory sequences of the genomic characterizing gene sequences. Preferably, the tagged ribosomal protein gene coding sequences are also not inserted into or replace characterizing gene intron sequences.

In a preferred embodiment, the tagged ribosomal protein gene coding sequence is inserted into or replaces a portion of the 3' untranslated region (UTR) of the characterizing gene genomic sequence. In another preferred embodiment, the coding sequence of the characterizing gene is mutated or disrupted to abolish characterizing gene expression from the nucleic acid construct without affecting the expression of the tagged ribosomal protein gene. In certain embodiments, the tagged ribosomal protein gene coding sequence has its own internal ribosome entry site (IRES). For descriptions of IRESes, see, e.g., Jackson et al., 1990, Trends Biochem Sci. 15(12):477-83; Jang et al., 1988, J. Virol. 62(8):2636-43; Jang et al., 1990, Enzyme 44(1-4):292-309; and Martinez-Salas, 1999, Curr. Opin. Biotechnol. 10(5):458-64.

In another embodiment, the tagged ribosomal protein gene is inserted at the 3' end of the characterizing gene coding sequence. In a specific embodiment, the tagged ribosomal protein coding sequences are introduced at the 3' end of the characterizing gene coding sequence such that the nucleotide sequence encodes a fusion of the characterizing gene and the tagged ribosomal protein gene sequences.

Preferably, the tagged ribosomal protein gene coding sequences are inserted using 5' direct fusion wherein the tagged ribosomal protein gene coding sequences are inserted in-frame adjacent to the initial ATG sequence (or adjacent the nucleotide sequence encoding the first two, three, four, five, six, seven or eight amino acids of the characterizing gene protein product) of the characterizing gene, so that translation of the inserted sequence produces a fusion protein of the first methionine (or first few amino acids) derived from the characterizing gene sequence fused to the tagged ribosomal protein gene protein. In this embodiment, the characterizing gene coding sequence 3' of the tagged ribosomal protein gene coding sequences are not expressed. In yet another specific embodiment, a tagged ribosomal protein gene is inserted into a separate cistron in the 5' region of the characterizing gene genomic sequence and has an independent IRES sequence.

In certain embodiments, an IRES is operably linked to the tagged ribosomal protein gene coding sequence to direct translation of the tagged ribosomal protein gene. The IRES permits the creation of polycistronic mRNAs from which several proteins can be synthesized under the control of an endogenous transcriptional regulatory sequence. Such a construct is advantageous because it allows marker proteins to be produced in the same cells that express the endogenous gene (Heintz, 2000, Hum. Mol. Genet. 9(6): 937-43; Heintz et al., WO 98/59060; Heintz et al., WO 01/05962; which are incorporated herein by reference in their entireties).

Shuttle vectors containing an IRES, such as the pLD53 shuttle vector (see Heintz et al., WO 01/05962), may be used to insert the tagged ribosomal protein gene sequence into the characterizing gene. The IRES in the pLD53 shuttle vector is derived from EMCV (encephalomyocarditis virus) (Jackson et al., 1990, Trends Biochem Sci. 15(12):477-83; and Jang et al., 1988, J. Virol. 62(8):2636-43, both of which are hereby incorporated by reference). The common sequence between the first and second IRES sites in the shuttle vector is shown below. This common sequence also matches pIRES (Clontech) from 1158-1710.

(SEQ ID NO: 6)
TAACGTTACTGGCCGAAGCCGCTTGGAATAAGGCCGGTGTGCGTTTGTC

TATATGTTATTTTCCACCATATTGCCGTCTTTTGGCAATGTGAGGGCCC

GGAAACCTGGCCCTGTCTTCTTGACGAGCATTCCTAGGGGTCTTTCCCC

TCTCGCCAAAGGAATGCAAGGTCTGTTGAATGTCGTGAAGGAAGCAGTT

CCTCTGGAAGCTTCTTGAAGACAAACAACGTCTGTAGCGACCCTTTGCA

GGCAGCGGAACCCCCCACCTGGCGACAGGTGCCTCTGCGGCCAAAAGCC

ACGTGTATAAGATACACCTGCAAAGGCGGCACAACCCCAGTGCCACGTT

GTGAGTTGGATAGTTGTGGAAAGAGTCAAATGGCTCTCCTAAGCGTATT

CAACAAGGGGCTGAAGGATGCCCAGAAGGTACTCCATTGTATGGGATCT

GATCTGGGGCCTCGGTGCACATGCTTTACATGTGTTTAGTCGAGGTTAA

AAAAACGTCTAGGCCCCCCGAACCACGGGGACGTGGTTTTCCTTTGAAA

AACACCATGATA

In a specific embodiment, the EMCV IRES is used to direct independent translation of the tagged ribosomal protein gene coding sequences (Gorski and Jones, 1999, Nucleic Acids Research 27(9):2059-61).

In another embodiment, more than one IRES site is present in a nucleic acid of the invention to direct translation of more than one coding sequence. However, in this case, each IRES sequence must be a different sequence.

In certain embodiments where a tagged ribosomal protein gene is expressed conditionally, the tagged ribosomal protein gene coding sequence is embedded in the genomic sequence of the characterizing gene and is inactive unless acted on by a transactivator or recombinase, whereby expression of the tagged ribosomal protein gene can then be driven by the characterizing gene regulatory sequences.

In other embodiments the tagged ribosomal protein gene is expressed conditionally, through the activity of a gene that is an activator or suppressor of gene expression. In this case, the gene encodes a transactivator, e.g., tetR, or a recombinase, e.g., FLP, whose expression is regulated by the characterizing gene regulatory sequences. The tagged ribosomal protein gene is linked to a conditional element, e.g., the tet promoter, or is flanked by recombinase sites, e.g., FRT sites, and may be located any where within the genome. In such a system, expression of the transactivator gene, as regulated by the characterizing gene regulatory sequences, activates the expression of the tagged ribosomal protein gene.

In certain embodiments, exogenous translational control signals, including, for example, the ATG initiation codon, can be provided by the characterizing gene or some other heterologous gene. The initiation codon must be in phase with the reading frame of the desired coding sequence of the tagged ribosomal protein gene to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516-44).

The construct can also comprise one or more selectable markers that enable identification and/or selection of recombinant vectors. The selectable marker may be the tagged ribosomal protein gene product itself or an additional selectable marker not necessarily tied to the expression of the characterizing gene.

In a specific embodiment, a nucleic acid of the invention is expressed conditionally, using any type of inducible or repressible system available for conditional expression of genes known in the art, e.g., a system inducible or repressible by tetracycline ("tet system"); interferon; estrogen, ecdysone, or other steroid inducible system; Lac operator, progesterone antagonist RU486, or rapamycin (FK506). For example, a conditionally expressible nucleic acid of the invention can be created in which the coding region for the tagged ribosomal protein gene (and, optionally also the characterizing gene) is operably linked to a genetic switch, such that expression of the tagged ribosomal protein gene can be further regulated. One example of this type of switch is a tetracycline-based switch (see infra). In a specific embodiment, the tagged ribosomal protein gene product is the conditional enhancer or suppressor which, upon expression, enhances or suppresses expression of a selectable or detectable marker present either in the nucleic acid of the invention or elsewhere in the genome of the transformed organism.

A conditionally expressible nucleic acid of the invention can be site-specifically inserted into an untranslated region (UTR) of genomic DNA of the characterizing gene, e.g., the 3' UTR or the 5' region, so that expression of the nucleic acid via the conditional expression system is induced or abolished by administration of the inducing or repressing substance, e.g., administration of tetracycline or doxycycline, ecdysone, estrogen, etc., without interfering with the normal profile of gene expression (see, e.g., Bond et al., 2000, Science 289: 1942-46; incorporated herein by reference in its entirety). In the case of a binary system, the detectable or selectable marker operably linked to the conditional expression elements is present in the nucleic acid of the invention, but outside the characterizing gene coding sequences and not operably linked to characterizing gene regulatory sequences or, alternatively, on another site in the genome of the transformed organism.

Preferably, the nucleic acid of the invention comprises all or a significant portion of the genomic characterizing gene, preferably, at least all or a significant portion of the 5' regulatory sequences of the characterizing gene, most preferably, sufficient sequence 5' of the characterizing gene coding sequence to direct expression of the tagged ribosomal protein gene coding sequences in the same expression pattern (temporal and/or spatial) as the endogenous counterpart of the characterizing gene. In certain embodiments, the nucleic acid of the invention comprises one exon, two exons, all but one exon, or all but two exons, of the characterizing gene.

Nucleic acids comprising the characterizing gene sequences and tagged ribosomal protein gene coding sequences can be obtained from any available source. In most cases, all or a portion of the characterizing gene sequences and/or the tagged ribosomal protein gene coding sequences are known, for example, in publicly available databases such as GenBank, UniGene and the Mouse Genome Informatic (MGI) Database to name just a few, or in private subscription databases. With a portion of the sequence in hand, hybridization probes (for filter hybridization or PCR amplification) can be designed using highly routine methods in the art to identify clones containing the appropriate sequences (preferred methods for identifying appropriate BACs are discussed in Section 5.7.1, supra) for example in a library or other source of nucleic acid. If the sequence of the gene of interest from one species is known and the counterpart gene from another species is desired, it is routine in the art to design probes based upon the known sequence. The probes hybridize to nucleic acids from the species from which the sequence is desired, for example, hybridization to nucleic acids from genomic or DNA libraries from the species of interest.

By way of example and not limitation, genomic clones can be identified by probing a genomic DNA library under appropriate hybridization conditions, e.g., high stringency conditions, low stringency conditions or moderate stringency conditions, depending on the relatedness of the probe to the genomic DNA being probed. For example, if the probe and the genomic DNA are from the same species, then high stringency hybridization conditions may be used; however, if the probe and the genomic DNA are from different species, then low stringency hybridization conditions may be used. High, low and moderate stringency conditions are all well known in the art.

Procedures for low stringency hybridization are as follows (see also Shilo and Weinberg, 1981, Proc. Natl. Acad. Sci. USA 78:6789-6792): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film.

Procedures for high stringency hybridizations are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20 35×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography.

Moderate stringency conditions for hybridization are as follows: Filters containing DNA are pretreated for 6 hours at 55° C. in a solution containing 6×SSC, 5×Denhardt's solution, 0.5% SDS, and 100 µg/ml denatured salmon sperm DNA. Hybridizations are carried out in the same solution and 5-20×10$^6$ CPM $^{32}$P-labeled probe is used. Filters are incubated in the hybridization mixture for 18-20 hours at 55° C., and then washed twice for 30 minutes at 60° C. in a solution containing 1×SSC and 0.1% SDS.

With respect to the characterizing gene, all or a portion of the genomic sequence is preferred, particularly, the sequences 5' of the coding sequence that contain the regulatory sequences. A preferred method for identifying BACs containing appropriate and sufficient characterizing gene sequences to direct the expression of the tagged ribosomal protein gene coding sequences in substantially the same expression pattern as the endogenous characterizing gene is described in Section 5.7.1, supra.

Briefly, the characterizing gene genomic sequences are preferably in a vector that can accommodate significant lengths of sequence (for example, 10 kb's of sequence), such as cosmids, YACs, and, preferably, BACs, and encompass at least 50, 70, 80, 100, 120, 150, 200, 250 or 300 kb of sequence that comprises all or a portion of the characterizing gene sequence. The larger the vector insert, the more likely it is to identify a vector that contains the characterizing gene sequences of interest. Vectors identified as containing characterizing gene sequences can then be screened for those that are most likely to contain sufficient regulatory sequences from the characterizing gene to direct expression of the tagged ribosomal protein gene coding sequences in substantially the same pattern as the endogenous characterizing gene. In general, it is preferred to have a vector containing the entire genomic sequence for the characterizing gene. However, in certain cases, the entire genomic sequence cannot be accommodated by a single vector or such a clone is not available. In these instances (or when it is not known whether the clone contains the entire genomic sequence), preferably the vector contains the characterizing gene sequence with the start, i.e., the most 5' end, of the coding sequence in the approximate middle of the vector insert containing the genomic sequences and/or has at least 20 kb, 30 kb, 40 kb, 50 kb, 60 kb, 80 kb or 100 kb of genomic sequence on either side of the start of the characterizing gene coding sequence. This can be determined by any method known in the art, for example, but not by way of limitation, by sequencing, restriction mapping, PCR amplification assays, etc. In certain cases, the clones used may be from a library that has been characterized (e.g., by sequencing and/or restriction mapping) and the clones identified can be analyzed, for example, by restriction enzyme digestion and compared to database information available for the library. In this way, the clone of interest can be identified and used to query publicly available databases for existing contigs correlated with the characterizing gene coding sequence start site. Such information can then be used to map the characterizing gene coding sequence start site within the clone. Alternatively, the tagged ribosomal protein gene sequences (or any other heterologous sequences) can be targeted to the 5' end of the characterizing gene coding sequence by directed homologous recombination (for example as described in Section 5.7) in such a way that a restriction site unique or at least rare in the characterizing gene clone sequence is introduced. The position of the integrated tagged ribosomal protein gene coding sequences (and, thus, the 5' end of the characterizing gene coding sequence) can be mapped by restriction endonuclease digestion and mapping. The clone may also be mapped using internally generated fingerprint data and/or by an alternative mapping protocol based upon the presence of restriction sites and the T7 and SP6 promoters in the BAC vector, as described in Section 5.7.1, supra.

In certain embodiments, the tagged ribosomal protein gene coding sequences are to be inserted in a site in the characterizing gene sequences other than the 5' start site of the characterizing gene coding sequences, for example, in the 3' most translated or untranslated regions. In these embodiments, the clones containing the characterizing gene should be mapped to insure the clone contains the site for insertion in as well as sufficient sequence 5' of the characterizing gene coding sequences library to contain the regulatory sequences necessary to direct expression of the tagged ribosomal protein gene sequences in the same expression pattern as the endogenous characterizing gene.

Once such an appropriate vector containing the characterizing gene sequences, the tagged ribosomal protein gene can be incorporated into the characterizing gene sequence by any method known in the art for manipulating DNA. In a preferred embodiment, homologous recombination in bacteria is used for target-directed insertion of the tagged ribosomal protein gene sequence into the genomic DNA encoding the characterizing gene and sufficient regulatory sequences to promote expression of the characterizing gene in its endogenous expression pattern, which characterizing gene sequences have been inserted into a BAC (see Section 5.7.1, supra). The BAC comprising the tagged ribosomal protein gene and characterizing gene sequences is then introduced into the genome of a potential founder organism for generating a line of transformed organisms, using methods well known in the art, e.g., those methods described in Section 5.7, supra. Such transformed organisms are then screened for expression of the tagged ribosomal protein gene coding sequences that mimics the expression of the endogenous characterizing gene. Several different constructs containing nucleic acids of the invention may be introduced into several potential founder organisms and the resulting transformed organisms are then screened for the best, (e.g., highest level) and most accurate (best mimicking expression of the endogenous characterizing gene) expression of the tagged ribosomal protein gene coding sequences.

The nucleic acid construct can be used to transform a host or recipient cell or organism using well known methods, e.g., those described in Section 5.6, supra. Transformation can be either a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell. In one aspect of the invention, a vector is used for stable integration of the nucleic acid construct into the genome of the cell. Vectors include plasmids, retroviruses and other animal viruses, BACs, YACs, and the like.

5.11. Expression Using a Binary System

Since the level of expression of the tagged ribosomal protein within a cell may be important in the efficiency of the isolation procedure, in certain embodiments of the invention, a binary system can be used, in which the endogenous promoter drives expression of a protein that then activates a second expression construct. This second expression construct uses a strong promoter to drive expression of the tagged ribosomal protein at higher levels than is possible using the endogenous promoter itself.

In certain embodiments, a particular population-specific gene drives expression of a molecular switch (e.g., a recombinase, a transactivator) in a population-specific manner. This switch then activates high-level expression though a second regulatory element regulating expression of the tagged ribosomal protein.

For example, the molecularly tagged ribosomal protein coding sequence may be expressed conditionally, through the activity of a molecular switch gene which is an activator or suppressor of gene expression. In this case, the second gene encodes a transactivator, e.g., tetR, a recombinase, or FLP, whose expression is regulated by the characterizing gene regulatory sequences. The gene encoding the molecularly tagged ribosomal protein is linked to a conditional element, e.g., the tet promoter, or is flanked by recombinase sites, e.g., FRT sites, and may be located any where within the genome. In such a system, expression of the molecular switch gene, as regulated by the characterizing gene regulatory sequences, activates the expression of the molecular tag.

5.12. Conditional Transcriptional Regulation Systems

In certain embodiments, the tagged ribosomal protein gene can be expressed conditionally by operably linking at least the coding region for the tagged ribosomal protein gene to all or a portion of the regulatory sequences from the characterizing gene, and then operably linking the tagged ribosomal protein gene coding sequences and characterizing gene sequences to an inducible or repressible transcriptional regulation system.

Transactivators in these inducible or repressible transcriptional regulation systems are designed to interact specifically with sequences engineered into the vector. Such systems include those regulated by tetracycline ("tet systems"), interferon, estrogen, ecdysone, Lac operator, progesterone antagonist RU486, and rapamycin (FK506) with tet systems being particularly preferred (see, e.g., Gingrich and Roder, 1998, Annu. Rev. Neurosci. 21: 377-405; incorporated herein by reference in its entirety). These drugs or hormones (or their analogs) act on modular transactivators composed of natural or mutant ligand binding domains and intrinsic or extrinsic DNA binding and transcriptional activation domains. In certain embodiments, expression of the detectable or selectable marker can be regulated by varying the concentration of the drug or hormone in medium in vitro or in the diet of the transformed organism in vivo.

The inducible or repressible genetic system can restrict the expression of the detectable or selectable marker either temporally, spatially, or both temporally and spatially.

In a preferred embodiment, the control elements of the tetracycline-resistance operon of E. coli is used as an inducible or repressible transactivator or transcriptional regulation system ("tet system") for conditional expression of the detectable or selectable marker. A tetracycline-controlled transactivator can require either the presence or absence of the antibiotic tetracycline, or one of its derivatives, e.g., doxycycline (dox), for binding to the tet operator of the tet system, and thus for the activation of the tet system promoter (Ptet). Such an inducible or repressible tet system is preferably used in a mammalian cell.

In a specific embodiment, a tetracycline-repressed regulatable system (TrRS) is used (Agha-Mohammadi and Lotze, 2000, J. Clin. Invest. 105(9): 1177-83; incorporated herein by reference in its entirety). This system exploits the specificity of the tet repressor (tetR) for the tet operator sequence (tetO), the sensitivity of tetR to tetracycline, and the activity of the potent herpes simplex virus transactivator (VP16) in eukaryotic cells. The TrRS uses a conditionally active chimeric tetracycline-repressed transactivator (tTA) created by fusing the COOH-terminal 127 amino acids of vision protein 16 (VP16) to the COOH terminus of the tetR protein (which may be the tagged ribosomal protein gene). In the absence of tetracycline, the tetR moiety of tTA binds with high affinity and specificity to a tetracycline-regulated promoter (tRP), a regulatory region comprising seven repeats of tetO placed upstream of a minimal human cytomegalovirus (CMV) promoter or β-actin promoter (β-actin is preferable for neural expression). Once bound to the tRP, the VP16 moiety of tTA transactivates the detectable or selectable marker gene by promoting assembly of a transcriptional initiation complex. However, binding of tetracycline to tetR leads to a conformational change in tetR accompanied with loss of tetR affinity for tetO, allowing expression of the tagged ribosomal protein gene to be silenced by administering tetracycline. Activity can be regulated over a range of orders of magnitude in response to tetracycline.

In another specific embodiment, a tetracycline-induced regulatable system is used to regulate expression of a detectable or selectable marker, e.g., the tetracycline transactivator (tTA) element of Gossen and Bujard (1992, Proc. Natl. Acad. Sci. USA 89: 5547-51; incorporated herein by reference in its entirety).

In another specific embodiment, the improved tTA system of Shockett et al. (1995, Proc. Natl. Acad. Sci. USA 92: 6522-26, incorporated herein by reference in its entirety) is used to drive expression of the marker. This improved tTA system places the tTA gene under control of the inducible promoter to which tTA binds, making expression of tTA itself inducible and autoregulatory.

In another embodiment, a reverse tetracycline-controlled transactivator, e.g., rtTA2 S-M2, is used. rtTA2 S-M2 transactivator has reduced basal activity in the absence doxycycline, increased stability in eukaryotic cells, and increased doxycycline sensitivity (Urlinger et al., 2000, Proc. Natl. Acad. Sci. USA 97(14): 7963-68; incorporated herein by reference in its entirety).

In another embodiment, the tet-repressible system described by Wells et al. (1999, Transgenic Res. 8(5): 371-81; incorporated herein by reference in its entirety) is used. In one aspect of the embodiment, a single plasmid Tet-repressible system is used. Preferably, a "mammalianized" TetR gene, rather than a wild-type TetR gene (tetR) is used (Wells et al., 1999, Transgenic Res. 8(5): 371-81).

In other embodiments, expression of the tagged ribosomal protein gene is regulated by using a recombinase system that is used to turn on or off tagged ribosomal protein gene expression by recombination in the appropriate region of the genome in which the marker gene is inserted. Such a recombinase system, in which a gene that encodes a recombinase can be used to turn on or off expression of the tagged ribosomal protein gene (for review of temporal genetic switches and "tissue scissors" using recombinases, see Hennighausen and Furth, 1999, Nature Biotechnol. 17: 1062-63). Exclusive recombination in a selected cell type may be mediated by use of a site-specific recombinase such as Cre, FLP-wild type (wt), FLP-L or FLPe. Recombination may be effected by any art-known method, e.g., the method of Doetschman et al. (1987, Nature 330: 576-78; incorporated herein by reference in its entirety); the method of Thomas et al., (1986, Cell 44: 419-28; incorporated herein by reference in its entirety); the Cre-loxP recombination system (Sternberg and Hamilton, 1981, J. Mol. Biol. 150: 467-86; Lakso et al., 1992, Proc. Natl. Acad. Sci. USA 89: 6232-36; which are incorporated herein by reference in their entireties); the FLP recombinase system of *Saccharomyces cerevisiae* (O'Gorman et al., 1991, Science 251: 1351-55); the Cre-loxP-tetracycline control switch (Gossen and Bujard, 1992, Proc. Natl. Acad. Sci. USA 89: 5547-51); and ligand-regulated recombinase system (Kellendonk et al., 1999, J. Mol. Biol. 285: 175-82; incorporated herein by reference in its entirety). Preferably, the recombinase is highly active, e.g., the Cre-loxP or the FLPe system, and has enhanced thermostability (Rodríguez et al., 2000, Nature Genetics 25: 139-40; incorporated herein by reference in its entirety).

In certain embodiments, a recombinase system can be linked to a second inducible or repressible transcriptional regulation system. For example, a cell-specific Cre-loxP mediated recombination system (Gossen and Bujard, 1992, Proc. Natl. Acad. Sci. USA 89: 5547-51) can be linked to a cell-specific tetracycline-dependent time switch detailed above (Ewald et al., 1996, Science 273: 1384-1386; Furth et al. Proc. Natl. Acad. Sci. U.S.A. 91: 9302-06 (1994); St-Onge et al., 1996, Nucleic Acids Research 24(19): 3875-77; which are incorporated herein by reference in their entireties).

In one embodiment, an altered cre gene with enhanced expression in mammalian cells is used (Gorski and Jones, 1999, Nucleic Acids Research 27(9): 2059-61; incorporated herein by reference in its entirety).

In a specific embodiment, the ligand-regulated recombinase system of Kellendonk et al. (1999, J. Mol. Biol. 285: 175-82; incorporated herein by reference in its entirety) can be used. In this system, the ligand-binding domain (LBD) of a receptor, e.g., the progesterone or estrogen receptor, is fused to the Cre recombinase to increase specificity of the recombinase.

5.13. Methods of Screening for Expression of Molecularly Tagged Ribosomal Protein Coding Sequences In preferred embodiments, the invention provides a collection of lines of transformed organisms that contain a selected subset of cells or cell population expressing molecularly-tagged ribosomes. The collection comprises at least two individual lines, preferably at least five individual lines. Each individual line is selected for the collection based on the identity of the subset of cells in which the molecularly tagged ribosomes are expressed.

Potential founder organisms for a line of transformed organisms can be screened for expression of the molecularly tagged ribosomal protein coding sequence by ribosomes in the population of cells characterized by expression of the endogenous characterizing gene.

Transformed organisms that exhibit appropriate expression (e.g., detectable expression having substantially the same expression pattern as the endogenous characterizing gene in a corresponding non-transformed organism or anatomical region thereof, i.e., detectable expression in at least 80%, 90% or, preferably, 95% of the cells shown to express the endogenous gene by in situ hybridization) are selected as lines of transformed organisms.

In a preferred embodiment, immunohistochemistry using an antibody specific for the molecular tag or a marker activated or repressed thereby is used to detect expression of the molecular tag.

5.14. Profiling of mRNA Species

Once isolated, the mRNA bound by the tagged ribosomal proteins or mRNA binding proteins of the invention can be analyzed by any method known in the art. In one aspect of the invention, the gene expression profile of cells expressing the tagged ribosomal proteins or mRNA binding proteins is analyzed using any number of methods known in the art, for example but not by way of limitation, by isolating the mRNA and constructing cDNA libraries or by labeling the RNA for gene expression analysis.

In a preferred embodiment, poly-$A^+$ RNA (mRNA) is isolated from the tagged ribosomal proteins or mRNA binding proteins of the invention, and converted to cDNA through a reverse transcription reaction primed by a first primer that comprises an oligo-dT sequence. The first primer is contacted with the poly-$A^+$ RNA under conditions that allow the oligo-dT site to hybridize to the first selected sequence (i.e., the poly-A sequence). Alternatively, the first primer comprises a sequence that is the reverse complement of a specific selected sequence (for example, a sequence characteristic of a family of mRNAs).

The first primer is then used to prime synthesis of a first-strand cDNA by reverse transcription of the source single-stranded nucleic acid. When the source nucleic acid is mRNA, a RNA-dependent DNA polymerase activity is required to convert the primer-source mRNA hybrid to a first-strand cDNA-source mRNA hybrid. A reverse transcriptase can be used to catalyze RNA-dependent DNA polymerase activity.

Reverse transcriptase is found in all retroviruses and is commonly derived from Moloney murine leukemia virus (M-MLV-RT), avian myeloblastosis virus (AMV-RT), bovine leukemia virus (BLV-RT), Rous sarcoma virus (RSV-RT), and human immunodeficiency virus (HIV-RT); enzymes from these sources are commercially available (e.g., Life Technologies-Gibco BRL, Rockville, Md.; Roche Molecular Biochemicals, Indianapolis, Ind.; PanVera, Madison Wis.).

A single reverse transcriptase or a combination of two or more reverse transcriptases (e.g., M-MLV-RT and AMV-RT) can be used to catalyze reverse transcription and first-strand cDNA synthesis. Such reverse transcriptases are used to convert a primer-single-stranded nucleic acid (mRNA) hybrid to a first-strand cDNA-primer-single-stranded nucleic acid hybrid in the presence of additional reagents that include, but are not limited to: dNTPs; monovalent and divalent cations, e.g., KCl, $MgCl_2$; sulfhydryl reagents, e.g., dithiothreitol (DTT); and buffering agents, e.g., Tris-Cl.

As described below (second-strand cDNA synthesis), the catalytic activities required to convert a first-strand cDNA-single-stranded nucleic acid hybrid to ds cDNA are an RNase H activity and a DNA-dependent DNA polymerase activity. Most reverse transcriptases, such as the ones described above (i.e., M-MLV-RT, AMV-RT, BLV-RT, RSV-RT, and HIV-RT) also catalyze each of these activities. Therefore, in certain embodiments, the reverse transcriptase employed for first-strand cDNA synthesis remains in the reaction mixture where it can also serve to catalyze second-strand cDNA synthesis. Alternatively, a variety of proteins that catalyze one or two of these activities can be added to the cDNA synthesis reaction. Such proteins may be added together during a single reaction step, or added sequentially during two or more substeps.

Preferably a reverse transcriptase lacking RNase H activity is used, in particular when long transcripts are desired. For example, M-MLV reverse transcriptase lacking RNase H activity (Kotewicz et al., U.S. Pat. No. 5,405,776, issued Apr. 11, 1995; commercially available as SUPERSCRIPTII™ (Life Technologies—Gibco BRL) can be used to catalyze both RNA-dependent DNA polymerase activity and DNA-dependent DNA polymerase activity. In a preferred embodiment, SUPERSCRIPT II™ (Life Technologies—Gibco BRL) is used as a source of DNA polymerase activity. This DNA polymerase can be used to synthesize a complementary DNA strand from single-stranded RNA, DNA, or an RNA:DNA hybrid. SUPERSCRIPTII™ is genetically engineered by the introduction of point mutations that greatly reduce its RNase H activity but preserve full DNA polymerase activity. The structural modification of the enzyme therefore eliminates almost all degradation of RNA molecules during first-strand cDNA synthesis.

In certain embodiments, the reverse transcriptase is inactivated after first-strand synthesis. The reverse transcriptase may be rendered inactive using any convenient protocol. The transcriptase may be irreversibly or reversibly rendered inactive. Where the transcriptase is reversibly rendered inactive, the transcriptase is physically or chemically altered so as to no longer be able to catalyze RNA-dependent DNA polymerase activity.

The reverse transcriptase may be irreversibly inactivated by any convenient means. In certain embodiments, the reverse transcriptase is heat inactivated. The reaction mixture is subjected to heating to a temperature sufficient to inactivate the reverse transcriptase prior to commencement of the transcription step. In these embodiments, the temperature of the reaction mixture, and therefore the reverse transcriptase present therein, is typically raised to 55° C. to 70° C. for 5 to 60 minutes, preferably to about 65° C. for 15 minutes. In a preferred embodiment, the transcriptase is inactivated by adding 1M KOH to the reaction mixture, preferably to make a final concentration of 50 mM KOH in the reaction mixture, and by incubating at 65° C. for 15 mM prior to commencement of the transcription step. This step ensures that contaminating non-poly-A RNA is removed from the sample, making the subsequent tailing reaction more efficient.

Alternatively, reverse transcriptase may irreversibly inactivated by introducing a reagent into the reaction mixture that chemically alters the protein so that it no longer has RNA-dependent DNA polymerase activity.

In a preferred embodiment, the reverse transcription reaction to synthesize the first-strand cDNA proceeds at 42° C. for 30-40 min using SUPERSCRIPTII™ as the source of reverse transcriptase/DNA polymerase.

The transcribed first-strand cDNA may be isolated from the source RNA to which it is hybridized by any of wide variety of established methods. For example, the isolation method may involve treating the RNA with a nuclease such as RNase H, a denaturant such as heat or an alkali, etc., and/or separating the strands by electrophoresis. The second strand of cDNA can be synthesized using methods well known in the art, for example using reverse transcriptase which primes from the hairpin loop structure that forms at the 3' end of the first strand of cDNA.

Gene expression in cells treated and not treated with a compound of interest or in cells from animals treated or untreated with a particular treatment, e.g., pharmaceutical or surgical treatment, may be compared. In addition, mRNA bound by the tagged ribosomal proteins or mRNA binding proteins may also be analyzed, for example by northern blot analysis, PCR, RNase protection, etc., for the presence of mRNAs encoding certain protein products and for changes in the presence or levels of these mRNAs depending on the treatment of the cells. In specific embodiments, the mRNA is isolated from different populations of cells or from populations of cells exposed to different stimuli.

In another aspect, mRNA bound by the tagged ribosomal proteins or mRNA binding proteins may be used to produce a cDNA library and, in fact, a collection of such cell type specific cDNA libraries may be generated from different populations of isolated cells. Such cDNA libraries are useful to analyze gene expression, isolate and identify cell type-specific genes, splice variants and non-coding RNAs. In another aspect, such cell-type specific libraries prepared from mRNA bound by, and isolated from, the tagged ribosomal proteins or mRNA binding proteins from treated and untreated transgenic animals of the invention or from transgenic animals of the invention having and not having a disease state can be used, for example in subtractive hybridization procedures, to identify genes expressed at higher or lower levels in response to a particular treatment or in a disease state as compared to untreated transgenic animals. The mRNA isolated from the tagged ribosomal proteins or mRNA binding proteins may also be analyzed using particular microarrays generated and analyzed by methods well known in the art. Gene expression analysis using microarray technology is well known in the art. Methods for making microarrays are taught, for example, in U.S. Pat. No. 5,700,637 by Southern, U.S. Pat. No. 5,510,270 by Fodor et al. and PCT publication WO 99/35293 by Albrecht et al., which are incorporated by reference in their entireties. By probing a microarray with various populations of mRNAs, transcribed genes in certain cell populations can be identified. Moreover, the pattern of gene expression in different cell types of cell states may be readily compared.

Data from such analyses may be used to generate a database of gene expression analysis for different populations of cells in the animal or in particular tissues or anatomical regions, for example, in the brain. Using such a database together with bioinformatics tools, such as hierarchical and non-hierarchical clustering analysis and principal components analysis, cells are "fingerprinted" for particular indications from healthy and disease-model animals or tissues.

In yet another embodiment, specific cells or cell populations that express a potential a molecularly tagged ribosomal protein or mRNA binding protein are isolated from the collection and analyzed for specific protein-protein interactions or an entire protein profile using proteomics methods known in the art, for example, chromatography, mass spectroscopy, 2D gel analysis, etc.

Other types of assays may be used to analyze the cell population expressing the molecularly tagged ribosomal protein or mRNA binding protein, either in vivo, in explanted or sectioned tissue or in the isolated cells, for example, to monitor the response of the cells to a certain treatment or candidate compound or to compare the response of the animals, tissue or cells to expression of the target or inhibitor thereof, with animals, tissue or cells from animals not expressing the target or inhibitor thereof. The cells may be monitored, for example, but not by way of limitation, for changes in electrophysiology, physiology (for example, changes in physiological parameters of cells, such as intracellular or extracellular calcium or other ion concentration, change in pH, change in the presence or amount of second messengers, cell morphology, cell viability, indicators of apoptosis, secretion of secreted factors, cell replication, contact inhibition, etc.), morphology, etc.

In particular embodiments, the isolated mRNA is used to probe a comprehensive expression library (see, e.g., Serafini et al., U.S. Pat. No. 6,110,711, issued Aug. 29, 2000, which is incorporated by reference herein). The library may be normalized and presented in a high density array. Because approximately one tenth of the mRNA species in a typical somatic cell constitute 50% to 65% of the mRNA present, the cDNA library may be normalized using reassociation-kinetics based methods. (See Soares, 1997, Curr. Opin. Biotechnol. 8:542-546).

In a particular embodiment, a subpopulation of cells expressing a molecularly tagged ribosomal protein or mRNA

6. EXAMPLE 1

Tagging of Ribosomal Proteins

6.1. Isolation of Ribosomal Protein-encoding cDNAs

This example demonstrates the successful introduction of a Strep-tag into ribosomal subunit protein-encoding cDNAs.

Oligonucleotides complementary to the sequence of ribosomal subunit proteins, S6, and L37 were designed to permit PCR amplification of the cDNAs from reverse transcribed mRNA. EcoRI and NotI restrictions sites were incorporated into the 5' terminal ends of the 5' and 3' specific oligonucleotides to facility the subcloning of the amplified cDNAs into the expression vector pcDNA3.1+. The sequence of the oligonucleotide sets were as follows:

```
S6
5' oligo.
                                            (SEQ ID NO: 7)
GGAATTCATTCAAGATGAAGCTGAACATCTCCTTCCC 3' oligo.
                                            (SEQ ID NO: 8)
GCGGCCGCTTTTCTGACTGGATTCAGACTTAGAAGTAGAAGCT L37
5' oligo.
                                            (SEQ ID NO: 9)
GGAATTCCCGGCGACATGGCTAAACGCACCAAGAAGG 3' oligo.
                                            (SEQ ID NO: 10)
GCGGCCGCTCTGGTCTTTCAGTTCCTTCAGTCTTCTGAT S20
5' oligo.
                                            (SEQ ID NO: 11)
GGAATTCGCGCGCAACAGCCATGGCTTTTAAGGATAC 3' oligo.
                                            (SEQ ID NO: 12)
GCGGCCGCTAGCATCTGCAATGGTGACTTCCACCTCAAC L32
5' oligo.
                                            (SEQ ID NO: 13)
GGAATTCGGCATCATGGCTGCCCTTCGGCCTCTGGTG 3' oligo.
                                            (SEQ ID NO: 14)
GCGGCCGCTTTCATTCTCTTCGCTGCGTAGCCTGGC
```

Mouse brain cDNA (Clontech) was used as the template for a polymerase chain reaction (PCR). 50 mL PCR aliquots were prepared for each set of primer pairs. Each reaction consisted of 40 mL PCR-grade water, 5 mL 10× Advantage 2 PCR Buffer (Clontech), 1 mL mouse brain cDNA template, 1 mL each 5' and 3' oligonucleotide primer (10 mM), 1 mL dNTP mix (10 mM each dATP, dCTP, dTTP, and dGTP), and 1 mL 50× Advantage 2 Polymerase Mix.

The PCR reaction was carried out under the following conditions:
1. 95° C. for 1 minute
2. 30 cycles of 95° C. for 15 seconds and 68° C. for 1 minute 10 mL of each reaction was analyzed by electrophoresis through a 1.2% agarose gel in TAE. The remainder of the reaction was purified using a QIAGEN QUICKSPIN PCR reaction purification kit following the manufacturer's protocol.

Purified DNA was digested with EcoRI and NotI followed by electrophoresis through a 1.2% agarose gel, isolation of the DNA fragment, and extraction of the DNA from the gel using a QIAGEN QUICKSPIN Gel isolation kit following the manufacturer's protocol.

Each cDNA fragment was ligated to pcDNA3.1+, which had been digested with EcoRI and NotI. Ligated DNA was used to transform chemically competent DH5a bacteria. Transformed bacteria were plated onto LB plates containing 100 mg/mL ampicillin. For each ligation, 3 ampicillin resistant colonies were picked, grown in 5 mL LB cultures containing 100 mg/mL ampicillin.

The cultures were incubated for 16 hours on a shaking platform at 37° C. Plasmid DNA was isolated from the cultures using a QIAGEN miniprep kit following the manufacturer's protocol. Plasmid DNA was digested with PmeI and analyzed on a 1.2% agarose gel to identify plasmids that contain the cDNA insert.

6.2. Addition of Strep-tag to the Ribosomal Subunit Proteins

The amino acid sequence Trp-Ser-His-Pro-Gln-Phe-Glu-Lys (SEQ ID NO: 17) represents Strep-tag II, a peptide that is able to bind with high affinity to the protein Streptavidin. Proteins that contain the Strep-tag II can be identified and isolated through affinity to Streptavidin. Strep-tag II was added to each of the ribosomal subunit proteins, S6, S20, L32, and L37, at the C-terminus of the protein. Two complementary oligonucleotide adaptors were designed that encode for Strep-tag II. These complementary oligonucleotide adaptors, when hybridized to form a double stranded DNA, can be ligated in-frame to the ribosomal subunit cDNAs in the vector pcDNA3.1+.

The sequences of the Strep-tag II oligonucleotides were:

```
Upper strand oligonucleotide
                                            (SEQ ID NO: 15)
5' GGCCGCAGCGCTTGGAGCCACCCGCAGTTCGAAAAATAA 3'

Bottom strand oligonucleotide
                                            (SEQ ID NO: 16)
5' TCGATTATTTTTCGAACTGCGGGTGGCTCCAAGCGCTGC 3'
```

Each of the plasmids containing the ribosomal subunit protein-encoding cDNAs was digested with NotI and XhoI. The upper strand and bottom strand oligonucleotides were mixed in equal molar ratios, heated to 70° C., and allowed to cool to room temperature. The hybridized oligonucleotides were then ligated to the NotI and XhoI digested plasmids. The ligation reactions were transformed into competent DH5a bacteria and plated onto LB plates supplemented with 100 mg/mL ampicillin.

For each ligation, five ampicillin resistant colonies were picked into 5 mL LB cultures containing 100 mg/mL ampicillin. The cultures were grown at 37° C. for 16 hours. Plasmid DNA was harvested, cut with PmeI, and analyzed by electrophoresis through 5% non denaturing polyacrylamide gels. Untagged ribosomal subunit protein encoding cDNAs were also digested with PmeI, and run side by side with the tagged versions to identify the cDNAs that contained the strep-tagII sequence. All tagged cDNAs were then sequenced to confirm the sequence of each cDNA.

7. EXAMPLE 2

Isolation and Immunoprecipitation of Polysomes

7.1. Polysome Isolation

Plasmid constructs expressing tagged ribosomal proteins were transfected into Human Embryonic Kidney (HEK293) cells using the transfection reagent FuGENE 6 (Roche Applied Science) following the manufacturer's procedures. Briefly, for each transfection, 100 mL of serum free medium (DMEM) was placed into a sterile tube, followed by the addition of three mL of Fugene 6 and 1 mg of plasmid DNA. The Fugene 6/DNA mixture was allowed to incubate at room temperature for 15 minutes before being added to a 60 mm plate of HEK293 cells grown in DMEM supplemented with 10% fetal calf serum, glutamine, and antibiotics.

Three days after transfection, the cells were harvested by scraping into homogenization buffer (50 mM sucrose, 200 mM ammonium chloride, 7 mM magnesium acetate, 1 mM dithiothreitol, and 20 mM Tris-HCl, pH 7.6). The cells were lysed by the addition of the detergent, NP-40, to a concentration of 0.5% followed by five strokes in a glass dounce tissue homogenizer. Unlysed cells, nuclei and mitochondria were pelleted by centrifugation at 10,000×g for 10 minutes, at 4° C. The supernatant was carefully removed and layered over a two-step discontinuous gradient of 1.8 M and 1.0 M sucrose in 100 mM ammonium chloride, 5 mM magnesium acetate, 1 mM dithiothreitol, 20 mM Tris-HCl (pH 7.6). The gradient was centrifuged for 18 hours at 98,000×g at 4° C.

Following centrifugation, the supernatants were carefully removed, and the polysome pellet was resuspended in 100 mM ammonium chloride, 5 mM magnesium chloride, 1 mM DTT and 20 mM Tris-HCl (pH 7.6).

An equal volume of 2× denaturing protein electrophoresis sample buffer was added to each of the polysome samples. Solubilized polysomal proteins were fractionated by electrophoresis through a SDS containing 4-20% gradient polyacrylamide gel, and transferred to a nitrocellulose filter. The filter was quenched for 1 hour in PBS containing 5% dry milk followed by incubation with rabbit antisera specific for the strep-tag II amino acid sequence epitope Trp-Ser-His-Pro-Gln-Phe-Glu-Lys (SEQ ID NO: 17). The filters were rinsed three times in PBS for 20 minutes each, followed by a one hour incubation with a goat anti-rabbit antisera that had been conjugated to horse radish peroxidase (HRP), in PBS containing 10% dry milk. The filters were then washed for three times in PBS. The HRP was detected by incubating the filter in 20 mL of PBS, containing 4-chlornaphtol and hydrogen peroxidase.

As seen in FIG. 1, polysomes from cells transfected with plasmids expressing tagged versions of ribosomal proteins S6 (lane 2, in duplicate), L32 (lane 4, in duplicate, not easily seen in the reproduction), and L37 (lane 5, in duplicate) contain proteins that are reactive to the anti-streptag II antibodies. These proteins correspond to the predicted molecular weights of the S6 (34 kDa), L32 (52 kDa), and L37 (9 kDa). The S6 and L37 proteins appear to be more abundantly represented in the polysomal fraction compared to the L32 protein, which is difficult to visualize in the figure but is present upon close inspection of the original filter. Tagged S20 (lane 3, in duplicate) does not appear to be present in the polysomal fraction. Polysomes from untransfected cells (lane 1, in duplicate) do not display any immunoreactive material.

7.2. Polysome Immunoprecipitation

HEK 293 cells were transfected with plasmid constructs expressing tagged ribosomal proteins S6 or L37 and homogenized as above. Unlysed cells, nuclei, and mitochondria were removed by centrifugation at 10,000×g for 10 minutes. 5 micrograms of an anti-streptag rabbit polyclonal antisera was added to the supernatant and incubated at 4° C. for 72 hours. 100 microliters of a protein A sepharose slurry was then added and incubation continued at 4° C. for one hour. The sepharose beads were pelleted by centrifugation at 1,000×g for 5 minutes. The supernatant was removed, and the pellet was resuspended in 10 mLs of fresh homogenization buffer. This procedure was repeated three times.

RNA was harvested from the protein A sepharose pellet using an RNA isolation kit (Ambion). Briefly, the pellets were solubilized in 600 microliters of homogenization buffer, followed by the addition of 600 microliters of 64% EtOH. This mixture was applied to the spin column provided by the kit, followed by centrifugation at 10,000×g for 1 minute. The column was sequentially washed in the two wash buffers provided with the kit. RNA bound to the column was released by the addition of elution buffer heated to 95° C. RNA was visualized by electrophoresis through an ethidium bromide containing agarose gel.

Figure 2:
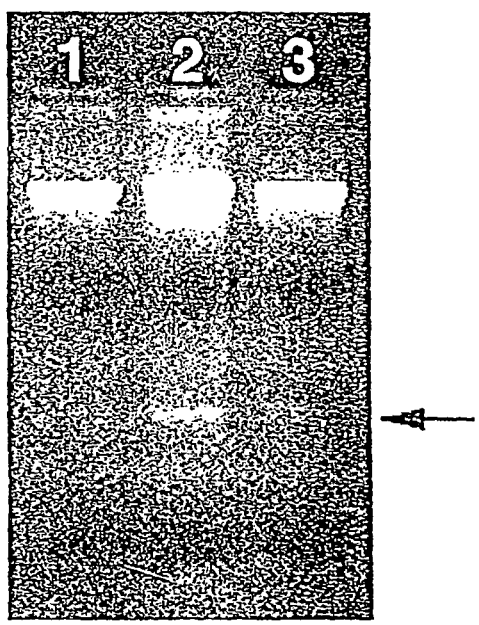
FIG. 2. Ribosomal RNA is present (arrow) in material immunoprecipitated from tagged S6 (lane 2) transfectants. Such RNA is also present at low levels in material from tagged L37 transfectants (lane 3). Such RNA is not present in material from untransfected cells (lane 1).

As seen in FIG. 2, ribosomal RNA is present (arrow) in material immunoprecipitated from tagged S6 (lane 2) transfectants. Such RNA is also present at low levels in material from tagged L37 transfectants (lane 3; not easily seen in reproduction). Such RNA is not present in material from untransfected cells (lane 1).

All references cited herein are incorporated herein by reference in their entireties and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A non-human-transgenic mammal comprising a transgene comprising a nucleotide sequence encoding a ribosomal fusion protein, wherein said ribosomal fusion protein comprises a ribosomal protein, or fragment thereof, fused to a peptide tag, wherein said nucleotide sequence is operably linked to a mammalian endogenous promoter, wherein said mammalian endogenous promoter causes expression of said ribosomal fusion protein in a chosen cell type, and wherein said ribosomal fusion protein is incorporated in an intact ribosome that translates and/or binds mRNA.

2. The non-human-transgenic mammal of claim 1, wherein said peptide tag is not a ribosomal protein.

3. The non-human transgenic mammal of claim 1, wherein said ribosomal protein is S6, S15, S18, L10a, L32, or L37.

4. The non-human transgenic mammal of claim 1, wherein said peptide tag is placed at the N- or C- terminus of said ribosomal protein.

5. The non-human transgenic mammal of claim 1, wherein said peptide tag does not inhibit or interfere with a function of said ribosomal protein.

6. The non-human transgenic mammal of claim 1, wherein said ribosomal fusion protein is not translated in a cell type that is not chosen.

7. The non-human transgenic mammal of claim 1, wherein said chosen cell type comprises neural cells.

8. The non-human transgenic mammal of claim 7, wherein said neural cells comprise neuronal cells.

9. The non-human transgenic mammal of claim 1, wherein said transgenic mammal is a mouse.

10. The non-human transgenic mammal of claim 1, wherein said peptide tag is streptavidin.

11. The non-human transgenic mammal of claim 1, wherein said peptide tag comprises 200 or more amino acids.

12. The non-human transgenic mammal of claim 1, wherein said mammalian endogenous promoter is from a characterizing gene.

13. The non-human transgenic mammal of claim 12, wherein said expression of said nucleotide sequence is substantially similar to expression of said characterizing gene.

14. The non-human transgenic mammal of claim 12, wherein said expression of said nucleotide sequence is in at least 80% of cells shown to express said characterizing gene in said mammal.

15. The non-human transgenic mammal of claim 1, wherein said mammalian endogenous promoter is part of an endogenous regulatory sequence.

16. The non-human transgenic mammal of claim 15, wherein said endogenous regulatory sequence is at least or about 100 kilobases in length.

17. The non-human transgenic mammal of claim 15, wherein said endogenous regulatory sequence is at least or about 200 kilobases in length.

18. The non-human transgenic mammal of claim 15, wherein said endogenous regulatory sequence comprises a transcription regulatory element.

19. The non-human transgenic mammal of claim 18, wherein said transcription regulatory element comprises a transcriptional enhancer sequence, an insulator sequence, or a combination thereof.

20. The non-human transgenic mammal of claim 1, wherein said nucleotide sequence is operably linked to a regulatory sequence associated with or part of a bacterial artificial chromosome (BAC).

21. A cell of said non-human transgenic mammal of claim 1 comprising said transgene comprising a nucleotide sequence encoding a ribosomal fusion protein, wherein said ribosomal fusion protein comprises a ribosomal protein, or fragment thereof, fused to a peptide tag, wherein said nucleotide sequence is operably linked to a mammalian endogenous promoter, wherein said mammalian endogenous promoter causes expression of said ribosomal fusion protein in said cell, and wherein said ribosomal fusion protein is incorporated in an intact ribosome that translates and/or binds mRNA.

22. The non-human transgenic mammal of claim 1, wherein said transgenic mammal is a rodent.

23. The non-human transgenic mammal of claim 1, wherein said transgenic mammal is a rat.

24. The non-human transgenic mammal of claim 1, wherein said mammalian endogenous promoter is a rodent endogenous promoter.

25. The non-human transgenic mammal of claim 1 or 9, wherein said mammalian endogenous promoter is a mouse endogenous promoter.

26. The non-human transgenic mammal of claim 1 or 23, wherein said mammalian endogenous promoter is a rat endogenous promoter.

27. A non-human transgenic mammal comprising a transgene comprising a nucleotide sequence encoding a mRNA binding fusion protein, wherein said mRNA binding fusion protein comprises a mRNA binding protein, or fragment thereof, fused to a peptide tag, wherein said nucleotide sequence is operably linked to a mammalian endogenous promoter, wherein said mammalian endogenous promoter causes expression of said mRNA binding fusion protein in a chosen cell type.

28. The non-human transgenic mammal of claim 27, wherein said peptide tag is not a mRNA binding protein.

29. The non-human transgenic mammal of claim 27, wherein said mRNA binding fusion protein is not a polyA binding protein.

30. The non-human transgenic mammal of claim 27, wherein said peptide tag is placed at the N- or C- terminus of said mRNA binding protein.

31. The non-human transgenic mammal of claim 27, wherein said peptide tag does not inhibit or interfere with a function of said mRNA binding protein.

32. The non-human transgenic mammal of claim 27, wherein said transgenic mammal is a rodent.

33. The non-human transgenic mammal of claim 27, wherein said transgenic mammal is a mouse.

34. The non-human transgenic mammal of claim 27, wherein said transgenic mammal is a rat.

35. The non-human transgenic mammal of claim 27, wherein said mammalian endogenous promoter is a rodent endogenous promoter.

36. The non-human transgenic mammal of claim 27 or 33, wherein said mammalian endogenous promoter is a mouse endogenous promoter.

37. The non-human transgenic mammal of claim 27 or 34, wherein said mammalian endogenous promoter is a rat endogenous promoter.

38. The non-human transgenic mammal of claim 27, wherein said ribosomal fusion protein is not translated in a cell type that is not chosen.

39. A transgenic mouse comprising a nucleotide sequence encoding a ribosomal fusion protein, wherein said ribosomal fusion protein comprises a ribosomal protein, or fragment thereof, fused to a peptide tag, wherein said nucleotide sequence is operatively linked to a mouse endogenous regulatory sequence comprising a promoter, wherein said mouse endogenous promoter causes expression of said ribosomal fusion protein in a chosen cell type, and wherein said ribosomal fusion protein is incorporated in an intact ribosome that translates and/or binds mRNA.

40. A method of making said non-human transgenic mammal of claim 1, comprising introducing into a fertilized egg or zygote a transgene comprising a nucleotide sequence encoding a ribosomal fusion protein, wherein said ribosomal fusion protein comprises a ribosomal protein, or fragment thereof, fused to a peptide tag, wherein said nucleotide sequence is operably linked to a mammalian endogenous promoter of a chosen cell type.

41. A method of isolating an actively translated mRNA from said non-human transgenic mammal of claim 1, comprising:
  (a) contacting a cell isolated from said non-human transgenic mammal or a lysate of said cell that comprises said ribosomal-fusion protein with a reagent that binds to said peptide tag;
  (b) isolating said ribosomal fusion protein containing said peptide tag; and
  (c) isolating said actively translated mRNA from said ribosomes.

42. The method of claim 41, wherein said reagent is bound to a solid support.

43. The method of claim 41, wherein said peptide tag is streptavidin and said reagent specifically binds streptavidin.

44. The method of claim 41, wherein said chosen cell type is a neural cell.

45. The method of claim 44, wherein said neural cell is a neuronal cell.

46. The method of claim 41, wherein said peptide tag comprises 200 or more amino acids.

47. The method of claim 41, wherein said mammalian endogenous promoter is from a characterizing gene.

48. The method of claim 47, wherein said expression of said nucleotide sequence is substantially similar to expression of said characterizing gene.

49. The method of claim 47, wherein said expression of said nucleotide sequence is in at least 80% of cells shown to express said characterizing gene in said mammal.

50. The method of claim 41, wherein said mammalian endogenous promoter is part of an endogenous regulatory sequence.

51. The method of claim 50, wherein said endogenous regulatory sequence is at least or about 100 kilobases in length.

52. The method of claim 50, wherein said endogenous regulatory sequence is at least or about 200 kilobases in length.

53. The method of claim 50, wherein said endogenous regulatory sequence comprises a transcription regulatory element.

54. The method of claim 53, wherein said transcription regulatory element comprises a transcriptional enhancer sequence, insulator sequence, or a combination thereof.

55. The method of claim 41, wherein said nucleotide sequence is operably linked to a regulatory sequence associated with or part of a bacterial artificial chromosome (BAC).

56. The method of claim 41, further comprising contacting said cell with an agent capable of arresting translation.

57. The method of claim 41, further comprising determining a gene expression profile for said cell.

58. The method of claim 41, further comprising identifying said actively translated mRNA.

59. The method of claim 41, further comprising quantifying said actively translated mRNA.

60. A transgene comprising a nucleotide sequence encoding a ribosomal fusion protein, wherein said ribosomal fusion protein comprises a ribosomal protein, or fragment thereof, fused to a peptide tag, wherein said nucleotide sequence is operably linked to a non-human mammalian endogenous promoter, wherein said mammalian endogenous promoter causes expression of said ribosomal fusion protein in a chosen cell type, and wherein said ribosomal fusion protein is incorporated in an intact ribosome that translates and/or binds mRNA.

61. The transgene of claim 60, wherein said ribosomal protein is S6, S15, S18, L10a, L32, or L37.

62. The transgene of claim 60, wherein said peptide tag is placed at the N- or C-terminus of said ribosomal protein.

63. A transgene comprising a nucleotide sequence encoding a mRNA binding fusion protein, wherein said mRNA binding fusion protein comprises a mRNA binding protein, or fragment thereof, fused to a peptide tag, wherein said nucleotide sequence is operably linked to a mammalian endogenous promoter, wherein said mammalian endogenous promoter causes expression of said mRNA binding fusion protein in a chosen cell type.

64. The transgene of claim 63, wherein said peptide tag is placed at the N- or C- terminus of said mRNA binding protein.

65. The transgene of claim 63, wherein said mammalian endogenous promoter is a rodent endogenous promoter.

66. The transgene of claim 63, wherein said mammalian endogenous promoter is a mouse endogenous promoter.

67. The transgene of claim 63, wherein said mammalian endogenous promoter is a rat endogenous promoter.

68. The transgene of claim 60, wherein said mammalian endogenous promoter is part of an endogenous regulatory sequence that is at least or about 100 kilobases in length.

69. The transgene of claim 60, wherein said mammalian endogenous promoter is part of an endogenous regulatory sequence that is at least or about 200 kilobases in length.

70. The transgene of claim 60, wherein said mammalian endogenous promoter is part of an endogenous regulatory sequence that comprises a transcription regulatory element.

71. The transgene of claim 70, wherein said transcription regulatory element comprises a transcriptional enhancer sequence, insulator sequence, or a combination thereof.

72. The transgene of claim 60, wherein said nucleotide sequence is operably linked to a regulatory sequence associated with or part of a bacterial artificial chromosome (BAC).

73. The transgene of claim 60, wherein said mammalian endogenous promoter is a rodent endogenous promoter.

74. The transgene of claim 60, wherein said mammalian endogenous promoter is a mouse endogenous promoter.

75. The transgene of claim 60, wherein said mammalian endogenous promoter is a rat endogenous promoter.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Influenza virus

<400> SEQUENCE: 1
```

Tyr Pro Tyr Asp Val Pro Asp Tyr Ala
1               5

<210> SEQ ID NO 2
<211> LENGTH: 10
<212> TYPE: PRT
<213> ORGANISM: Homo sapiens

<400> SEQUENCE: 2

Glu Gln Lys Leu Ile Ser Glu Glu Asp Leu
1               5                   10

<210> SEQ ID NO 3
<211> LENGTH: 6
<212> TYPE: PRT
<213> ORGANISM: Bluetongue virus

<400> SEQUENCE: 3

Gln Tyr Pro Ala Leu Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Lys Asp Asp Asp Asp Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Trp Arg His Pro Gln Phe Gly Gly
1               5

<210> SEQ ID NO 6
<211> LENGTH: 551
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
taacgttact ggccgaagcc gcttggaata aggccggtgt gcgtttgtct atatgttatt      60
ttccaccata ttgccgtctt ttggcaatgt gagggcccgg aaacctggcc ctgtcttctt    120
gacgagcatt cctaggggtc tttcccctct cgccaaagga atgcaaggtc tgttgaatgt    180
cgtgaaggaa gcagttcctc tggaagcttc ttgaagacaa caacgtctg tagcgaccct     240 ttgcaggcag cggaaccccc cacctggcga caggtgcctc tgcggccaaa agccacgtgt    300
ataagataca cctgcaaagg cggcacaacc ccagtgccac gttgtgagtt ggatagttgt    360
ggaaagagtc aaatggctct cctaagcgta ttcaacaagg gctgaagga tgcccagaag     420 gtactccatt gtatgggatc tgatctgggg cctcggtgca catgctttac atgtgtttag    480

```
tcgaggttaa aaaaacgtct aggcccccg aaccacgggg acgtggtttt cctttgaaaa      540
acaccatgat a                                                          551
```

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ggaattcatt caagatgaag ctgaacatct ccttccc                              37
```

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
tcgaagatga agattcagac ttaggtcagt cttttcgccg gcg                       43
```

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ggaattcccg gcgacatggc taaacgcacc aagaagg                              37
```

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
tagtcttctg acttccttga ctttctggtc tcgccggcg                            39
```

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
ggaattcgcg cgcaacagcc atggctttta aggatac                              37
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
caactccacc ttcagtggta acgtctacga tcgccggcg                                 39

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaattcggc atcatggctg cccttcggcc tctggtg                                   37

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggtccgatg cgtcgcttct cttactttcg ccggcg                                    36

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggccgcagcg cttggagcca cccgcagttc gaaaaataa                                 39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcgattattt ttcgaactgc gggtggctcc aagcgctgc                                 39

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ser His Pro Gln Phe Glu Lys
1               5
```